United States Patent
Schaffer et al.

(10) Patent No.: US 7,238,658 B2
(45) Date of Patent: Jul. 3, 2007

(54) CRYSTALLIZATION OF IGF-1

(75) Inventors: Michelle Schaffer, Cambridge (GB); Mark Ultsch, Mill Valley, CA (US); Felix Vajdos, Ledyard, CT (US)

(73) Assignee: Genentech, Inc., South San Francisco, CA (US)

( * ) Notice: Subject to any disclaimer, the term of this patent is extended or adjusted under 35 U.S.C. 154(b) by 267 days.

(21) Appl. No.: 11/107,672

(22) Filed: Apr. 14, 2005

(65) Prior Publication Data

US 2005/0215477 A1 Sep. 29, 2005

Related U.S. Application Data

(62) Division of application No. 10/066,009, filed on Feb. 1, 2002, now Pat. No. 7,084,240.

(60) Provisional application No. 60/267,977, filed on Feb. 9, 2001, provisional application No. 60/287,072, filed on Apr. 27, 2001.

(51) Int. Cl.
*A01N 38/18* (2006.01)
(52) U.S. Cl. .................. 514/2; 530/324; 530/344
(58) Field of Classification Search .............. None
See application file for complete search history.

(56) References Cited

U.S. PATENT DOCUMENTS

| | | | |
|---|---|---|---|
| 4,672,108 A | 6/1987 | Kung et al. |
| 4,833,233 A | 5/1989 | Carter |
| 4,876,242 A | 10/1989 | Applebaum et al. |
| 4,959,351 A | 9/1990 | Grau |
| 4,988,675 A | 1/1991 | Froesch et al. |
| 5,028,587 A | 7/1991 | Dorschug et al. |
| 5,068,224 A | 11/1991 | Fryklund et al. |
| 5,077,276 A | 12/1991 | Ballard et al. |
| 5,093,317 A | 3/1992 | Lewis et al. |
| 5,106,832 A | 4/1992 | Froesch et al. |
| 5,126,324 A | 6/1992 | Clark et al. |

(Continued)

FOREIGN PATENT DOCUMENTS

EP 668914 8/1995

(Continued)

OTHER PUBLICATIONS

Cavanagh, et al., *Protein NMR Spectroscopy: Principles and Practice*, New York Academic Press, Inc., pp. 447-451, 478-518 and 525-528 (1996).

(Continued)

*Primary Examiner*—Nashaat T. Nashed
(74) *Attorney, Agent, or Firm*—Janet E. Hasak, Esq.; Ginger R. Dreger, Esq.; Heller Ehrman, LLP

(57) ABSTRACT

Crystalline IGF-1 is provided along with a method for production thereof. Crystallizing IGF-1 comprises the steps of mixing an aqueous solution comprising IGF-1 with a reservoir solution comprising a precipitant to form a mixture; and crystallizing the mixture, optionally also recrystallizing and isolating the crystalline IGF-1. In addition, a method for identifying IGF-1 indirect agonists is provided using a detergent as a standard for the level of inhibition of binding of IGFBP-1 or IGFBP-3 to IGF-1 and/or using the coordinates of the binding pockets of IGF-1 to which a candidate indirect agonist binds for structure-based drug design.

8 Claims, 10 Drawing Sheets

U.S. PATENT DOCUMENTS

| | | | |
|---|---|---|---|
| 5,164,370 | A | 11/1992 | Ballard et al. |
| 5,187,151 | A | 2/1993 | Clark et al. |
| 5,202,119 | A | 4/1993 | Clark et al. |
| 5,273,961 | A | 12/1993 | Clark |
| 5,374,620 | A | 12/1994 | Clark et al. |
| 5,461,031 | A | 10/1995 | De Felippis |
| 5,466,670 | A | 11/1995 | Dunger et al. |
| 5,470,828 | A | 11/1995 | Ballard et al. |
| 5,504,188 | A | 4/1996 | Baker et al. |
| 5,534,488 | A | 7/1996 | Hoffmann |
| 5,547,930 | A | 8/1996 | Balschmidt |
| 5,569,648 | A | 10/1996 | Lewis et al. |
| 5,597,893 | A | 1/1997 | Baker et al. |
| 5,650,486 | A | 7/1997 | De Felippis |
| 5,714,460 | A | 2/1998 | Gluckman et al. |
| 5,747,642 | A | 5/1998 | De Felippis |
| 5,834,422 | A | 11/1998 | Balschmidt |
| 5,840,680 | A | 11/1998 | Balschmidt |
| 5,898,028 | A | 4/1999 | Jensen et al. |
| 5,898,067 | A | 4/1999 | Balschmidt et al. |
| 5,948,751 | A | 9/1999 | Kimer et al. |
| 5,952,297 | A | 9/1999 | De Felippis et al. |
| 6,127,334 | A | 10/2000 | Kimer et al. |

FOREIGN PATENT DOCUMENTS

| | | |
|---|---|---|
| WO | 91/03253 | 3/1991 |
| WO | WO 91/03253 | 3/1991 |
| WO | 92/11865 | 7/1992 |
| WO | WO 92/11865 | 7/1992 |
| WO | 93/08826 | 5/1993 |
| WO | WO 93/08826 | 5/1993 |
| WO | 93/23067 | 11/1993 |
| WO | 93/23071 | 11/1993 |
| WO | WO 93/23067 | 11/1993 |
| WO | WO 93/23071 | 11/1993 |
| WO | 93/25219 | 12/1993 |
| WO | WO 93/25219 | 12/1993 |
| WO | WO 94/04569 | 3/1994 |
| WO | WO 94/16722 | 8/1994 |
| WO | WO 96/01124 | 1/1996 |
| WO | WO 96/33216 | 10/1996 |
| WO | WO 97/00895 | 1/1997 |
| WO | WO 98/45427 | 10/1998 |
| WO | WO 99/01476 | 1/1999 |
| WO | WO 99/38011 | 7/1999 |
| WO | 00/23469 | 4/2000 |
| WO | WO 00/23469 | 4/2000 |
| WO | WO 01/72771 | 4/2001 |
| WO | 02/098914 | 12/2002 |

OTHER PUBLICATIONS

Van Wyk, et al., "The Somatomedins: A Family of Insulinlike Hormones under Growth Hormone Control", *Recent Prog. Horm. Res.*, 30:259-318 (1974).

Adams et al., "Structure of Rhombohedral 2 Zinc Insulin Crystals," *Nature*. 224:491-495 (Nov. 1969).

Bach and Rechler, "Insulin-Like Growth Factor Binding Proteins." *Diabetes Reviews*. 3(1):38-61 (1995).

Baker et al., "Role of Insulin-Like Growth Factors in Embryonic and Postnatal Growth." *Cell*. 75:73-82 (Oct. 1993).

Ballard et al., "Does IGF-I Ever Act Through the Insulin Receptor?" *The Insulin-Like Growth Factors and Their Regulatory Proteins.*, Baxter, eds., Amsterdam: Elsevier pp. 131-138 (1994).

Bar et al., "Tissue Localization of Perfused Endothelial Cell IGF Binding Protein is Markedly Altered by Association with IGF-I." *Endocrinology*. 127(6):3243-3245 (1990).

Barinaga, M., "Neurotrophic Factors Enter the Clinic (News)." *Science*. 264:772-774 (1994).

Baserga., "The Insulin-Like Growth Factor 1 Receptor: A Key to Tumor Growth?" *Cancer Research* 55:249-252 (Jan. 1995).

Baxter, "Physiological Roles of IGF Binding Proteins" *Modern Concepts of Insulin-like Growth Factors*. Spencer, eds., Elsevier, New York pp. 371-380 (1991).

Baxter., "The Somatomedins: Insulin-Like Growth Factors." *Advances in Clinical Chemistry*. 25:49-115 (1986).

Bayne et al., "Structural Analogs of Human Insulin-Like Growth Factors I with Reduced Affinity for Serum Binding Proteins and the Type 2 Insulin-Like Growth Factor Receptor." *J. Bio. Chem.* 263:6233-6239 (1988).

Bayne et al., "The C Region of Human Insulin-Like Growth Factor (IGF) I is Required for High Affinity Binding to the Type 1 IGF Receptor." *J. Bio. Chem.* 264(19):11004-11008 (1988).

Bayne et al., "The Roles of Tyrosines 24, 31, and 60 in the High Affinity Binding of Insuling-Like Growth Factor-I to the Type I Insulin-Like Growth Factor Receptor." *J. Bio. Chem.* 265(26):15648-15652 (Sep. 15, 1990).

Binoux, M., "Recent Data on Somatomedins (Insulin-Like Growth Factors)." *Annales d'Endocrinologie* (English Abstract Included) 41:157-192 (1980).

Blundell et al., "Insulin-Like Growth Factor: A Model for Tertiary Structure Accounting for Immunoreactivity and Receptor Binding." *Proc. Natl. Acad. Sci. USA* 75(1):180-184 (Jan. 1978).

Blundell et al., "Tertiary Structures, Receptor Binding, and Antigenicity of Insulinlike Growth Factors." *Federation Proc.* 42:2592-2597 (1983).

Bondy, C., "Clinical Uses of Insulin-Like Growth Factor I." *Annals of Internal Medicine*, 120:593-601 (1994).

Buckbinder et al., "Induction of the Growth Inhibitor IGF-Binding Protein 3 by p53." *Nature*. 377:646-649 (Oct. 1995).

Cascieri et al., "Mutants of Human Insulin-Like Growth Factor I with Reduced Affinity for the Type 1 Insulin-Like Growth Factor Receptor." *Biochemistry* 27 (9):3229-3233 (May 3, 1988).

Cascieri et al., "Structural Analogs of Human Insulin-Like Growth Factor (IGF) I with Altered Affinity for Type 2 IGF Receptors." *J. Bio. Chem.* 264:2199-2202 (1989).

Cavanagh et al., *Protein NMR Spectroscopy Principles and Practices.*, New York:Academic Press, Inc. (1996).

Clemmons and Van Wyk., "Somatomedin: Physiological Control and Effects on Cell Proliferation." *Handbook Exp. Pharmacol.* 57:161-208 (1981).

Clemmons et al., "Competition for Binding to Insulin-Like Growth Factor (IGF) Binding Protein-2, 3, 4, and 5 by the IGFs and IGF Analogs." *Endocrinology*. 131(2):890-895 (Aug. 1992).

Clemmons et al., "Discrete Alterations of the Insulin-Like Growth Factor I Molecule Which Alter Its Affinity for Insulin-Like Growth Factor-Binding Proteins Result in Changes in Bioactivity." *J. Bio. Chem.* 265(21):12210-12216 (1990).

Clemmons et al., "The Role of Insulin-Like Growth Factors in the Nervous System." *Anal. NY Acad. Sci. USA* 692:10-21 (1993).

Clore et al., "Stereospecific Assignment of β-Methylene Protons in Larger Proteins Using 3D $^{15}$N-Separated Hartmann-Hahn and 13$_C$-Separated Rotating Frame Overhauser Spectroscopy." *J. Biomol. NMR* 1:13-22 (1991).

Cohen et al., "Biological Effects of Prostate Specific Antigen as an Insulin-Like Growth Factor Binding Protein-3 Protease." *J. Endocrinology*. 142:407-415 (1994).

Cohen et al., "Insulin-Like Growth Factors (IGFs), IGF Receptors, and IGF-Binding Proteins in Primary Cultures of Prostate Epithelial Cells." *J. Clin. Endocrin. & Metab.* 73:401-407 (1991).

Cohen et al., "The IGF Axis in the Prostate." *Horm. & Metab. Res.* 26:81-84 (1994).

Cooke et al., "Solution Structure of Human Insulin-Like Growth Factor 1: A Nuclear Magnetic Resonance and Restrained Molecular Dynamics Study" *Biochemistry* 30:5484-5491 (1991).

Cornilescu et al., "Protein Backbone Angle Restraints From Searching a Database for Chemical Shift and Sequence Homology." *J. Biomol. NMR* 13:289-302 (1999).

Culig et al., "Androgen Receptor Activation in Prostatic Tumor Cell Lines by Insulin-Like Growth Factor-I, Keratinocyte Growth Factor, and Epidermal Growth Factor." *Cancer Research*. 54:5474-5478 (1994).

Cullen et al., "Insulin-Like Growth Factor Receptor Expression and Function in Human Breast Cancer." *Cancer Research*. 50:48-53 (1990).

Daughaday and Rotwein., "Insulin-Like Growth Factors I and II. Peptide, Messenger Ribonucleic Acid and Gene Structures, Serum, and Tissue Concentrations." *Endocrin. Rev.* 10(1) :68-91 (1989).

De Meyts., "The Structural Basis of Insulin and Insulin-Like Growth Factor-I Receptor Binding and Negative Co-Operativity, and its Relevance to Mitogenic Versus Metabolic Signalling." *Diabetologia*. (Suppl. 2) 37:S135-S148 (1994).

De Wolf et al., "Solution Structure of a Mini YGF-1." *Protein Sci.* 5:2193-2202 (1996).

Derewenda et al., "Phenol Stabilizes More Helix in a New Symmetrical Zinc Insulin Hexamer." *Nature*. 338:594-596 (Apr. 1989).

Dubaquie and Lowman, Total Alanine-Scanning Mutagenesis of Insulin-Like Growth Factor I (IGF-I) Identifies Differential Binding Epitopes for IGFBP-1 and IGFBP-3° *Biochemistry* 38(20) :6386-6396 (1999).

Dubaquie et al., "Binding Protein-3-Selective Insulin-Like Growth Factor I Variants: Engineering, Biodistributions, and Clearance." *Endocrinology*. 142(1) :165-173 (Jan. 2001).

Duerr et al., "Insulin-Like Growth Factor-1 Enhances Ventricular Hypertrophy and Function During the Onset of Experimental Cardiac Failure." *J. Clin. Invest.* 95:619-627 (1995).

Einstein and Low., "Insulin: Some Shrinkage Stages of Sulfate and Citrate Crystals." *Acta Crystallogr.* 15:32-34 (1962).

Elahi et al., "Hemodynamic and Metabolic Responses to Human Insulin-Like Growth Factor I (IGF-I) in Men." *Modern Concepts of Insulin-Like Growth Factors*., Spencer, EM, ed., New York:Elsevier Science Publ.

Fejzo et al., "The SHAPES Strategy: An NMR-Based Approach for Lead Generation in Drug Discovery." *Chemistry & Biology*. 6:755-769 (1999).

Feyen et al., "Recombinant Human [Cys$^{281}$]Insulin-Like Growth Factor-Binding Protein 2 Inhibits Both Basal and Insulin-Like Growth Factor I-Stimulated Proliferation and Collagen Synthesis in Fetal Rat Calvariae." *J Bio. Chem.* 266:19469-19474 (1991).

Figueroa et al., "Recombinant Insulin-Like Growth Factor Binding Protein-1 Inhibits IGF-I, Serum, and Estrogen-Dependent Growth of MCF-7 Human Breast Cancer Cells." *J. Cell Phys.* 157:229-236 (1993).

Froesch et al., "Metabolic and Therapeutic Effects of Insulin-Like Growth Factor I" *Horm. Res.* 42:66-71 (1994).

Garrett et al., "Crystal Structure of the First Three Domains of the Type-1 Insulin-Like Growth Factor Receptor." *Nature*. 394(6691):395-399 (Jul. 23, 1998).

Guler et al., "Recombinant Human Insulin-Like Growth Factor 1 Stimulates Growth and has Distinct Effects on Organ Size in Hypophysectomized Rats." *Proc. Natl. Acad. Sci. USA* 85:4889-4893 (1988).

Hammerman and Miller., "The Growth Hormone Insulin-Like Factor Axis in Kidney Revisited." *Am. J. Physiol.* 265:F1-F14 (1993).

Hammerman and Miller., "Therapeutic Use of Growth Factors in Renal Failure." *J. Am. Soc. Nephrol.* 5:1-11 (1994).

Hasegawa et al., "The Free Form of Insulin-Like Growth Factor I Increases in Circulation During Normal Human Pregnancy," *J. Clin. Endocrinol. Metabol.* 80:3284-3286 (1995).

Hizuka et al., "Measurement of Free Form of Insulin-Like Growth Factor I in Human Plasma," *Growth Regulation*. 1:51-55 (1991).

Horney et al., "Elevated Glucose Increases Mesangial Cell Sensitivity to Insulin-Like Growth Factor I." *Am. J. Physiol.* 274:F1045-F1053 (1998).

Hsing et al., "Regulation of Apoptosis Induced by Transforming Growth Factor-β1 in Nontumorigenic and Tumorigenic Rat Prostatic Epithelial Cell Lines." *Cancer Research*. 56:5146-5149 (1996).

Humbel., "Insulin-Like Growth Factors I and II." *European Journal of Biochemistry*. 190:445-462 (1990).

Huynh et al., "Estradiol and Antiestrogens Regulate a Growth Inhibitory Insulin-Like Growth Factor Binding Protein 3 Autocrine Loop in Human Breast Cancer Cells." *J. Bio. Chem.* 271(2):1016-1021 (1996).

Isaksson et al., "Growth Hormone Stimulates Longitudinal Bone Growth Directly." *Science*. 216:1237-1239 (1982).

Isaksson et al., "Mechanism of the Stimulatory Effect of Growth Hormone on Longitudinal Bone Growth." *Endocrine Reviews*. 8(4):426-438 (1987).

Iwamura et al., "Insulin-Like Growth Factor I: Action and Receptor Characterization in Human Prostate Cancer Cell Lines." *Prostate*. 22:243-252 (1993).

Jabri et al., "Adverse Effects of Recombinant Human Insulin-Like Growth Factor I in Obese Insulin-Resistant Type II Diabetic Patients," *Diabetes* 43:369-374 (1994).

Janin Chothia., "The Structure of Protein-Protein Recognition Sites," *J. Bio. Chem.* 265(27):16027-16030 (1990).

Jansson et al., "The Insulin-Like Growth Factor (IGF) Binding Protein 1 Binding Epitope on IGF-I Probed by Heteronuclear NMR Spectroscopy and Mutational Analysis." *J. Bio. Chem.* 273(38):24701-24707 (Sep. 18, 1998).

Jones and Clemmons., "Insulin-Like Growth Factors and Their Binding Proteins: Biological Actions." *Endocrine Rev.* 16(1):3-34 (1995).

Juul et al., "Serum Concentrations of Free and Total Insulin-Like Growth Factor-I, IGF Binding Proteins -1 and -3 and IGFBP-3 Protease Activity in Boys with Normal or Precocious Puberty." *Clin. Endocrin.* 44:515-523 (1996).

Juul et al., "Serum Insulin-Like Growth Factor-I in 1030 Healthy Children, Adolescents, and Adults: Relation to Age, Sex, Stage of Puberty, Testicular Size, and Body Mass Index." *J. Clin. Endocrin. & Metab.* 78(8):744-758 (1994).

Juul et al., "Serum Levels of Insulin-Like Growth Factor (IGF)-Binding Protein-3 (IGFBP-3) in Healthy Infants, Children, and Adolescents: The Relation to IGF-I, IGF-II, IGFBP-1, IGFBP-2, Age, Sex, Body Mass Index, and Pubertal Maturation." *J. Clin. Endocrin. & Metab.* 80:2534-2542 (1995).

Kerr et al., "Effect of Insulin-like Growth Factor-1 on the Responses to and Recognition of Hypoglycemia in Humans: A Comparison with Insulin." *J. Clin. Invest.* 91:141-147 (1993).

Kuzuya et al., "Trial of Insulinlike Growth Factor I Therapy for Patients with Extreme Insulin Resistance Syndromes." *Diabetes*. 42:696-705 (1993).

Laajoki et al., "Secondary Structure Determination of $^{15}$N-Labelled Human Long-[Arg-3]-Insulin-Like Growth Factor 1 by Multidimensional NMR Spectroscopy." *FEBS Letters* 420:97-102 (1997).

Laajoki et al., "Solution Structure and Backbone Dynamics of Long-[Arg$^3$]Insulin-Like Growth Factor-I." *J. Bio. Chem.* 275(14):10009-10015 (2000).

Lee et al., "A Pulsed Field Gradient Isotope-Filtered 3D $^{13}$C HMQC-NOESY Experiment for Extracting Intermolecular NOE Contacts in Molecular Complexes." *FEBS Letters* 350:87-90 (1994).

Lee et al., "Activation of Estrogen Receptor-Mediated Gene Transcription by IGF-I in Human Breast Cancer Cells." *J. Endocrinol.* 152:39-47 (1997).

Lee et al., "Regulation and Function of Insulin-Like Growth Factor-Binding Protein-1." *Proc. Soc. Exp. Biol. & Med.* 204:4-29 (1993).

LeRoith et al., "Insulin-Like Growth Factors and Cancer." *Annals of Internal Medicine*. 122(1):54-59 (Jan. 1995).

LeRoith., "Editorial: Insulin-Like Growth Factor I Receptor Signaling—Overlapping or Redundant Pathways?" *Endocrinology*. 141(4):1287-1288 (2000).

Lewitt and Baxter, "Insulin-Like Growth Factor-Binding Protein-1: A Role in Glucose Counterregulation?" *Mol. Cell. Endocrin.* 79(1-3):C147-C152 (1991).

Lewitt et al., "Insulin-like Growth Factor-binding Protein-1 Modulates Blood Glucose Levels" *Endocrinology* 129(4):2254-2256 (1991).

Lieberman et al., "Effects of Recombinant Human Insulin-Like Growth Factor-I (rhIGF-I) on Total and Free IGF-I Concentrations, IGF-Binding Proteins, and Glycemic Response in Humans." *J. Clin. Endocrinol. & Metab.* 75(1):30-36 (1992).

Liu et al., "Insulin-Like Growth Factor-I Affects Perinatal Lethality and Postnatal Development in a Gene Dosage-Dependent Manner: Manipulation Using the Cre-loxP System in Transgenic Mice." *Molecular Endocrinology* 12(9):1452-1462 (1998).

Liu et al., "Mice Carrying Null Mutations of the Genes Encoding Insulin-Like Growth Factor I (Igf-1) and Type I IGF Receptor (Igf1r)," *Cell.* 75:59-72 (1993).

Long et al., "Loss of the Metastatic Phenotype in Murine Carcinoma Cells Expressing an Antisense RNA to the Insulin-Like Growth Factor Receptor." *Cancer Research.* 55:1006-1009 (1995).

Lowman et al., "Molecular Mimics of Insulin-Like Growth Factor 1 (IGF-1) for Inhibiting IGF-1: IGF-Binding Protein Interactions," *Biochemistry* 37(25):8870-8878 (1998).

McGuire et al., "Regulation of Insulin-Like Growth Factor-Binding Protein (IGFBP) Expression by Breast Cancer Cells: Use of IGFBP-1 as an Inhibitor of Insulin-Like Growth Factor Action." *J. Natl. Cancer Institute* 84(17):1336-1341 (1992).

McPherson, Alexander. *Preparation and Analysis of Protein Crystals.* (Second Edition), Malabar, FL:Robert E. Krieger Publishing Comp. (1989).

Morrow et al., "Recombinant Human (rh) IGF-1 Reverses Hyperglycemia and Improves Insulin Sensitivity in Severe Insulin Resistance" *Diabetes-53rd Annual Meeting,* Jun. 12-15, 1993 (Suppl. 1, abstract No. 269) 42:83A (1993).

Oh et al., "Antiproliferative Actions of Insulin-Like Growth Factor Binding Protein (IGFBP)-3 in Human Breast Cancer Cells." *Prog. Growth Factor Res.* 6(2-4):503-512 (1995).

Oh et al., "Characterization of the Affinities of Insulin-Like Growth Factor (IGF)-Binding Proteins 1-4 for IGF-I, IGF-II, IGF-I/Insulin Hybrid, and IGF-I Analogs." *Endocrinology.* 132:1337-1344 (1993).

Oh et al., "Insulin-Like Growth Factor (IGF)-Independent Action of IGF-Binding Protein-3 in Hs578T Human Breast Cancer Cells." *J. Bio. Chem.* 268(20):14964-14971 (1993).

Peterkofsky et al., "Elevated Activity of Low Molecular Weight Insulin-Like Growth Factor-Binding Proteins in Sera of Vitamin C-Deficient and Fasted Guinea Pigs" *Endocrinology* 128(4):1769-1779 (1991).

Pietrzkowski et al., "Inhibition of Cellular Proliferation by Peptide Analogues of Insulin-Like Growth Factor 1." *Cancer Research.* 52:6447-6451 (1992).

Powell-Braxton et al., "IGF-I is Required for Normal Embryonic Growth in Mice." *Genes Dev.* 7:2609-2617 (1993).

Pratt and Pollak., "Insulin-Like Growth Factor Binding Protein 3 (IGF-BP3) Inhibits Estrogen-Stimulated Breast Cancer Cell Proliferation." *Biophys. Res. Comm.* 198(1):292-297 (1994).

Quin et al., "Acute Response to Recombinant Insulin-Like Growth Factor-I in a Patient with Mendenhall's Syndrome." *New Engl. J. Med.* 323(20):1425-1426 (1990).

Quinn et al., "Insulin-Like Growth Factor Expression in Human Cancer Cell Lines." *J. Bio. Chem.* 271(19):11477-11483 (1996).

Rajah et al., "Insulin-Like Growth Factor (IGF)-Binding Protein-3 Induces Apoptosis and Mediates the Effects of Transforming Growth Factor-β1 on Programmed Cell Death through a p53- and IGF-Independent Mechanism." *J. Bio. Chem.* 272(18):12181-12188 (1997).

Reilly and Fairbrother., "A Novel Isotope Labeling Protocol for Bacterially Expressed Proteins." *J. Biomol. NMR* 4:459-462 (1994).

Rinderknecht and Humbel, "Amino-Terminal Sequences of Two Polypeptides From Human Serum with Nonsuppressible Insulin-Like and Cell-Growth-Promoting Activities: Evidence for Structural Homology with Insulin B Chain." *Proc. Natl. Acad. Sci. USA* 73(12):4379-4381 (1976).

Rinderknecht and Humbel., "The Amino Acid Sequence of Human Insulin-Like Growth Factor I and Its Structural Homology with Proinsulin." *Journal of Biological Chemistry* 253(8):2769-2776 (1978).

Rohlik et al., "An Antibody to the Receptor for Insulin-Like Growth Factor I Inhibits the Growth of MCF-7 Cells in Tissue Culture." *Biochem. & Biophys. Res. Comm.* 149(1):276-281 (Nov. 1987).

Saad et al., "Low Doses of Insulin-Like Growth Factor-I Improve Insulin Sensitivity." *Diabetologia.* (Abstract 152) 37:A40 (Supp. 1 1994).

Sato et al., "Three-Dimensional Structure of Human Insulin-Like Growth Factor-I (IGF-I) Determined by $^1$H-NMR and Distance Geometry." *Int. J. Pep. Protein Res.* 41:433-440 (1993).

Schalch et al., "Short-Term Effects of Recombinant Human Insulin-Like Growth Factor I on Metabolic Control of Patients with Type II Diabetes Mellitus" *J. of Clinical Endocrinology & Metabolism* 77(6):1563-1568 (1993).

Schalch et al., "Short-Term Metabolic Effects of Recombinant Human Insulin-Like Growth Factor I (rhTGF-I) in Type II Diabetes Mellitus." *Modern Concepts of Insulin-Like Growth Factors.*, Spencer, ed., New York:Elsevier Science Publ. Co. pp. 705-713 (1991).

Schlechter et al., "Evidence Suggesting that the Direct Growth-Promoting Effect of Growth Hormone on Cartilage In Vivo is Mediated by Local Production of Somatomedin." *Proc. Natl. Acad. Sci. USA* 83:7932-7934 (1986).

Schoenle et al., "Recombinant Human Insulin-Like Growth Factor I (rhIGF I) Reduces Hyperglycaemia in Patients with Extreme Insulin Resistance." *Diabetologia.* 34:675-679 (1991).

Sjogren et al., "Liver-Derived Insulin-Like Growth Factor I (IGF-I) is the Principal Source of IGF-I in Blood but is Not Required for Postnatal Body Growth in Mice." *Proc. Natl. Acad. Sci. USA* 96:7088-7092 (1999).

Smith et al., "Essential Role of Growth Hormone in Ischemia-Induced Retinal Neovascularization." *Science.* 276:1706-1709 (1997).

Steller et al., "Overexpression of the Insulin-Like Growth Factor-1 Receptor and Autocrine Stimulation in Human Cervical Cells." *Cancer Research.* 56:1761-1765 (1996).

Stracke et al., "The Type I Insulin-Like Growth Factor Receptor is a Motility Receptor in Human Melanoma Cells." *J. Bio. Chem.* 264(36):21544-21549 (Dec. 1989).

Suikkari et al., "Insulin Regulates the Serum Levels of Low Molecular Weight Insulin-Like Growth Factor-Binding Protein." *J. Clin. Endocrin. Metabol.* 66:266-272 (1988).

Tollefsen and Thompson., "The Structural Basis for Insulin-Like Growth Factor I Receptor High Affinity Binding." *J. Bio. Chem.* 263(31):16267-16273 (1988).

Torres et al., "Solution Structure of Human Insulin-Like Growth Factor IX: Relationship to Receptor and Binding Protein Interaction." *J. Mol. Bio.* 248(2):385-401 (Apr. 28, 1995).

Usala et al., "Brief Report: Treatment of Insulin-Resistant Diabetic Ketoacidosis with Insulin-Like Growth Factor I in an Adolescent with Insulin-Dependent Diabetes." *New Engl. J. Med.* 327(12):853-857 (1992).

Vajdos et al., "Crystal Structure of Human Insulin-Like Growth Factor-1: Detergent Binding Inhibits Binding Protein Interactions." *Biochemistry* 40:11022-11029 (2001).

Valentinis et al., "The Human Insulin-Like Growth Factor (IGF) Binding Protein-3 Inhibits the Growth of Fibroblasts with a Targeted Disruption of the IGF-I Receptor Gene." *Molecular Endocrinology.* 9:361-367 (1995).

Van Holds., "X-Ray Diffraction," *Physical Biochemistry.*, NJ:Prentice Hall, Chapter 11, pp. 221-239 (1971).

Van Wyk et al., "The Somatomedins: A Family of Insulinlike Hormones Under Growth Hormone Control." *Recent Prog. Horm. Res.* 30:259-318 (1974).

Vlachopapadopoulou et al., "Metabolic and Clinical Response to Recombinant Human Insulin-like Growth Factor I in Myotonic Dystrophy—A Clinical Research Center Study" *J. Clin. Endo. Metab.* 80(12):3715-3723 (1995).

Weber., "Physical Principles of Protein Crystallization." *Advances in Protein Chemistry.* 41:1-36 (1991).

Yee et al., "Insulin-Like Growth Factor Binding Protein 1 Expression Inhibits Insulin-Like Growth Factor I Action in MCF-7 Breast Cancer Cells." *Cell Growth & Diff.* 5:73-77 (1994).

Zenobi et al., "Effects of Insulin-Like Growth Factor-I on Glucose Tolerance, Insulin Levels, and Insulin Secretion." *J. Clin. Invest.* 89:1908-1913 (1992).

Zenobi et al., "Insulin-Like Growth Factor-I Improves Glucose and Lipid Metabolism in Type 2 Diabetes Mellitus." *J. Clin. Invest.* 90:2234-2241 (1992).

Zeslawski et al., "The Interaction of Insulin-Like Growth Factor-I with the N-Terminal Domain of IGFBP-5." *EMBO Journal.* 20(14):3638-3644 (2001).

De Bree et al., "Preparation and Characterization of the Recombinant Selenomethionine Analogue of Insulin-Like Growth Factor-1." *Protein Expression & Purification.* 13:319-325 (1998).

Eisenstein et al., "Biological Function Made Crystal Clear—Annotation of Hypothetical Proteins Via Structural Genomics." *Current Opinion in Biotechnology* 11(1):25-30 (Feb. 2000).

Gilliland and Ladner., "Crystallization of Biological Macromolecules for X-Ray Diffraction Studies." *Current Opinion in Structural Biology* 6(5):595-603 (Oct. 1996).

Skelly and Madden., "Overexpression, Isolation, and Crystallization of Proteins." *Methods in Molecular Biology.*, New Jersey:Humana Press Inc., Chapter 2, vol. 56:23-53 (1996).

Baxter, Robert C., "Insulin-like Growth Factor (IGF)-binding Proteins: Interactions With IGFs and Intrinsic Bioactivities", Am J Physical Endocrinal Metab., 278: E967-E976, 2000.

Bühler, Hemut, et al., "Inhibition of Rat Renal 11β-Hydroxysteroid Dehydrogenasse by Steroidal Compounds and Triterpenoids; Structure/Function Relationship", Biochimica Et Biophysica Acta, 1075, pp. 206-212 (1991).

Hjelmeland, Leonard M., et al., "A New Class of Nonionic Detergents with a Gluconamide Polar Group", Analytical Biochemistry, 130, pp. 485-490 (1983).

Sedzik, J., et al., "Solubilization of PNS Myelin Membrane Proteins by Detergents", Membrane Biophysics and Biochemistry, vol. 11, No. 113, pp. 2559-2563, Aug. 2000.

```
              *  *  *  *       * *          ! *   !  !                          *
IGF-1  G . . . PETLCGAELVDALQFVCGDRGFYFNKPTGYGSSSRRAPQTGIVDECCFR-
IGF-2  AYRPSETLCGGELVDTLQFVCGDRGFYFSRPAS . . RVSRRSR . . GIVEECCFR-
INS    F . . VNQHLCGSHLVEALYLVCGERGFFYTPK . . . . . . . . . . . . . . . . GIVEQCCTS-

!    *
IGF-1  SCDLRRLEMYCAPLKPAKSA        (SEQ ID NO:1)
IGF-2  SCDLALLETYCA T . . PAKSE    (SEQ ID NO:2)
INS    ICSLYQLENYCN                (SEQ ID NO:3)
```

*FIG._1*

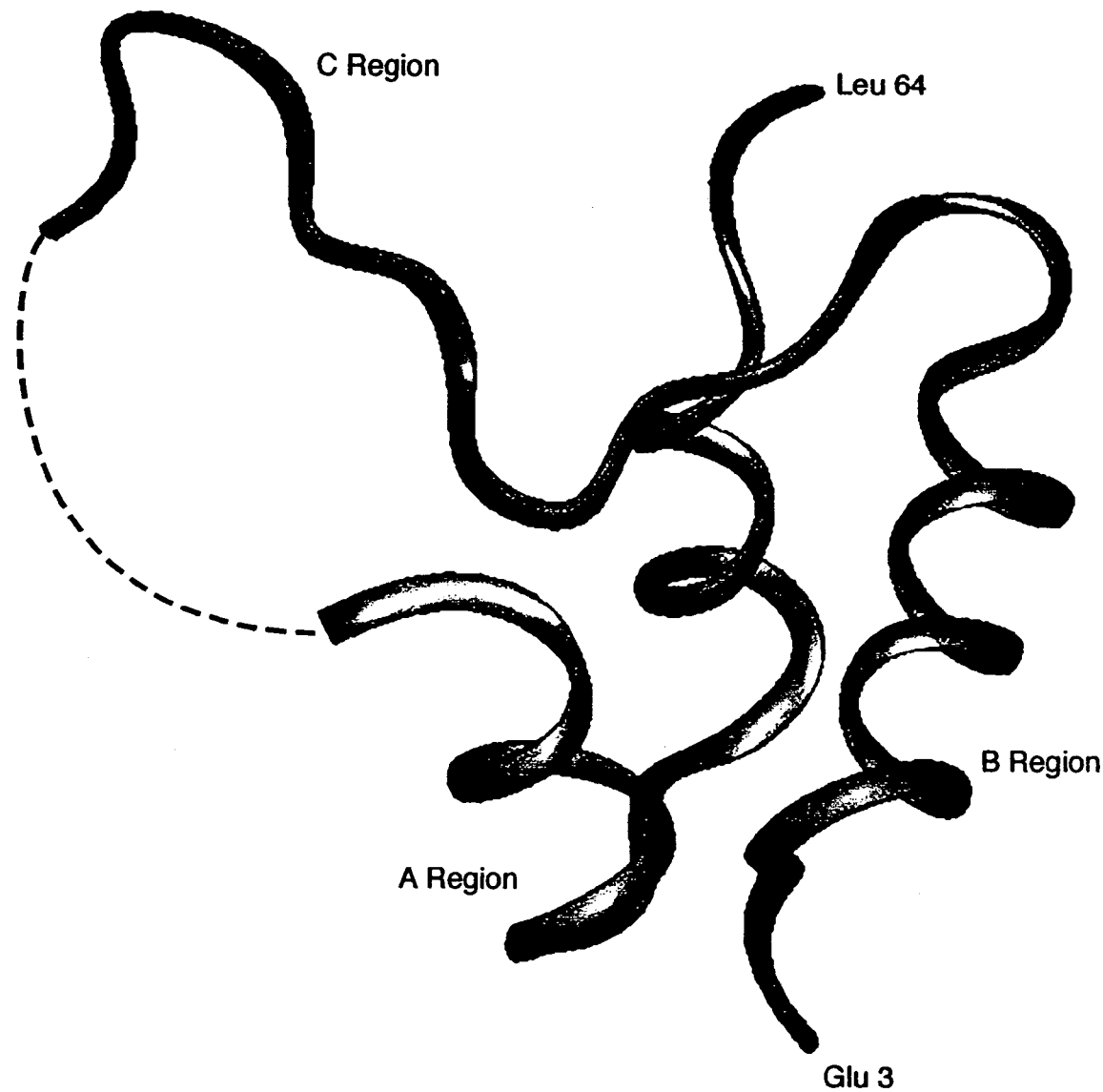
FIG._2

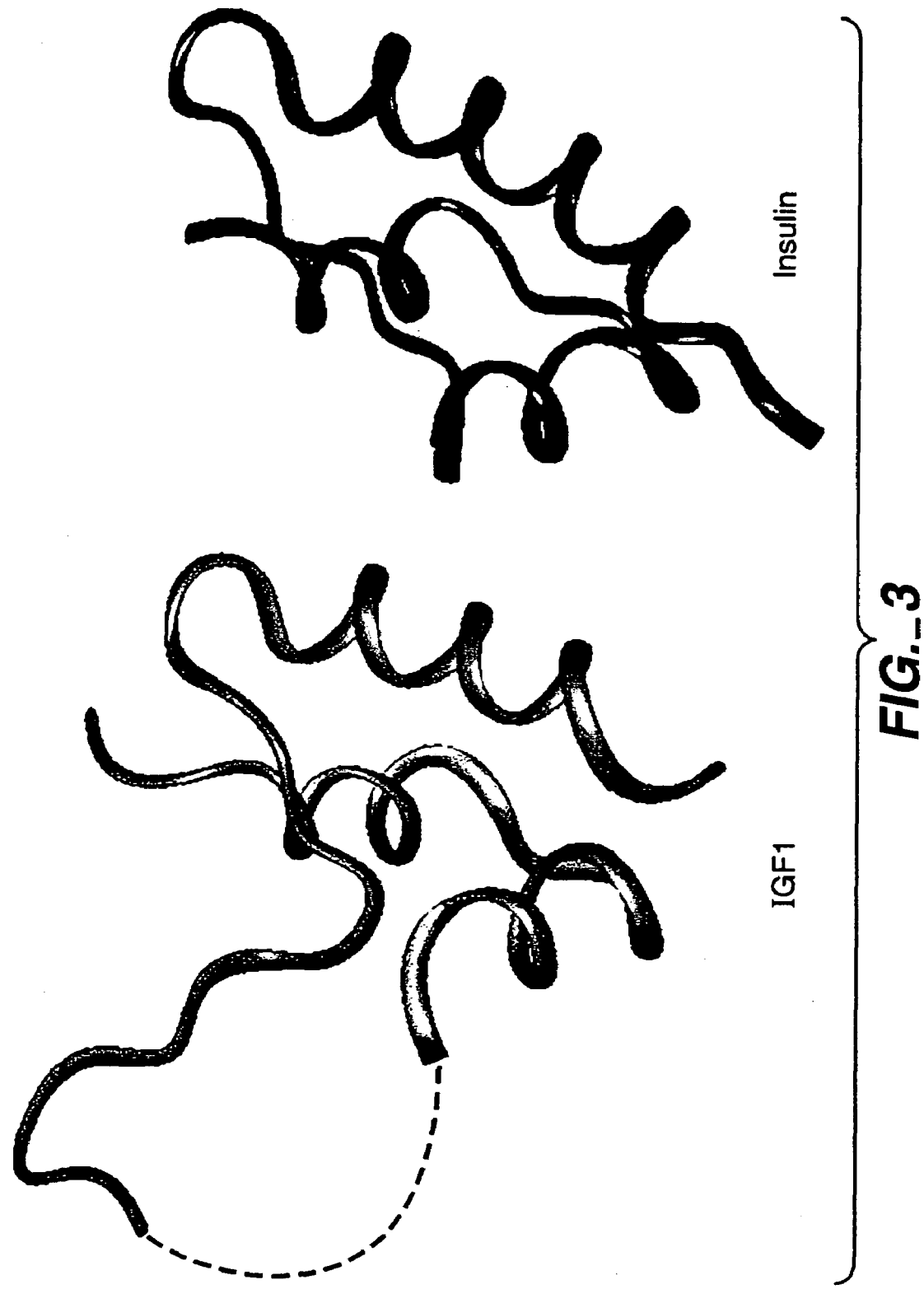
FIG._3

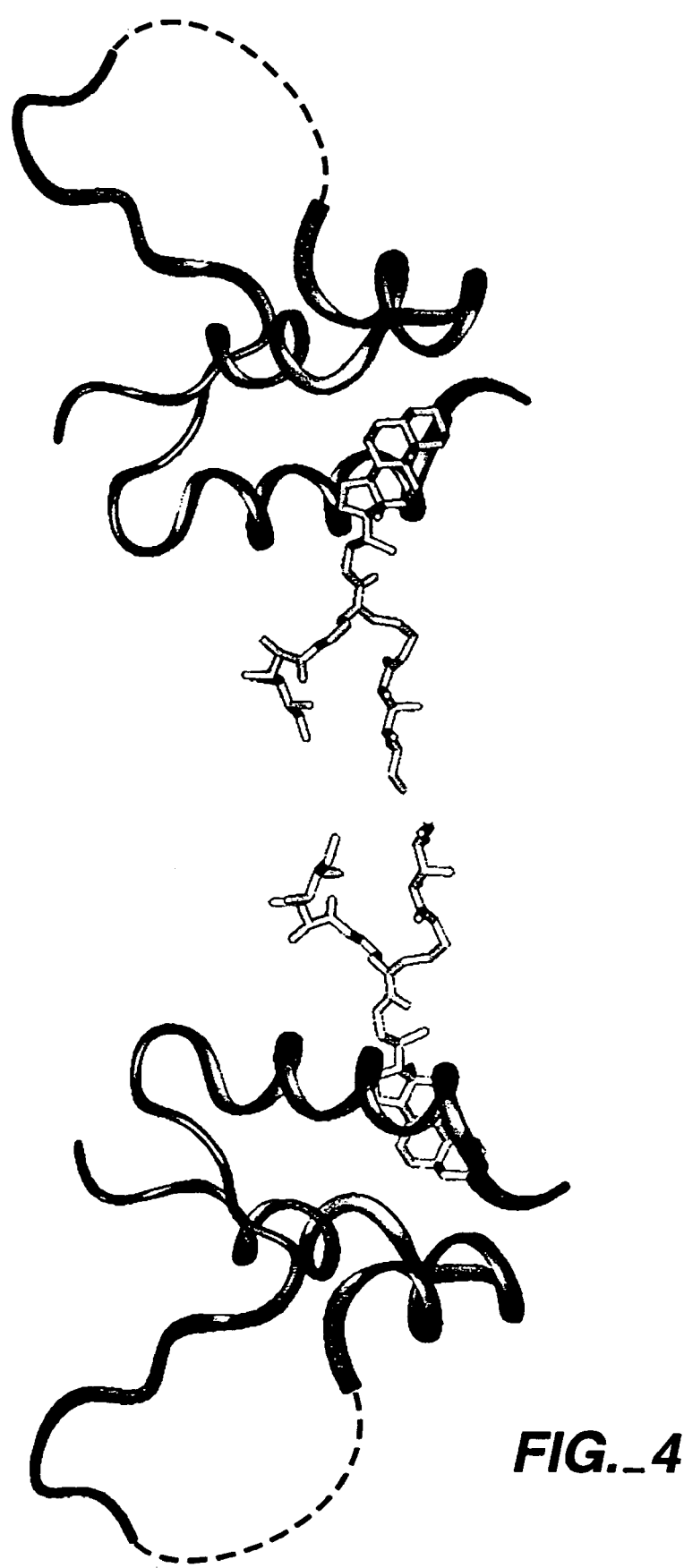
FIG._4

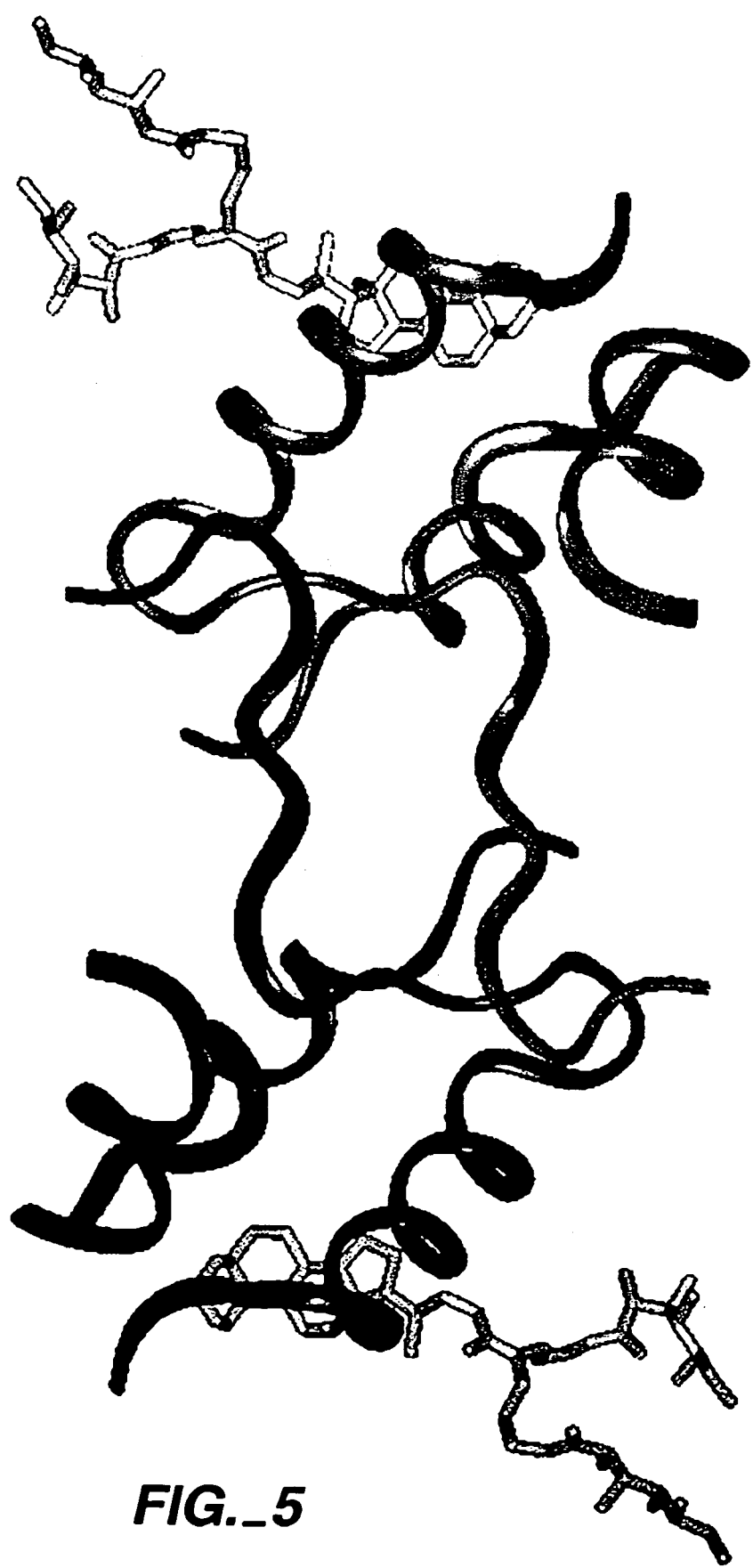
FIG._5

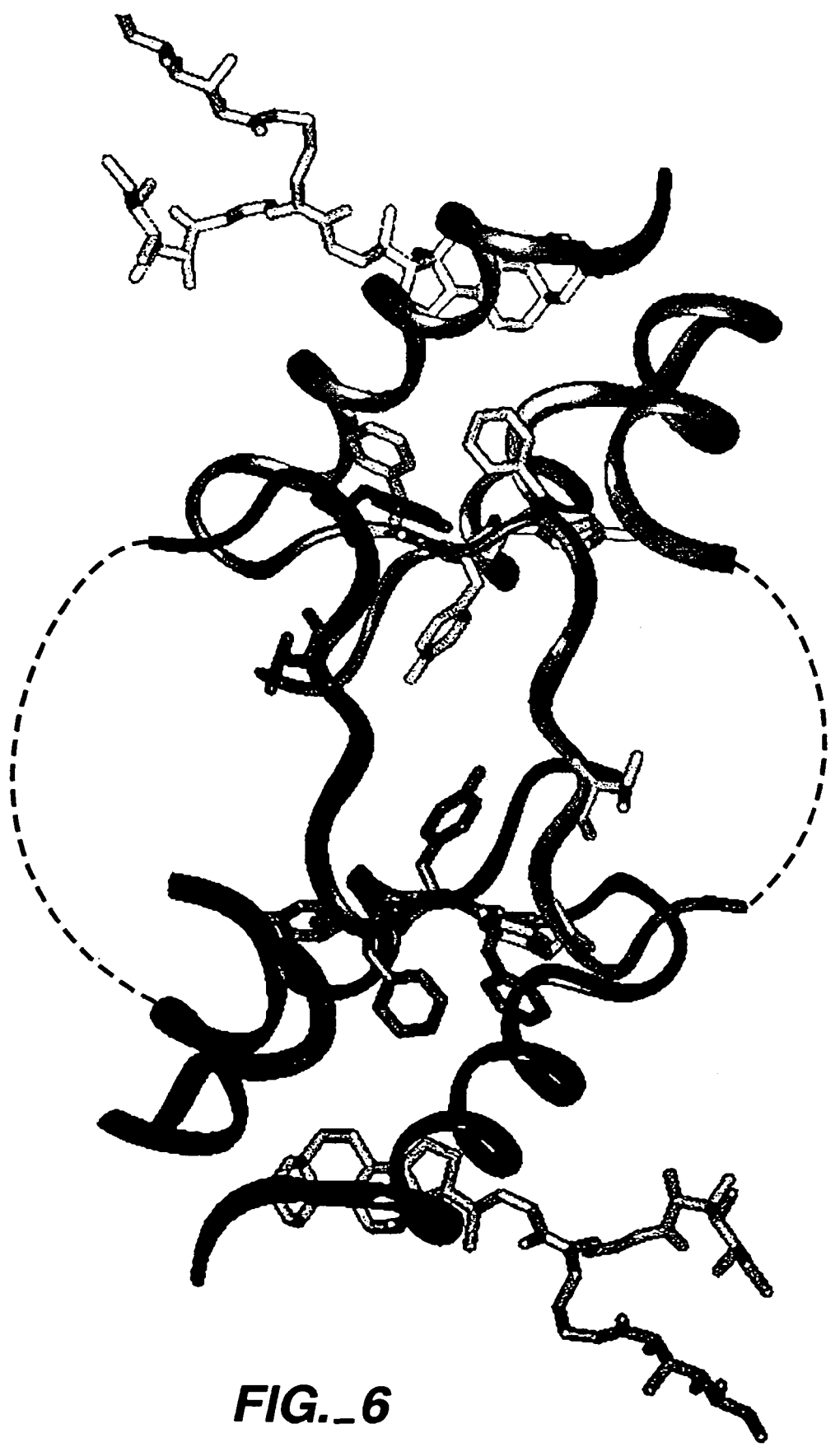
FIG._6

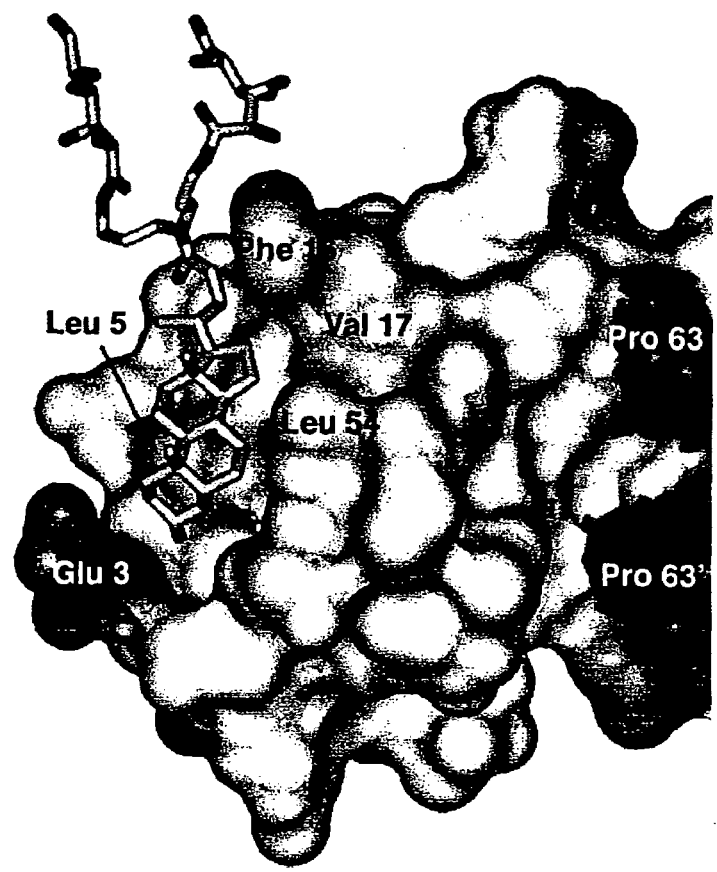
FIG._7A
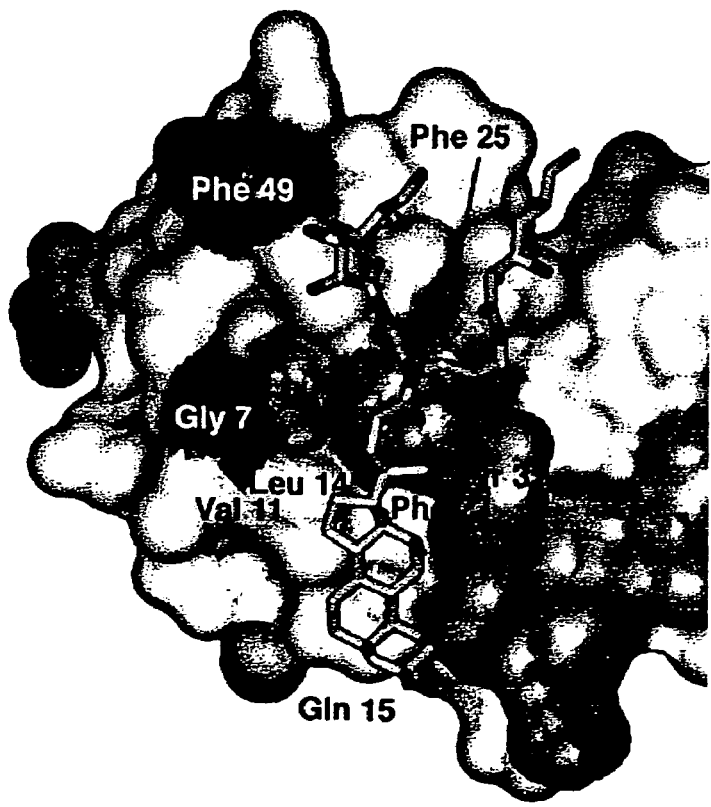
FIG._7B

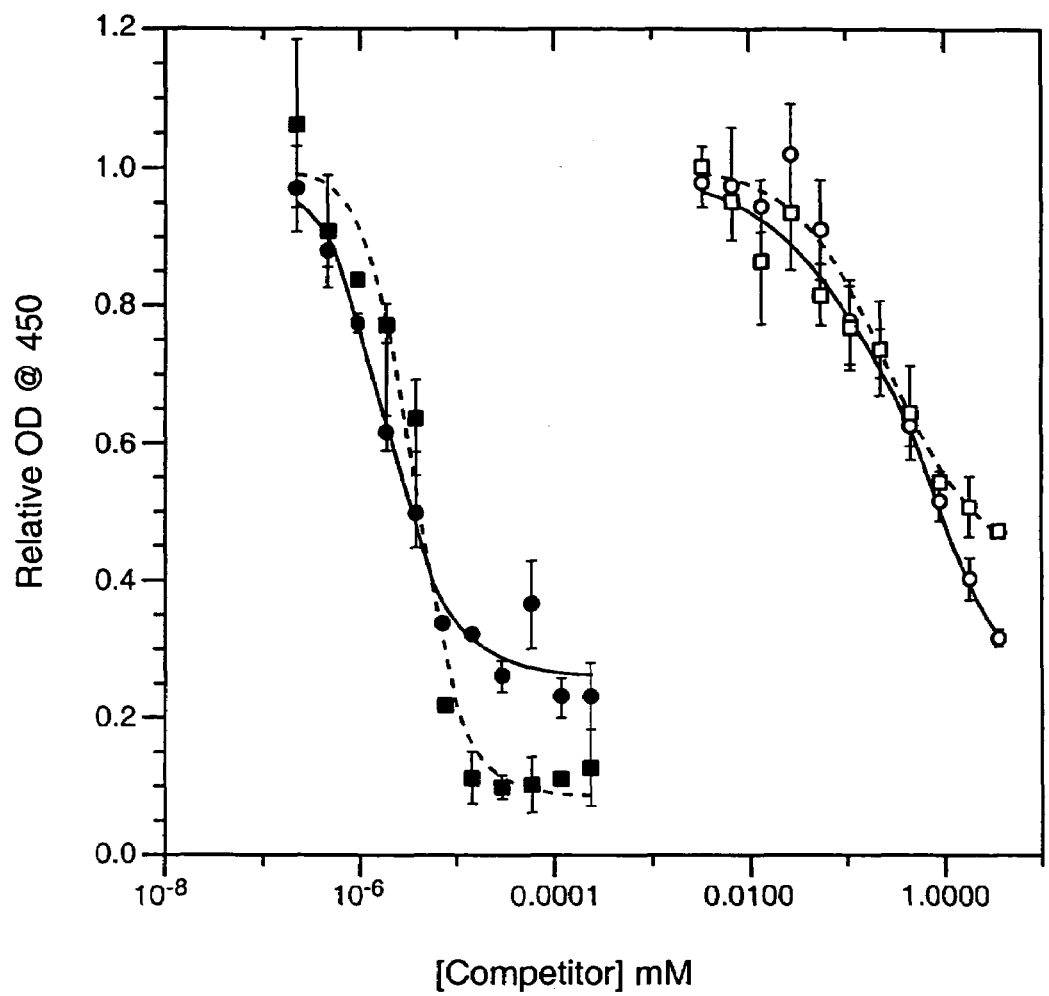
FIG._8

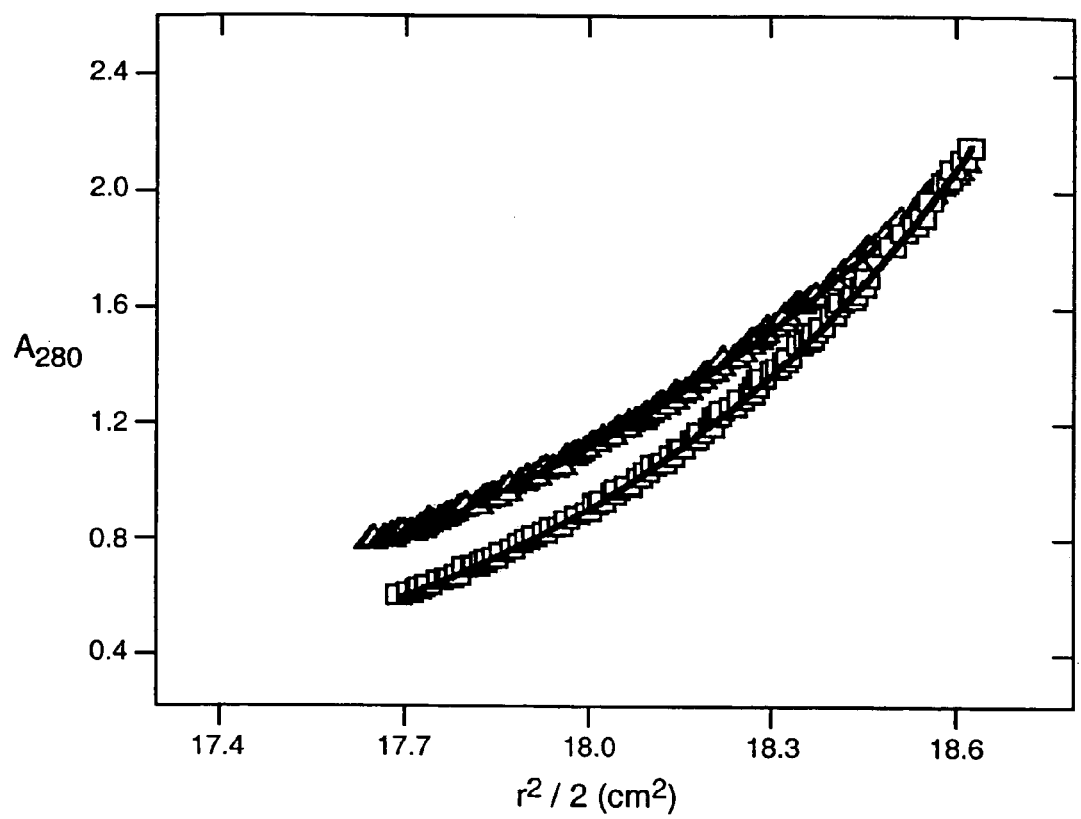
FIG._9A
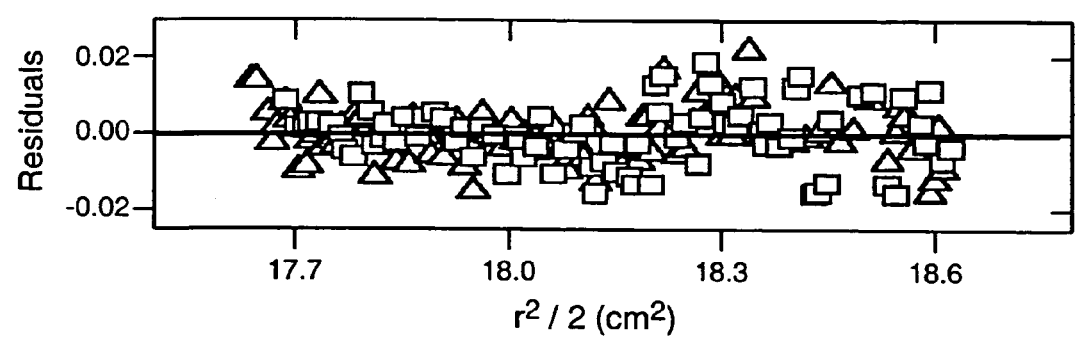
FIG._9B

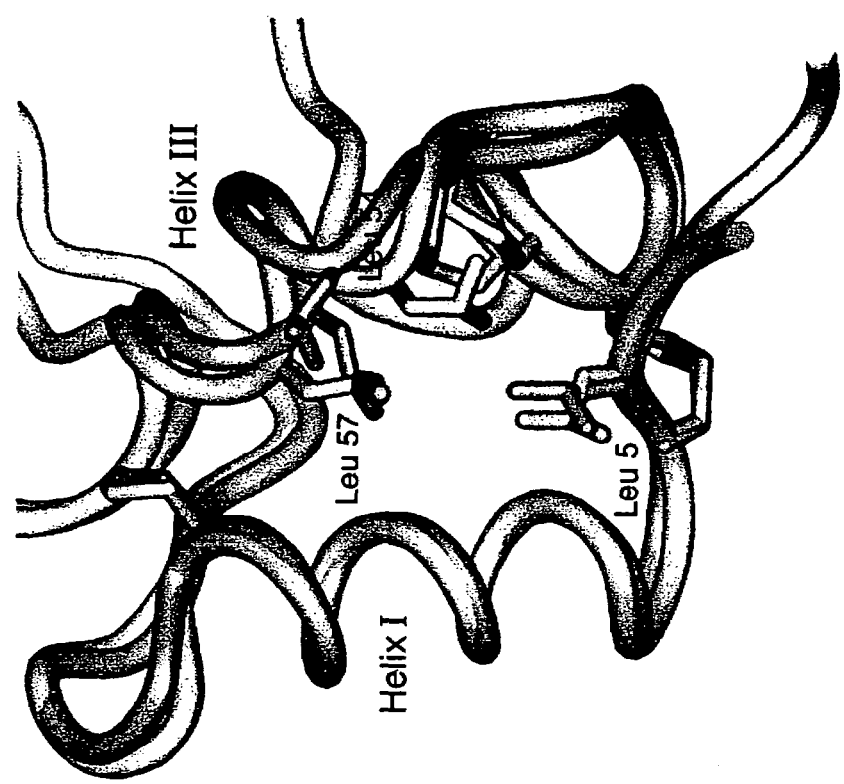
*FIG._10B*
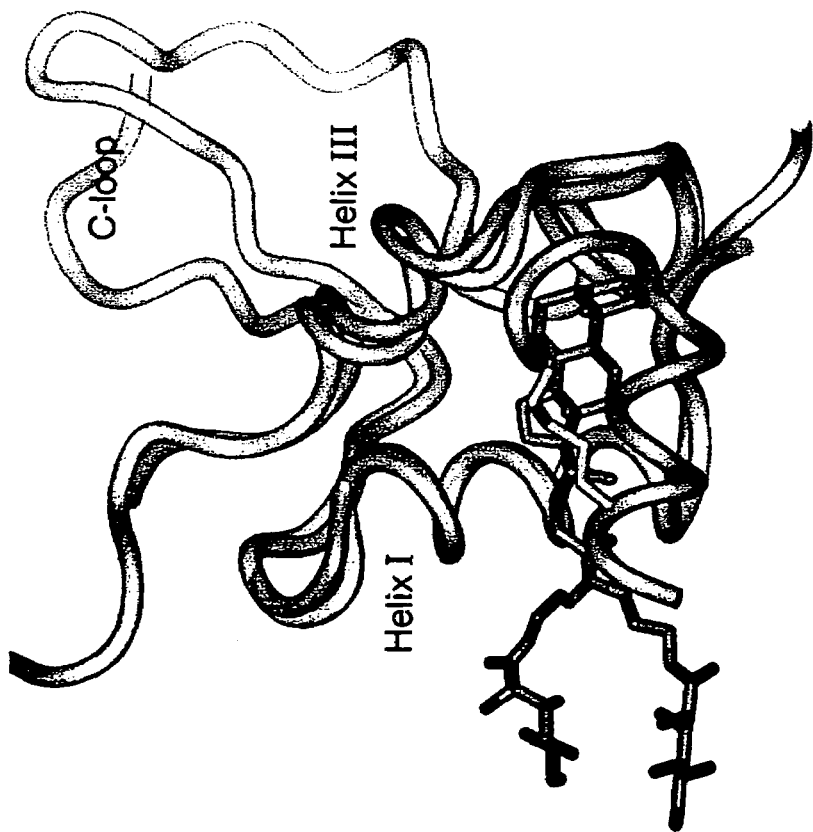
*FIG._10A*

CRYSTALLIZATION OF IGF-1

RELATED APPLICATIONS

This is a divisional application 1 claiming the benefit of the priority of application Ser. No. 10/066,009 filed on Feb. 1, 2002 now U.S. Pat. No. 7,084,240 under 35 U.S.C. 120, which is a non-provisional application filed under 37 CFR 1.53(b)(1), claiming priority under 35 USC 119(e) to provisional application No. 60/267,977 filed Feb. 9, 2001, and provisional application No. 60/287,072 filed Apr. 27, 2001, the contents of which are incorporated herein by reference.

BACKGROUND OF THE INVENTION

1. Field of the Invention

This invention is directed to a crystalline form of human insulin-like growth factor-1 (IGF-1) and more particularly to a crystal of human IGF-1, a method of crystallization thereof, and its structure, obtained by x-ray diffraction. In addition, the invention relates to methods of identifying new IGF-1 agonist molecules based on biophysical and biochemical data suggesting that a single detergent molecule that contacts residues known to be important for IGF-1 binding protein (IGFBP) interactions binds to IGF-1 specifically, and blocks binding of IGFBP-1 and IGFBP-3.

2. Description of Related Disclosures

There is a large body of literature on the actions and activities of IGFs (IGF-1, IGF-2, and IGF variants). Human IGF-1 is a serum protein of 70 amino acids and 7649 daltons with a pI of 8.4 (Rinderknecht and Humbel, *Proc. Natl. Acad. Sci. USA*, 73: 4379–4381 (1976); Rinderknecht and Humbel, *J. Biol. Chem.*, 253: 2769 (1978)) belonging to a family of somatomedins with insulin-like and mitogenic biological activities that modulate the action of growth hormone (GH) (Van Wyk et al., *Recent Prog. Horm. Res* 30: 259 (1974); Binoux, *Ann. Endocrinol.*, 41: 157 (1980); Clemmons and Van Wyk, *Handbook Exp. Pharmacol.*, 57: 161 (1981); Baxter, *Adv. Clin. Chem.*, 25: 49 (1986); U.S. Pat. No. 4,988,675; WO 91/03253; WO 93/2307 1). IGFs share a high sequence identity with insulin, being about 49% identical thereto. Unlike insulin, however, which is synthesized as a precursor protein containing a 33-amino-acid segment known as the C-peptide (which is excised to yield a covalently linked dimer of the remaining A and B chains), IGFs are single polypeptides (see FIG. 1).

In the developing embryo, the absence of IGF-1 leads to severe growth retardation that continues post-natally (Baker et al., *Cell*, 75: 73–82 (1993); Powell-Braxton et al., *Genes Dev.*, 7: 2609–2617 (1993); Liu et al., *Cell*, 75: 59–72 (1993); Liu et al., *Molecular Endocrinol.*, 12: 1452–1462 (1998)). While most (greater than 75%) of serum IGF-1 is produced by the liver in response to growth hormone, this liver-derived IGF-1 has been shown to be unnecessary for post-natal body growth in mice (Sjogren et al., *Proc. Natl. Acad. Sci. USA*, 96: 7088–7092 (1999)). Rather, it is the locally produced, non-hepatic IGF-1, acting in a paracrine/autocrine manner, which appears to be responsible for most of the post-natal growth-promoting effects of IGF-1 (Schlechter et al., *Proc. Natl. Acad. Sci. USA*, 83: 7932–7934 (1986); Isaksson et al., *Science*, 216: 1237–1239 (1982)). Consistent with its growth-promoting effects, IGF-1 is a powerful mitogen, regulating diverse cellular functions such as cell-cycle progression, apoptosis, and cellular differentiation (reviewed in Jones and Clemmons, *Endocr. Rev.*, 16: 3–34 (1995) and in LeRoith, *Endocrinology*, 141: 1287–1288 (2000)).

IGFs have been implicated in a variety of cellular functions and disease processes, including cell cycle progression, proliferation, differentiation, and insulin-like effects in insulin-resistant diabetes. Thus, IGF has been suggested as a therapeutic tool in a variety of diseases and injuries. Due to this range of activities, IGF-1 has been tested in mammals for such widely disparate uses as wound healing, treatment of kidney disorders, treatment of diabetes, reversal of whole-body catabolic states such as ADS-related wasting, treatment of heart conditions such as congestive heart failure, and treatment of neurological disorders (Guler et al., *Proc. Natl. Acad. Sci. USA*, 85: 4889–4893 (1988); Schalch et al., *J. Clin. Metab.*, 77 1563–1568 (1993); Froesch et al., *Horm. Res.*, 42: 66–71 (1994); Vlachopapadopoulou et al., *J. Clin. Endo. Metab.*, 12: 3715–3723 (1995); Saad et al., *Diabetologia*, 37 Abstract 40 (1994); Schoenle et al., *Diabetologia*, 34: 675–679 (1991); Morrow et al., *Diabetes*, 42 (Suppl.): 269 (1993) (abstract); Kuzuya et al., *Diabetes*, 24: 696–705 (1993); Schalch et al., "Short-term metabolic effects of recombinant human insulin-like growth factor I (rhIGF-I) in type II diabetes mellitus", in: Spencer E M, ed., *Modern Concepts of Insulin-like Growth Factors* (New York: Elsevier: 1991) pp. 705–713; Zenobi et al., *J. Clin. Invest.*, 90 2234–2241 (1992); Elahi et al., "Hemodynamic and metabolic responses to human insulin-like growth factor-1 (IGF-I) in men," in: *Modern Concepts of Insulin-Like Growth Factors*, Spencer, E M, ed. (Elsevier: New York, 1991), pp. 219–224; Quin et al., *New Engl. J. Med.*, 323: 1425–1426 (1990); Schalch et al., "Short-term metabolic effects of recombinant human insulin-like growth factor 1 (rhIGF-I) in type II diabetes mellitus," in: *Modem Concepts of Insulin-Like Growth Factors*, Spencer, E M, ed., (Elsevier: New York, 1991), pp. 705–713; Schoenle et al., *Diabetologia*, 34: 675–679 (1991); Usala et al., *N. Eng. J. Med.*, 327: 853–857 (1992); Lieberman et al., *J. Clin. Endo. Metab.*, 75: 30–36 (1992); Zenobi et al., *J. Clin. Invest.*, 90: 2234–2241 (1992); Zenobi et al., *J. Clin. Invest.*, 89: 1908–1913 (1992); Kerr et al., *J. Clin. Invest.*, 91: 141–147 (1993); Jabri et al., *Diabetes* 43: 369–374 (1994); Duerr et al., *J. Clin. Invest.*, 95: 619–627 (1995); Bondy, *Ann Intern. Med.*, 120: 593–601 (1994); Hammerman and Miller, *Am. J. Physiol.*, 265: F1–F14 (1993); Hammerman and Miller, *J. Am. Soc. Nephrol.*, 5: 1–11(1994); and Barinaga et al., *Science*, 264: 772–774 (1994)).

The patent literature also abounds with disclosures of various uses of IGF-1, or compounds that increase active concentration of IGF-1, to treat mammals, especially human patients, for example, U.S. Pat. Nos. 5,714,460; 5,273,961; 5,466,670; 5,126,324; 5,187,151; 5,202,119; 5,374,620; 5,106,832; 4,988,675; 5,106,832; 5,068,224; 5,093,317; 5,569,648; and 4,876,242; WO 92/11865; WO 96/01124; WO 91/03253; WO 93/25219; WO 93/08826; and WO 94/16722.

The IGF system is also composed of membrane-bound receptors for IGF-1, IGF-2, and insulin. The Type 1 IGF receptor (IGF-1R) is closely related to the insulin receptor in structure and shares some of its signaling pathways (Jones and Clemmons, supra). The IGF-2 receptor is a clearance receptor that appears not to transmit an intracellular signal (Jones and Clemmons, supra). Since IGF-1 and IGF-2 bind to IGF-1R with a much higher affinity than to the insulin receptor (Cascieri et al., *Biochemistry*, 27: 3229–3233 (1988)), it is most likely that most of the effects of IGF-1 and IGF-2 are mediated by IGF-1R (Humbel, *Eur. J. Biochem.* 190:445–462 (1990); Ballard et al., "Does IGF-1 ever act through the insulin receptor?", in Baxter et al. (Eds.), *The*

*Insulin-Like Growth Factors and Their Regulatory Proteins*, (Amsterdam: Elsevier, 1994), pp. 131–138).

IGF-1R is an α2β2 heterotetramer of disulfide-linked α and β subunits. αβ dimers are themselves disulfide linked on the cell surface to form a covalent heterotetramer. As in the insulin/insulin receptor complex, IGF-1 binds to the IGF-1R with a 1:2 stoichiometry (De Meyts, *Diabetologia,* 37: S135-S148 (1994)), with a high affinity site ($K_d$ about 0.4 nM) and a low affinity site ($K_d$ about 6 nM) (Tollefsen and Thompson, *J. Biol. Chem.*, 263: 16267–16273 (1988)). The x-ray crystal structure of the first three domains of IGF-1R has been determined (Garrett et al., *Nature,* 394, 395–399 (1998)). It contains three distinct domains (L1, Cys-rich, L2). Mutations that affect IGF-1 binding map to the concave surface of the receptor.

IGF-1R is a key factor in normal cell growth and development (Isaksson et al., *Endocrine Reviews,* 8: 426–438 (1987); Daughaday and Rotwein, *Endocrine Rev.,* 10:68–91 (1989)). Increasing evidence suggests, however, that IGF-1R signaling also plays a critical role in growth of tumor cells, cell transformation, and tumorigenesis (Baserga, *Cancer Res.,* 55:249–252 (1995)). Key examples include loss of metastatic phenotype of murine carcinoma cells by treatment with antisense RNA to the IGF-1R (Long et al., *Cancer Res.,* 55:1006–1009 (1995)) and the in vitro inhibition of human melanoma cell motility (Stracke et al., *J Biol. Chem.,* 264:21544–21549 (1989)) and of human breast cancer cell growth by the addition of IGF-1R antibodies (Rohlik et al., *Biochem. Biophys. Res. Commun.,* 149:276–281 (1987)).

The IGFs are potent breast cancer cell mitogens based on the observation that IGF-1 enhanced breast cancer cell proliferation in vitro (Cullen et al., *Cancer Res.,* 50:48–53 (1990)). Breast cancers express IGF-2 and IGF-1R, providing all the required effectors for an autocrine-loop-based proliferation paradigm (Quinn et al., *J. Biol. Chem.,* 271: 11477–11483 (1996); Steller et al., *Cancer Res.,* 56:1761–1765 (1996)). Because breast cancer is a common malignancy affecting approximately one in every eight women and is a leading cause of death from cancer in North American women (LeRoith et al., *Ann. Int. Med.,* 122:54–59 (1995)), new rational therapies are required for intervention. IGF-1 can suppress apoptosis, and therefore cells lacking IGF-1Rs or having compromised IGF-1R signaling pathways may give rise to tumor cells that selectively die via apoptosis (Long et al., *Cancer Res.,* 55:1006–1009 (1995)). Furthermore, it has recently become evident that alterations in IGF signaling in the context of other disease states, such as diabetes, may be responsible for exacerbating the complications of retinopathy (Smith et al., *Science,* 276:1706–1709 (1997)) and nephropathy (Horney et al., *Am. J. Physiol.* 274: F1045–F1053 (1998)).

IGF-1 in vivo is mostly found in complex with a family of at least six serum proteins known as IGFBPs (Jones and Clemmons, supra; Bach and Rechler, *Diabetes Reviews,* 3: 38–61 (1995)), that modulate access of the IGFs to the IGF-1R. They also regulate the concentrations of IGF-1 and IGF-2 in the circulation and at the level of the tissue IGF-1 R (Clemmons et al., *Anal. NY Acad. Sci. USA,* 692:10–21 (1993)). The IGFBPs bind IGF-1 and IGF-2 with varying affinities and specificities (Jones and Clemmons, supra; Bach and Rechler, supra). For example, IGFBP-3 binds IGF-1 and IGF-2 with a similar affinity, whereas IGFBP-2 and IGFBP-6 bind IGF-2 with a much higher affinity than they bind IGF-1 (Bach and Rechler, supra; Oh et al., *Endocrinology,* 132, 1337–1344 (1993)): The major carrier protein is IGFBP-3. Nothing is currently known about the stoichiometry of binding in these complexes of IGF-1 and its IGFBPs, due to the heterogeneous size of the complexes caused by glycosylation.

IGF-1 naturally occurs in human body fluids, for example, blood and human cerebral spinal fluid. Although IGF-1 is produced in many tissues, most circulating IGF-1 is believed to be synthesized in the liver. The IGFBPs are believed to modulate the biological activity of IGF-1 (Jones and Clemmons, supra), with IGFBP-1 (Lee et al., *Proc. Soc. Exp. Biol. & Med.,* 204: 4–29 (1993)) being implicated as the primary binding protein involved in glucose metabolism (Baxter, "Physiological roles of IGF binding proteins", in: Spencer (Ed.), *Modern Concepts of Insulin-like Growth Factors* (Elsevier, New York, 1991), pp. 371–380). IGFBP-1 production by the liver is regulated by nutritional status, with insulin directly suppressing its production (Suikkari et al., *J. Clin. Endocrinol. Metab.,* 66: 266–272 (1988)).

The function of IGFBP-1 in vivo is poorly understood. The administration of purified human IGFBP-1 to rats has been shown to cause an acute, but small, increase in blood glucose (Lewitt et al, *Endocrinology,* 129: 2254–2256 (1991)). The regulation of IGFBP-1 is somewhat better understood. It has been proposed (Lewitt and Baxter, *Mol. Cell Endocrinology,* 79: 147–152 (1991)) that when blood glucose rises and insulin is secreted, IGFBP-1 is suppressed, allowing a slow increase in "free" IGF-1 levels that might assist insulin action on glucose transport. Such a scenario places the function of IGFBP-1 as a direct regulator of blood glucose.

In most cases, addition of exogenous IGFBP blunts the effects of IGF-1. For example, the growth- stimulating effect of estradiol on the MCF-7 human breast cancer cells is associated with decreased IGFBP-3 mRNA and protein accumulation, while the anti-estrogen ICI 182780 causes growth inhibition and increased IGFBP-3 mRNA and protein levels (Huynh et al., *J Biol. Chem.,* 271: 1016–1021 (1996); Oh et al., *Prog. Growth Factor Res.,* 6:503–512 (1995)). It has also been reported that the in vitro inhibition of breast cancer cell proliferation by retinoic acid may involve altered IGFBP secretion by tumor cells or decreased circulating IGF-1 levels in vivo (LeRoith et al., *Ann. mt. Med.,* 122:54–59 (1995); Oh et al., (1995), supra). Contrary to this finding, treatment of MCF-7 cells with the anti-estrogen tamoxifen decreases IGF-1R signaling in a manner that is unrelated to decreased IGFBP production (Lee et al., *J Endocrinol.,* 152:39 (1997)). Additional support for the general anti-proliferative effects of the IGFBPs is the striking finding that IGFBP-3 is a target gene of the tumor suppressor, p53 (Buckbinder et al., *Nature,* 377:646–649 (1995)). This suggests that the suppressor activity of p53 is, in part, mediated by IGFBP-3 production and the consequential blockade of IGF action (Buckbinder et al., supra). These results indicate that the IGFBPs can block cell proliferation by modulating paracrine/autocrine processes regulated by IGF-1/IGF-2. A corollary to these observations is the finding that prostate-specific antigen (PSA) is an IGFBP-3-protease, which upon activation, increases the sensitivity of tumor cells to the actions of IGF-1 /IGF-2 due to the proteolytic inactivation of IGFBP-3 (Cohen et al., *J. Endocr.,* 142:407–415 (1994)). The IGFBPs complex with IGF-1/IGF-2 and interfere with the access of IGF-1/IGF-2 to IGF-1Rs (Clemmons et al., *Anal. NY Acad. Sci. USA,* 692:10–21 (1993)). IGFBP-1, -2 and -3 inhibit cell growth following addition to cells in vitro (Lee et al., *J Endocrinol.,* 152:39 (1997); Feyen et al., *J Biol. Chem.,* 266:19469–19474 (1991)). Further, IGFBP-1 (McGuire et al., *J Natl. Cancer Inst.,* 84:1336–1341(1992); Figueroa et al., *J Cell Physiol.*, 157:229–236 (1993)), IGFBP-3 (Oh et al. (1995), supra; Pratt and Pollak, *Biophys. Res. Commun.*, 198:292–297 (1994)) and IGFBP-2 have all been shown to inhibit IGF-1 or estrogen-induced breast cancer cell proliferation at nanomolar concentrations in vitro. These findings support the idea that the IGFBPs are potent antagonists of IGF action. There is also evidence for a direct effect of IGFBP-3 on cells through its own cell surface receptor, independent of IGF interactions (Oh et al., *J Biol. Chem.*, 268:14964–14971 (1993); Valentinis et al., *Mol. Endocrinol.*, 9:361–367 (1995)). Taken together, these findings underscore the importance of IGF and IGF-1R as targets for therapeutic use.

IGFs have mitogenic and anti-apoptotic influences on normal and transformed prostate epithelial cells (Hsing et al., *Cancer Research*, 56: 5146(1996); Culig et al., *Cancer Research*, 54: 5474(1994); Cohen et al., *Hormone and Metabolic Research*, 26:81 (1994); Iwamura et al., *Prostate*, 22:243 (1993); Cohen et al., *J. Clin. Endocrin. & Metabol.*, 73:401 (1991); Rajah et al., *J. Biol. Chem.*, 272: 12181 (1997)). Most circulating IGF-1 originates in the liver, but IGF bioactivity in tissues is related not only to levels of circulating IGFs and IGFBPs, but also to local production of IGFs, IGFBPs, and IGFBP proteases (Jones and Clemmons, supra). Person-to-person variability in levels of circulating IGF-1 and IGFBP-3 (the major circulating IGFBP (Jones and Clemmons, supra)) is considerable (Juul et al., *J. Clin. Endocrinol. & Metabol.*, 78: 744 (1994); Juul et al., *J. Clin. Endocrinol. & Metabol.*, 80: 2534 (1995)), and heterogeneity in serum IGF-1 levels appears to reflect heterogeneity in tissue IGF bioactivity. Markers relating to IGF-axis components can be used as a risk marker for prostate cancer, as PSA is likewise used (WO 99/38011).

Unlike most other growth factors, the IGFs are present in high concentrations in the circulation, but only a small fraction of the IGFs is not protein bound. For example, it is generally known that in humans or rodents, less than 1% of the IGFs in blood is in a "free" or unbound form (Juul et al., *Clin. Endocrinol.*, 44: 515–523 (1996); Hizuka et al., *Growth Regulation*, 1: 51–55 (1991); Hasegawa et al., *J. Clin. Endocrinol. Metab.*, 80: 3284–3286 (1995)). The overwhelming majority of the IGFs in blood circulate as part of a non-covalently associated ternary complex composed of IGF-1 or IGF-2, IGFBP-3, and a large protein termed the acid-labile subunit (ALS). The ternary complex of an IGF, IGFBP-3, and ALS has a molecular weight of approximately 150,000 daltons, and it has been suggested that the function of this complex in the circulation may be to serve as a reservoir and buffer for IGF-1 and IGF-2, preventing rapid changes in free IGF-1 or IGF-2.

There has been much work identifying the regions on IGF-1 and IGF-2 that bind to the IGFBPs (Bayne et al, *J. Biol. Chem.*, 265: 15648–15652 (1990); Dubaquie and Lowman, *Biochemistry*, 38: 6386–6396 (1999); and U.S. Pat. Nos. 5,077,276; 5,164,370; and 5,470,828). For example, it has been discovered that the N-terminal region of IGF-1 and IGF-2 is critical for binding to the IGFBPs (U.S. Pat. Nos. 5,077,276; 5,164,370; and 5,470,828). Thus, the natural IGF-1 variant, designated des (1-3) IGF-1, binds poorly to IGFBPs.

A similar amount of research has been devoted to identifying the regions on IGF-1 and IGF-2 that bind to IGF-1R (Bayne et al., supra; Oh et al., *Endocrinology* (1993), supra). It was found that the tyrosine residues in IGF-1 at positions 24, 31, and 60 are crucial to the binding of IGF-1 to IGF-1R (Bayne et al., supra). Mutant IGF-1 molecules where one or more of these tyrosine residues are substituted showed progressively reduced binding to IGF-1R. Bayne et al., supra, also investigated whether such mutants of IGF-1 could bind to IGF-1R and to the IGFBPs. They found that quite different residues on IGF-1 and IGF-2 are used to bind to the IGFBPs from those used to bind to IGF-1R. It is therefore possible to produce IGF variants that show reduced binding to the IGFBPs, but, because they bind well to IGF-1R, show maintained activity in in vitro activity assays.

Also reported was an IGF variant that binds to IGFBPs but not to IGF receptors and therefore shows reduced activity in in vitro activity assays (Bar et al., *Endocrinology*, 127: 3243–3245 (1990)). In this variant, designated (1–27, gly$^4$, 38–70)-hIGF-1, residues 28–37 of the C-region of human IGF-I (SEQ ID NO: 1) are replaced by a four-residue glycine bridge.

Other truncated IGF-1 variants are disclosed. For example, in the patent literature, WO 96/33216 describes a truncated variant having residues 1–69 of authentic IGF-1 (SEQ ID NO: 1). EP 742,228 discloses two-chain IGF-1 superagonists, which are derivatives of the naturally occurring, single-chain IGF-1 having an abbreviated C-region. The IGF-1 analogs are of the formula: BC", A wherein B is the B-region of IGF-1 or a functional analog thereof, C is the C- region of IGF-1 (SEQ ID NO: 1) or a functional analog thereof, n is the number of amino acids in the C-region and is from about 6 to about 12, and A is the A-region of IGF-1 or a functional analog thereof.

Additionally, Cascieri et al., *Biochemistry*, 27: 3229–3233 (1988) discloses four mutants of IGF-1 (SEQ ID NO: 1), three of which have reduced affinity to IGF-1R. These mutants are: (Phe$^{23}$, Phe$^{24}$, Tyr$^{25}$)IGF-1 (which is equipotent to human IGF-1 in its affinity to the Types 1 and 2 IGE and insulin receptors), (Leu$^{24}$)IGF-1 and (Ser$^{24}$)IGF-1 (which have a lower affinity than IGF-1 to the human placental IGF-1R, the placental insulin receptor, and the IGF-1R of rat and mouse cells), and desoctapeptide (Leu$^{24}$) IGF-1 (in which the loss of aromaticity at position 24 is combined with the deletion of the carboxyl-terminal D-region of hIGF-1 (SEQ ID NO: 1), which has lower affinity than (Leu24)IGF-1 for the IGF-1R and higher affinity for the insulin receptor). These four mutants have normal affinities for human serum binding proteins.

Bayne et al., *J. Biol. Chem.*, 263: 6233–6239 (1988) discloses four structural analogs of human IGF-1 (SEQ ID NO: 1): a B-chain mutant in which the first 16 amino acids of IGF-1 were replaced with the first 17 amino acids of the B-chain of insulin, (Gln$^3$, Ala$^4$)IGF-1, (Tyr$^{15}$, Leu$^{16}$)IGF-1, and (Gln$^3$, Ala$^4$, Tyr$^5$, Leu$^{16}$)IGF-1. These studies identify some of the regions of IGF-1 that are responsible for maintaining high-affinity binding with the serum binding protein and the Type 2 IGF receptor.

In another study, Bayne et al., *J. Biol. Chem.*, 264: 11004–11008 (1988) discloses three structural analogs of IGF-1 (SEQ ID) NO: 1): (1–62)IGF-1, which lacks the carboxyl-terminal 8-amino-acid D-region of IGF-1; (1–27, Gly$^4$, 38–70)IGF-1, in which residues 28–37 of the C-region of IGF-1 are replaced by a four-residue glycine bridge; and (1–27, Gly$^4$, 38–62)IGF-1, with a C-region glycine replacement and a D-region deletion. Peterkofsky et al., *Endocrinology*, 128: 1769–1779 (1991) discloses data using the Gly$^4$ mutant of Bayne et al., supra (vol. 264).

Cascieri et al., *J. Biol. Chem.*, 264: 2199–2202 (1989) discloses three IGF-1 analogs in which specific residues in the A-region of IGF-1 (SEQ ID NO: 1) are replaced with the corresponding residues in the A chain of insulin. The analogs are: (Ile$^{41}$, Glu$^{45}$, Gln$^{46}$, Thr$^{49}$, Ser$^{50}$, Ile$^{51}$, Ser$^{53}$, Tyr$^{55}$, Gln$^{56}$)IGF-1, an A-chain mutant in which residue 41 is changed from threonine to isoleucine and residues 42–56 of the A-region are replaced; (Thr$^{49}$, Ser$^{50}$,Ile$^{51}$)IGF-1; and (Tyr$^{55}$, Gln$^{56}$)IGF-1.

Clemmons et al., *J. Biol. Chem.*, 265: 12210–12216 (1990) discloses use of IGF-1 analogs that have reduced binding affinity for either IGF-1R or binding proteins to study the ligand specificity of IGFBP-1 and the role of IGFBP-1 in modulating the biological activity of IGF-1.

WO 94/04569 discloses a specific binding molecule, other than a natural IGFBP, that is capable of binding to IGF-1 and can enhance the biological activity of IGF-1.

Peptides that bind to IGFBP-1, block IGF-1 binding to this binding protein, and thereby release "free-IGF" activity from mixtures of IGF-1 and IGFBP-1 have been recently described (Lowman et al., *Biochemistry*, 37: 8870–8878 (1998); WO 98/45427 published Oct. 15, 1998; Lowman et al., International Pediatric Nephrology Association, Fifth Symposium on Growth and Development in Children with Chronic Renal Failure (New York, Mar. 13, 1999)). Also described is the natural molecule, des(1-3)IGF-1, which shows selectively reduced affinity for some of the IGF binding proteins, yet a maintained affinity for the IGF receptor (U.S. Pat. Nos. 5,077,276; 5,164,370; 5,470,828).

Exploitation of the interaction between IGF and IGFBP in screening, preventing, or treating disease has been limited, however, because of a lack of specific antagonists. To date, only one publication is known to exist that describes the application of an IGF-1/IGF-2 antagonist as a potential therapeutic adjunct in the treatment of cancer (Pietrzkowski et al., *Cancer Res.*, 52: 6447-6451 (1992)). In that report, a peptide corresponding to the D-region of IGF-1 was synthesized for use as an IGF-1/2 antagonist. This peptide exhibited questionable inhibitory activity against IGF-1. The basis for the observed inhibition is unclear, as the D-region does not play a significant role in IGF-1R binding but rather, in IGF-1 binding to the insulin receptor (Cooke et al., *Biochem.*, 30:5484–5491 (1991); Bayne et al., supra (Vol. 264); Yee et al., *Cell Growth and Different.*, 5:73–77 (1994)).

WO 00/23469 discloses the portions of IGFBP and IGF peptides that account for IGF-IGFBP binding, i.e., an isolated IGF binding domain of an IGFBP or modification thereof that binds IGF with at least about the same binding affinity as the full-length IGFBP. The patent publication also discloses an IGF antagonist that reduces binding of IGF to an IGF receptor, and/or binds to a binding domain of IGFBP.

Additionally, WO 93/23067 discloses pharmaceutical compositions comprising short peptides that function as IGF-1 receptor antagonists. The peptides used in the pharmaceutical compositions consist of less than 25 amino acids, comprise at least a portion of the C- or D-region from IGF-1, and inhibit IGF-1-induced autophosphorylation of IGE-1 receptors.

Polypeptides, including the IGF molecules, have a three-dimensional structure determined by the primary amino acid sequence and the environment surrounding the polypeptide. This three-dimensional structure establishes the activity, stability, binding affinity, binding specificity, and other biochemical attributes of the polypeptide. Thus, knowledge of the three-dimensional structure of a protein can provide much guidance in designing agents that mimic, inhibit, or improve its biological activity in soluble or membrane-bound forms.

The three-dimensional structure of a polypeptide may be determined in a number of ways. Many of the most precise methods employ x-ray crystallography (Van Holde, *Physical Biochemistry* (Prentice Hall: N.J., 1971), pp. 221–239). This technique relies on the ability of crystalline lattices to diffract x-ray or other forms of radiation. Diffraction experiments suitable for determining the three-dimensional structure of macromolecules typically require high-quality crystals. Unfortunately, such crystals have been unavailable for IGF-1 as well as many other proteins of interest. Crystals have been described for M-CSF (EP 668,914B1), CD40 ligand (WO 97/00895), and a BC2 Fab fragment (WO 99/01476), for example.

The crystallization of insulin is an intensively researched field, both with respect to work on structural analysis (Adams et al., *Nature*, 224:491 (1969)) and pharmaceutical applications. Examples of insulin crystal suspensions that are used therapeutically include suspensions of rhombohedral zinc-insulin crystals that are stable in the presence of 0.8 to 2.5% of zinc (based on the weight of insulin) at a neutral pH value and exhibit a delayed action, and isophane insulin protamine crystals, which are used in delayed action products in the form of small rods. A few other crystal modifications of insulin are furthermore known, but these have hitherto been of interest only for X-ray structure analysis. Thus, zinc-free orthorhombic and monoclinic crystals have been obtained under acid pH conditions (Einstein and Low, *Acta Crystallogr.*, 15: 32–34 (1962)). Smaller rhombic dodecahedra, which are to be classified in the cubic space group, have been obtained at the isoelectric point, also in the absence of zinc. Finally, a monoclinic crystal form of insulin has been obtained above the isoelectric point in the presence of zinc and in the presence of phenol or phenol derivatives. These crystals grow to a considerable size (up to 3 mm) within a few days and have sharp edges. Interestingly, these crystals have been found only on glass surfaces and not on the free surface of the solution. Crystal suspensions and other crystal forms of insulin preparations and insulin analogs are described, for example, in such representative patents as U.S. Pat. Nos. 4,959,351; 5,840,680; 5,834,422; 6,127,334; 5,952,297; 5,650,486; 5,898,028; 5,898,067; 5,948,751; 5,747,642; 5,597,893; 5,547,930; 5,534,488; 5,504,188; 5,461,031; and 5,028,587.

Various methods for preparing crystalline proteins and polypeptides are known in the an (McPherson et al., "Preparation and Analysis of Protein Crystals," McPherson (Robert E. Krieger Publishing Company, Malabar, Fla., 1989); Weber, Advances in Protein Chemistry, 41: 1–36 (1991); U.S. Pat. Nos. 4,672,108 and 4,833,233). Although there are multiple approaches to crystallizing polypeptides, no single set of conditions provides a reasonable expectation of success, especially when the crystals must be suitable for x-ray diffraction studies. Significant effort is required to obtain crystals of sufficient size and resolution to provide accurate information regarding the structure. For example, once a protein of sufficient purity is obtained, it must be crystallized to a size and clarity that is useful for x-ray diffraction and subsequent structure resolution. Further, although the amino acid sequence of a target protein may be known, this sequence information does not allow an accurate prediction of the crystal structure of the protein. Nor does the sequence information afford an understanding of the structural, conformational, and chemical interactions between a ligand such as an IGFBP and its protein target. Thus, although crystal structures can provide a wealth of valuable information in the field of drug design and discovery, crystals of certain biologically relevant compounds such as IGF-1 are not readily available to those skilled in the art. High-quality, diffracting crystals of IGF-1 would assist the determination of its three-dimensional structure.

Generation of specific IGF-1 antagonists has been restricted, at least in part, because of difficulties in studying the structure of IGF and IGFBPs. Due to the inability to obtain crystals of IGF-1 suitable for diffraction studies, for example, an extrapolation of IGF-1 structure based on the crystal structure of porcine insulin was the most important structural road map for IGF-1 available (Blundell et al., *Proc. Natl. Acad. Sci. USA,* 75:180–184 (1978)). See also Blundell et al., *Fed. Proc.,* 42: 2592–2597 (1983), which discloses tertiary structures, receptor binding, and antigenicity of IGFs. Based on studies of chemically modified and mutated IGF-1, a number of common residues between IGF-1 and insulin have been identified as being part of the IGF-1R-insulin receptor contact site, in particular, the aromatic residues at positions 23–25.

Using NMR and restrained molecular dynamics, the solution structure of IGF-1 was recently reported (Cooke et al., supra). The resulting minimized structure was shown to better fit the experimental findings on modified IGF-1, as well as the extrapolations made from the structure-activity studies of insulin. Further, De Wolf et al, *Protein Sci.,* 5: 2193–2202 (1996) discloses the solution structure of a mini-IGF-1. Sato et al., *Int. J. Pept. Protein Res.,* 41: 433–440 (1993) discloses the three-dimensional structure of IGF-1 determined by 1H-NMR and distance geometry. Laajoki et al., *J. Biol. Chem.,* 275: 10009–10015 (2000) discloses the solution structure and backbone dynamics of long-[Arg(3)]IGF-1. See also Laajoki et al., *FEBS Lett.,* 420: 97–102 (1997)). The small number of NMR models available for IGF-1 are not very well defined, as there are large RMSDs between the backbone atoms of the helical segments. The best NMR model is of IGF-2 in which three alpha-helices are shown. See Torres et al., *J. Mol. Biol.,* 248: 385–401 (1995), which discloses the solution structure of human IGF-2 and its relationship to receptor and binding protein interactions. In all structures, the C- and D-regions are very poorly defined.

In addition to providing structural information, crystalline polypeptides provide other advantages. For example, the crystallization process itself further purifies the polypeptide and satisfies one of the classical criteria for homogeneity. In fact, crystallization frequently provides unparalleled purification quality, removing impurities that are not removed by other purification methods such as HPLC, dialysis, conventional column chromatography, etc. Moreover, crystalline polypeptides are often stable at ambient temperatures and free of protease contamination and other degradation associated with solution storage. Crystalline polypeptides may also be useful as pharmaceutical preparations. Finally, crystallization techniques in general are largely free of problems such as denaturation associated with other stabilization methods (e.g. lyophilization). Thus, there exists a significant need for preparing IGF-1 compositions in crystalline form and determining their three-dimensional structure. The present invention fulfills this and other needs. Once crystallization has been accomplished, crystallographic data provides useful structural information that may assist the design of peptides that may serve as agonists or antagonists. In addition, the crystal structure provides information useful to map the receptor-binding domain, which could then be mimicked by a small non-peptide molecule that may serve as an antagonist or agonist. Also, findings regarding the detergent's inhibition of the binding of IGFBP to IGF-1 can be used to identify new IGF-1 agonists.

SUMMARY OF THE INVENTION

Accordingly, the invention is as claimed. IGF-1 has been crystallized and its structure determined using multiwavelength anomalous diffraction (MAD) at 1.8 angstroms resolution by exploiting the anomalous scattering of a single bromide ion and six of the seven sulfur atoms of IGF-1. The C-region of IGF-1, which is ordered in the crystal structure, forms a type II beta-turn and mediates a crystal packing interaction across a crystallographic dyad. The solution state of IGF-1 was characterized by analytical ultracentrifugation, and the results indicate that IGF-1 exists primarily as a monomer at neutral pH, with only a slight tendency to dimerize at millimolar concentrations. A molecule of detergent, N,N-bis(3-D-gluconamidopropyl)-deoxycholamine (deoxy big CHAPS), mediates a crystal packing contact between symmetry-related molecules. Biophysical and biochemical data show that the N,N-bis(3-D-gluconamidopropyl)-deoxycholamine binds to IGF-1 specifically and blocks binding of IGFBP-1 and IGFBP-3.

Accordingly, in one aspect, the invention provides a crystal formed by IGF-1 that diffracts x-ray radiation to produce a diffraction pattern representing the three-dimensional structure of the IGF-1. Preferably this crystal has approximately the following cell constants a=31.831 Å, b=71.055 Å, c=65.995 Å, and a space group of $C222_1$. Also preferably, the IGF-1 contains an A-, B-, C-, and D-region and forms a dimer in the crystal, and further preferred is the crystal comprising a receptor binding site at the dimer interface.

The invention also provides a composition comprising the above crystal. Preferably in this composition the IGF-1 is biologically active when resolubilized. The invention further provides a method of treating a mammal suffering from an agonist disorder, preferably a human patient, said method comprising administering to said mammal an effective amount of the above resolubilized composition.

The invention also provides a method of crystallizing IGF-1 comprising the steps of:

(a) mixing an aqueous solution comprising IGF-1 with a reservoir solution comprising a precipitant to form a mixed volume; and (b) crystallizing the mixed volume.

The invention also provides crystalline IGF-1 produced by the above method.

Additionally, the invention provides a method for determining a three-dimensional structure of IGF-1 comprising:

(a) crystallizing the IGF-1;

(b) irradiating the crystalline IGF-1 to obtain a diffraction pattern characteristic of the crystalline IGF-1; and (c) transforming the diffraction pattern into the three-dimensional structure of the IGF-1. Further, the invention provides a machine-readable data storage medium comprising a data storage material encoded with machine-readable data that, when read by an appropriate machine, displays a three-dimensional representation of a crystal of a molecule comprising IGF-1.

In further aspects, the invention provides an IGF-1 crystal with the structural coordinates shown in Appendix 1.

Additionally, the invention provides a method of using a three-dimensional structure of IGF-1 derived from an IGF-1 crystal wherein the three-dimensional structure of IGF-1 includes an IGF-1 receptor-binding region, the method comprising identifying compounds having structures that interact with the receptor-binding region of the three-dimensional structure of IGF-1 and function as an IGF-1 agonist or antagonist. Preferably in such method the three-dimensional structure of IGF-1 includes alpha-carbon coordinates substantially the same as those of the structural information presented in Appendix 1.

In another aspect, the invention provides a method of identifying IGF-1 agonists or antagonists comprising the steps of:
(a) crystallizing IGF-1 to form IGF-1 crystals, the IGF-1 crystals containing a group of amino acid residues defining an IGF-1 receptor-binding region;
(b) irradiating the IGF-1 crystals from step (a) to obtain a diffraction pattern of the IGF-1 crystals;
(c) determining a three-dimensional structure of IGF-1 from the diffraction pattern, the structure including an IGF-1 receptor-binding region; and
(d) identifying an IGF-1 agonist or antagonist having a three-dimensional structure that functionally duplicates essential IGF receptor-binding, solvent-accessible residues presenting the three-dimensional structure of the IGF-1 receptor-binding region, said IGF-1 agonist or antagonist having altered signal transduction capacity to IGF-1-responsive cells, as compared to IGF-1.

Preferably, in this method the solvent-accessible residues do not participate in formation of the IGF-1 interface.

According to certain further aspects, the invention includes a method of designing a compound, such as a peptidomimetic, that mimics the 3-dimensional surface structure of IGF-1 comprising the steps of:
(a) determining the 3-dimensional structure of the IGF-1; and
(b) designing a compound that mimics the 3-dimensional surface structure of the IGF-1.

According to a further embodiment, the invention provides a method for identifying a peptidomimetic that binds IGF-1 and blocks binding of an IGFBP or a receptor that binds to IGF-1 comprising the steps of:
(a) searching a molecular structure database with the structural parameters or structural coordinates provided in Appendix 1; and
(b) selecting a molecule from the database that mimics the structural parameters or structural coordinates of the IGF-1.

The invention also provides a method for determining at least a portion of a three-dimensional structure of a molecular complex, said complex comprising IGF-1 and said method comprising the steps of:
(a) determining the structural coordinates of a crystal of IGF-1;
(b) calculating phases from the structural coordinates;
(c) calculating an electron density map from the phases obtained in step (b); and
(d) determining the structure of at least a portion of the complex based on said electron density map.

Preferably the structural coordinates used in step (a) are substantially the same as those described in Appendix 1 or describe substantially the same crystal as the coordinates in Appendix 1.

The invention also provides a method for evaluating the ability of a chemical entity to associate with IGF-1 or a complex thereof, the method comprising the steps of:
(a) employing computational or experimental means to perform a fitting operation between the chemical entity and the IGF-1 or complex thereof, thereby obtaining data related to the association; and
(b) analyzing the data obtained in step (a) to determine the characteristics of the association between the chemical entity and the IGF-1 or complex thereof.

The invention also provides a chemical entity identified by the above method that interferes with the in vivo or in vitro association between IGF-1 and its receptor or between IGF-1 and at least one of its binding proteins, or associates with a binding site on IGF-1.

Also provided is a heavy-atom derivative of a crystallized form of IGF-1.

The invention also comprises a method of computationally or experimentally evaluating a chemical entity to obtain information about its association with one or more binding sites of IGF-1 using a crystal of IGF-1 having the structural coordinates described in Appendix 1.

Any peptide analogs and other chemical entities identified using the above methods of the present invention are useful in the therapeutic methods described herein and as pharmaceutical compositions.

The invention also provides a method of identifying indirect agonists of IGF-1 comprising the steps of:
(a) comparing the ability of N,N-bis(3-D-gluconamidopropyl)-deoxycholamine to inhibit binding of IGFBP-1 or IGFBP-3 to IGF-1 with the ability of a candidate indirect agonist of IGF-1 to so inhibit binding; and
(b) determining whether the candidate agonist inhibits such binding at least as well as N,N-bis(3-D-gluconamidopropyl)-deoxycholamine.

In a preferred embodiment, the comparison is accomplished by competition assay between N,N-bis(3-D-gluconamidopropyl)-deoxycholamine and the candidate agonist. In a more preferred embodiment, inhibition of binding is measured by pre-incubating N,N-bis(3-D-gluconamidopropyl)-deoxycholamine or the candidate agonist with IGF-1 expressed on bacteriophage particles and measuring residual binding of IGF-1 to IGFBP-1 or IGFBP-3 in a plate-based ELISA assay.

The invention further provides a method of identifying indirect agonists of IGF-1 comprising co-crystallizing a candidate indirect agonist of IGF-1 with IGF-1 to form a co crystalline structure and determining if the candidate agonist binds to one or both of two patches on IGF-1 (SEQ ID NO: 1), wherein one patch has the amino acid residues Glu 3, Thr 4, Leu 5, Asp 12, Ala 13, Phe 16, Val 17, Cys 47, Ser 51, Cys 52, Asp 53, Leu 54, and Leu 57, second patch has the amino acid residues Val 11, Gln 15, Phe 23, Phe 25, Asn 26, Val 44, Phe 49, and Arg 55, and wherein binding occurs if there is at least one contact between each listed amino acid residue of a given patch and the candidate agonist that is less than or equal to 6 angstroms in the co-crystalline structure. In preferred embodiments, the candidate agonist inhibits binding of IGFBP-1 or -3 to IGF-1 (SEQ ID NO: 1) at least as well as N, N-bis(3-D-gluconamidopropyl)-deoxycholamine. More preferred is the method wherein inhibition of binding is measured using a competition assay between N, N-bis(3-D-gluconamidopropyl)- deoxycholamine and the candidate agonist. Most preferred is the method wherein inhibition of binding is measured by pre-incubating N, N-bis(3-D-gluconamidopropyl)-deoxycholamine or the candidate agonist with IGF-1 expressed on bacteriophage particles and measuring residual binding of IGF-1 to IGFBP-1 or IGFBP-3 in a plate-based ELISA assay.

Also provided herein is a method for treating an IGF-1 agonist disorder in a mammal comprising administering to the mammal an effective amount of N,N-bis(3-D-gluconamidopropyl)-deoxycholamine.

Further provided herein is a co-crystalline complex of IGF-1 and N,N-bis(3-D-gluconamidopropyl)-deoxycholamine.

BRIEF DESCRIPTION OF THE DRAWINGS

FIG. 1 aligns the sequences of IGF-1 (SEQ ID NO:1), IGF-2 (SEQ ID NO:2), and insulin (SEQ ID NO:3). The A-, B-, and C-chains of insulin (and the sequences of IGF-1 and IGF-2 corresponding thereto) are shown respectively in bold, underlined, and italicized text. The three aromatic residues are shown by outlining the text. The residues marked with a (!) have been demonstrated to be important for binding to the IGF-1 receptor. The residues marked with a "*" have been shown to be important for binding to IGFBP-1 and IGFBP-3. The carboxyl-terminal residues comprising the D-region of IGF-1 and IGF-2 are depicted in regular type.

FIG. 2 is a ribbon diagram of IGF-1 showing the backbone fold. In the Ramachandran plot, 97.7% is most favored and 2.3% is allowed.

FIG. 3 is a ribbon diagram of both IGF-1 (left structure) and insulin (right structure).

FIG. 4 is a ribbon diagram of IGF-1 showing that the detergent used in the reservoir solution, (N,N-bis(3-D-gluconamidopropyl)-deoxycholamine), binds into a small hydrophilic cleft at the base of the B-helix. The detergent is represented by lighter gray structures than the IGF-1 structures.

FIG. 5 is a ribbon diagram of IGF-1 as a dimer, with the detergent shown in lighter gray.

FIG. 6 is a ribbon diagram of IGF-1 as a dimer, showing that the residues important for receptor binding (indicated by ring structures in the center portion of the figure) cluster at the dimer interface. The detergent is shown in lighter gray at the outer portions of the figure.

FIGS. 7A and 7B are ribbon diagrams of IGF-1 (SEQ ID NO: 1) demonstrating, as does FIG. 4, that the detergent used in the reservoir solution (N,N-bis(3-D-gluconamidopropyl)-deoxycholamine), shown in stick form, binds into a small hydrophilic cleft at the base of the B-helix. In FIG. 7A the detergent head group is inserted into the cleft lined by residues Leu 5, Phe 16, Val 17, Leu 54, and Leu 57 of SEQ ID NO: 1. The various shades of gray are according to the alanine-scanning mutagenesis results of Dubaquie and Lowman, supra, with the Phe 16, Val 17, and Leu 5 regions indicating a 5–10 fold reduction, the Glu 3 region a 10–100 fold reduction, and the Pro 63 and Pro 63' regions a >100 fold reduction in affinity for IGFBP-1 where the amino acid residues are numbered with reference to the amino acid sequence of IGF-1 (SEQ ID NO:1). The black part at the far right corresponds to the symmetry-related IGF-1 molecule that forms the crystallographic dimer. The circle near Leu 54 indicates the C10 atom of the detergent, which differs from another detergent (3-((3-cholamidopropyl) dimethylammonio)-1-propane sulphonate; or CHAPS) by having a hydroxyl group at this position. FIG. 7B shows the view from the opposite surface of the detergent and depicts the interactions of the detergent molecule with a symmetry-related IGF-1 molecule. As in FIG. 7A the various shades of gray are according to the alanine-scanning mutagenesis results of Dubaquie and Lowman, supra, with the group near Gln 15 indicating a 5–10 fold reduction, the far left medium gray molecules, the Leu 10 region molecules, and the far right medium gray region indicating a 10–100 fold reduction, and the black regions at Phe 49 and Gly 7 indicating a >100 fold reduction in affinity for IGFBP-1. The black regions to the right of the detergent molecule correspond to the symmetry-related IGF-1 molecule that forms the crystallographic dimer. The circle near Gln 15 indicates the C10 atom of the detergent, as noted above for FIG. 7A. This figure was prepared using the program INSIGHT (MSI, San Diego, Calif.).

FIG. 8 shows a graph resulting from a detergent/IGFBP competition binding study. In this experiment, N,N-bis(3-D-gluconamidopropyl)-deoxycholamine was used as a competitive inhibitor of IGF-1 binding to immobilized IGFBP-1 (open circles) or IGFBP-3 (open squares). As a positive control, soluble IGFBP-1 (solid circles) or IGFBP-3 (solid squares) was used as a competitive inhibitor of IGF-1 binding to immobilized IGFBP-1 or IGFBP-3, respectively. Each data point represents the average of three independent experiments.

FIG. 9A shows a non-linear least-squares analysis of sedimentation equilibrium data for IGF-1 in solution. Data collected at rotor speeds of 30,000 rpm (open triangles) and 35,000 rpm (open squares) were fit as an ideal monomer-dimer self-association model. The solid lines are the fits of the data. FIG. 9B shows the residuals plotted for both rotor speeds after accounting for the data by the fitting procedure. They are randomly distributed around zero, indicating that the monomer-dimer model is correct for this interaction.

FIG. 10A shows a ribbon diagram determined by NMR of a complex of IGF-1 and N,N-bis(3-D-gluconamidopropyl)-deoxycholamine), and FIG. 10B shows a ribbon diagram determined by NMR of a complex of IGF-1 bound to a phage-derived IGF-1 antagonist peptide designated IGF-F1-1.

DESCRIPTION OF THE PREFERRED EMBODIMENTS

A. DEFINITIONS

As used herein, "IGF-1" refers to human insulin-like growth factor-1 unless otherwise noted, and has the human native mature IGF-1 sequence without a N-terminal methionine, as described, for example, by EP 230,869 published Aug. 5, 1987; EP 128,733 published Dec. 19, 1984; or EP 288,451 published Oct. 26, 1988.

An "IGFBP" or an "IGF binding protein" refers to a protein or polypeptide normally associated with or bound or complexed to IGF-1, whether or not it is circulatory (i.e., in serum or tissue). This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., *Proc. Natl. Acad. Sci. USA,* 92: 4472–4476(1995) and Oh et al., *J. Biol. Chem.,* 271: 30322–30325(1996). PSF is described in Yamauchi et al., *Biochemical Journal,* 303: 591–598 (1994). ESM-1 is described in Lassalle et al., *J. Biol. Chem.,* 271: 20458–20464 (1996). For other identified IGFBPs, see, e.g., EP 375,438 published 27 Jun. 1990; EP 369,943 published 23 May 1990; U.S. Pat. No. 5,258,287; WO 89/09268 published 5 Oct. 1989; Wood et al., *Molecular Endocrinology,* 2: 1176–1185 (1988); Brinkman et al., *The EMBO J.,* 7: 2417–2423 (1988); Lee et al., *Mol. Endocrinol.,* 2: 404–411 (1988); Brewer et al., *BBRC,* 152: 1289–1297 (1988); EP 294,021 published 7 Dec. 1988; Baxter et al., *BBRC,* 147: 408–415 (1987); Leung et al., *Nature,* 330: 537–543 (1987); Martin et al., *J. Biol. Chem.,* 261: 8754–8760 (1986); Baxter et al., *Comp. Biochem. Physiol.,* 91B: 229–235 (1988); WO 89/08667 published 21 Sep. 1989; WO 89/09792 published 19 Oct. 1989; and Binkert et al., *EMBO J.,* 8: 2497–2502 (1989). IGFBP-1 and IGFBP-3 bind to different residues of IGF-1.

As used herein, "human IGF-1 receptor" or just "IGF-1 receptor" refers to any receptor for IGF-1 found in humans and includes the Type 1 and Type 2 IGF receptors in humans to which human IGF-1 binds, such as the placental IGF-1R, etc.

An "indirect agonist of IGF-1" is a molecule that releases IGF-1 in situ from IGFBP-3 or IGFBP-1 so that the IGF-1 released is active and interacts with its receptor.

"Peptides" are molecules having at least two amino acids and include polypeptides having at least about 60 amino acids. Preferably, the peptides have about 10 to about 60 amino acids, more preferably about 10–25, and most preferably about 12–25 amino acids. The definition includes linear and cyclic peptides, peptide derivatives, their salts, or optical isomers.

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human. The term "non-adult" refers to mammals that are from perinatal age (such as low-birth-weight infants) up to the age of puberty, the latter being those that have not yet reached full growth potential.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented.

A "disorder" is any condition that would benefit from treatment with an IGF-1 agonist ("agonist disorder") or antagonist ("antagonist disorder"). This includes chronic and acute disorders or diseases including those pathological conditions that predispose the mammal to the disorder in question. The disorder being treated may be a combination of two or more of the agonist or antagonist disorders listed below.

Non-limiting examples of antagonist disorders include benign and malignant tumors, leukemias and lymphoid malignancies, neuronal, glial, astrocytal, hypothalamic and other glandular, macrophagal, epithelial, stromal and blastocoelic disorders, and inflammatory, angiogenic and immunologic disorders, diabetic complications such as diabetic retinopathies or neuropathies, age-related macular degeneration, ophthalmic surgery such as cataract extraction, a corneal transplant, glaucoma filtration surgery and keratoplasty, surgery to correct refraction, i.e., a radial keratotomy, also in sclera macular holes and degeneration, retinal tears, vitreoretinopathy, miscellaneous disorders, cataract disorders of the cornea such as the sequelae of radial keratotomy, dry eye, viral conjunctivitis, ulcerative conjunctivitis, wounds such as corneal epithelial wounds, Sjogren's syndrome, retinal disorders such as macular and retinal edema, vision-limited scarring, retinal ischemia, and proliferative vitreous retinopathy.

More preferably, such antagonist disorders include diabetic complications exacerbated by IGF-1, ischemic injury, and diseases associated with undesirable cell proliferation such as cancer, restenosis, and asthma. If the disorder is a diabetic complication exacerbated by IGF-1, such complication can include diabetic retinopathy or diabetic nephropathy. The efficacy of the treatment can be evidenced by a reduction in clinical manifestations or symptoms, including, for example, improved renal clearance, improved vision, or a reduction in the amount of IGF-1 available for binding to an IGF-1 receptor. If the disorder is an ischemic injury, it can include strokes, myocardial ischemia, and ischemic injury to the kidneys.

Examples of agonist disorders for purposes herein include any condition that would benefit from treatment with an IGF-1, including but not limited to, for example, lung diseases, hyperglycemic disorders as set forth below, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-insufficiency, Turner's syndrome, Laron's syndrome, short stature, undesirable symptoms associated with aging such as obesity and increased fat mass-to-lean ratios, immunological disorders such as immunodeficiencies including decreased CD4 counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., peripheral neuropathy, multiple sclerosis, muscular dystrophy, or myotonic dystrophy, and catabolic states associated with wasting caused by any condition, including, e.g., trauma or wounding, or infection such as with a bacterium or human virus such as HIV, wounds, skin disorders, gut structure and function that need restoration, and so forth. The preferred agonist disorders targeted for treatment herein are diabetes and obesity, heart dysfunctions, AIDS-related wasting, kidney disorders, neurological disorders, whole body growth disorders, and immunological disorders.

As used herein, the term "hyperglycemic disorders" refers to all forms of diabetes and disorders resulting from insulin resistance, such as Type I and Type II diabetes, as well as severe insulin resistance, hyperinsulinemia, and hyperlipidemia, e.g., obese subjects, and insulin-resistant diabetes, such as Mendenhall's Syndrome, Werner Syndrome, leprechaunism, lipoatrophic diabetes, and other lipoatrophies. The preferred hyperglycemic disorder is diabetes, especially Type I and Type II diabetes. "Diabetes" itself refers to a progressive disease of carbohydrate metabolism involving inadequate production or utilization of insulin and is characterized by hyperglycemia and glycosuria.

"Biologically active" IGF-1 refers to IGF-1 that exhibits a biological property conventionally associated with an IGF-1 agonist or antagonist, such as a property that would allow treatment of one or more of the disorders listed above.

The term "effective amount" refers to an amount of IGF-1 or a peptidomimetic or other compound, including chemical entities, effective to treat a disease or disorder in a mammal. In the case of cancer, for example, the effective amount of the peptide may reduce the number of cancer cells; reduce the tumor size; inhibit (i.e., slow to some extent and preferably stop) cancer cell infiltration into peripheral organs; inhibit (i.e., slow at least to some extent and preferably stop) tumor metastasis; inhibit, to some extent, tumor growth; promote apoptosis; and/or relieve to some extent one or more of the symptoms associated with the disorder.

A "precipitant" is an agent in a reservoir solution that precipitates IGF-1 when mixed with an aqueous solution of IGF-1 and allowed to equilibrate so as to form IGF-1 crystals. Examples include chaotropic agents such as ammonium sulfate, polyethylene glycols (of a wide variety of molecular weights ranging, for example, from about 2000 to 20,000), sodium citrate, sodium cacodylate, or a mixture thereof.

A "reservoir solution" is a solution of a precipitant and any other ingredient needed to provide IGF-1 crystals, for example, a detergent such as $C_{12}E_9$ (nonaethylene glycol monododecyl ether, nonaethylene glycol monolauryl ether, polyoxyethylene (9) ether), $C_{12}E_8$ (octaethylene glycol monododecyl ether, octaethylene glycol monolauryl ether, polyoxyethylene (8) lauryl ether), dodecyl-beta-D-maltopyranoside, lauric acid sucrose ester, cyclohexyl-pentyl-beta-D-maltoside, nonaethylene glycol octylphenol ether, cetyltrimethylammonium bromide, decyl-beta-D-maltopyranoside, lauryidimethylamine oxide, cyclohexyl-pentyl-beta-D-maltoside, n-dodecylsulfobetaine, 3-(dodecyldimethylammonio)propane-1-sulfonate, nonyl-beta-D-glucopyranoside, octyl-beta-D-thioglucopyranoside, OSG, N,N-dimethyldecylamine-beta-oxide, methyl-6-O-(N-heptylcarbamoyl)alpha-D-glycopyranoside, sucrose monocaproylate, heptyl-beta-D-thioglucopyranoside, octyl-beta-D-glucopyranoside, cyclohexyl-propyl-beta-D-maltoside, cyclohexylbutanoyl-N-hydroxyethyleglucamide, n-decylsulfobetaine, 3-(decyidimethylammonio)propane-1-sulfonate, octanoyl-N-methylglucamide, hexyl-beta-D-glucopyranoside, and N,N-bis(3-D-gluconamidopropyl)-deoxycholamine. Preferably, the detergent is N,N-bis(3-D-gluconamidopropyl)-deoxycholamine.

"Recrystallization" refers to the procedure, after the initial crystals are grown and determined not to be very large or useful, of adding a substance to the crystals, such as methyl pentanediol, which has the effect of dissolving the crystals, but not diluting anything else much in the crystallization mixture. Then over the course of several days, as the crystallization droplet re-equilibrates with its reservoir solution, the crystals regrow, but this time much larger and more well ordered.

The term "associating with" refers to a condition of proximity between IGF-1 and a chemical entity, or portions thereof. The association may be non-covalent, wherein the juxtaposition is energetically favored by hydrogen bonding, van der Waals interaction, or electrostatic interaction, or it may be a covalent association.

The term "binding site" refers to any or all of the sites where a chemical entity binds or associates with IGF-1.

The term "structural coordinates" refers to the coordinates derived from mathematical equations related to the patterns obtained on diffraction of a monochromatic beam of x-rays by the atoms (scattering centers) of a molecule in crystal form. The diffraction data can be used to calculate an electron density map of the repeating units of the crystal. Those skilled in the art will understand that the data obtained are dependent upon the particular system used, and hence, different coordinates may in fact describe the same crystal if such coordinates define substantially the same relationship as those described herein. An electron density map may be used to establish the positions of the individual atoms within the unit cell of the crystal.

Those of skill in the art understand that a set of structural coordinates determined by x-ray crystallography is not without standard error. Appendix 1 shows the atomic coordinates of IGF-1. For the purpose of this invention, any set of structural coordinates of IGF-1 that have a root mean square deviation of equivalent protein backbone atoms of less than about 2 Å when superimposed—using backbone atoms—on the structural coordinates in Appendix 1 shall be considered identical. Preferably, the deviation is less than about 1 Å and more preferably less than about 0.5 Å.

The term "heavy-atom derivatization" refers to a method of producing a chemically modified form of a crystallized IGF-1. In practice, a crystal is soaked in a solution containing heavy metal atom salts, or organometallic compounds, e.g., lead chloride, gold thiomalate, thimerosal, or uranyl acetate, which can diffuse through the crystal and bind to the surface of the protein. The location of the bound heavy metal atom(s) can be determined by x-ray diffraction analysis of the soaked crystal. This information can be used to generate the phase information used to construct the three-dimensional structure of the molecule.

The term "unit cell" refers to a basic shaped block. The entire volume of a crystal may be constructed by regular assembly of such blocks. Each unit cell comprises a complete representation of the unit of pattern, the repetition of which builds up the crystal.

The term "space group" refers to the arrangement of symmetry elements of a crystal.

The term "molecular replacement" refers to a method that involves generating a preliminary structural model of a crystal whose structural coordinates are unknown, by orienting and positioning a molecule whose structural coordinates are known, e.g., the IGF-1 coordinates in Appendix 1, within the unit cell of the unknown crystal, so as to best account for the observed diffraction pattern of the unknown crystal. Phases can then be calculated from this model, and combined with the observed amplitudes to give an approximated Fourier synthesis of the structure whose coordinates are unknown. This in turn can be subject to any of the several forms of refinement to provide a final accurate structure of the unknown crystal. (See, e.g., Lattman, E., "Use of the Rotation and Translation Functions," *Methods in Enzymology*, 115: 55–77 (1985); Rossman, ed., "The Molecular Replacement Method," *Int. Sci. Rev. Ser. No.* 13 (Gordon and Breach: New York, 1972)). Using the structural coordinates of IGF-1 provided by this invention, molecular replacement may be used to determine the structural coordinates of a crystalline co-complex, unknown ligand, mutant, or homolog, or of a different crystalline form of IGF-1. Additionally, the claimed crystal and its coordinates may be used to determine the structural coordinates of a chemical entity that associates with IGF-1.

The term "chemical entity" or "compound" as used herein means any molecule, molecular complex, compound, peptidomimetic, or fragment thereof that is not IGF-1. Preferably it is a molecule with high oral bioavailability, such as an organic chemical molecule, or a peptide.

B. MODES FOR CARRYING OUT THE INVENTION

The following detailed description of the invention encompasses the crystal structure of IGF-1, methods of making an IGF-1 crystal, and methods of using an IGF-1 crystal and its structural coordinates.

a. Crystal Structure of IGF-1

The claimed invention provides crystals of IGF-1 as well as the structure of IGF-1 determined therefrom. Specifically, the claimed invention provides crystals of IGF-1 having approximately the following dimensions: a=31.831 Å, b=71.055 Å, c=65.995 Å, $\alpha=\beta=\gamma=90.000°$. It has a symmetry, or space group, of $C222_1$. The ribbon structure thereof is shown in FIG. 2 having three helices, with the N-terminal B-region corresponding to residues 3–28, the C-region from residues 29–34, a stretch of poorly ordered residues from residues 35–40, and the A-region from residues 42–62. The D-region (residues 63–70) is essentially disordered. FIGS. 4 and 7 show that the detergent used in the crystallization binds into a small hydrophobic cleft at the base of the B-helix of the structure. The IGF-1 can form a dimer in the crystal, as shown in FIG. 5, wherein the two tails are positioned at the dimer interface. The buried surface area is 689 Å$^2$/monomer, which is 1378 Å$^2$ total. The residues important for IGF-1R binding cluster at the dimer interface, as shown in FIG. 6.

The characteristics of the claimed IGF-1 crystal are further described in the Example herein and the structural coordinates thereof are provided in Appendix 1.

b. Methods of Making an IGF-1 Crystal

In various embodiments, the claimed invention relates to methods of preparing crystalline forms of IGF-1 by first providing an aqueous solution comprising IGF-1. A reservoir solution comprising a precipitant is then mixed with a volume of the IGF-1 solution and the resultant mixed volume is then crystallized. In a preferred step the crystals are again dissolved and recrystallized. An example of a reagent that can be used for recrystallization is methyl pentanediol, which is preferred. The crystals are typically dissolved with this reagent in a small amount to minimize dilution effects of the other reagents and left to regrow for a period of time. In an optional step, the crystalline IGF-1 is isolated from the mixed volume. Preferably, the IGF-1 is obtained from a prokaryotic cell, more preferably a bacterial cell, most preferably *E. coli*. Preferably it is secreted into the periplasm and prepared as described in U.S. Pat. No. 5,723,310.

The concentration of IGF-1 in the aqueous solution may vary, but is preferably about 1 to 50 mg/ml, more preferably about 5 to 15 mg/ml. Similarly, precipitants used in the invention may vary, and may be selected from any precipitant known in the art. Preferably, the precipitant is selected from the group consisting of sodium citrate, ammonium sulfate, polyethylene glycol, sodium cacodylate, or a mixture thereof. More preferably the precipitant is polyethylene glycol buffered with sodium citrate or sodium cacodylate. Any concentration of precipitant may be used in the reservoir solution; however, it is preferred that the concentration be about 20 to 25% if polyethylene glycol, and about 1 to 10 M if sodium citrate, ammonium sulfate, or sodium cacodylate. Preferably, the reservoir solution further comprises a detergent. Preferably, the detergent is present in an amount of about 10 to 50 mM. Also preferably the detergent is N, N-bis(3-D-gluconamidopropyl)-deoxycholamine. The pH of the reservoir solution may also be varied, preferably between about 4 to 10, most preferably about 6.5.

One skilled in the art will understand that each of these parameters can be varied without undue experimentation and acceptable crystals will still be obtained. In practice, once the appropriate precipitating agents, buffers, or other experimental variables are determined for any given growth method, any of these methods or any other methods can be used to grow the claimed crystals. One skilled in the art can determine the variables depending upon one's particular needs.

Various methods of crystallization can be used in the claimed invention, including vapor diffusion, batch, liquid-bridge, or dialysis crystallization. Vapor diffusion crystallization is preferred. See, e.g. McPherson et al., *Preparation and Analysis of Protein Crystals*, Glick, ed. (John Wiley & Co., 1982), pp. 82–159; Jancarik et al., *J. Appl. Crystallogr.*, 24: 409–411 (1991).

In vapor diffusion crystallization, a small volume (i.e., a few milliliters) of protein solution is mixed with a solution containing a precipitant. This mixed volume is suspended over a well containing a small amount, i.e. about 1 ml, of precipitant. Vapor diffusion from the drop to the well will result in crystal formation in the drop.

The dialysis method of crystallization utilizes a semipermeable size-exclusion membrane that retains the protein but allows small molecules (i.e. buffers and precipitants) to diffuse in and out. In dialysis, rather than concentrating the protein and the precipitant by evaporation, the precipitant is allowed to slowly diffuse through the membrane and reduce the solubility of the protein while keeping the protein concentration fixed.

The batch methods generally involve the slow addition of a precipitant to an aqueous solution of protein until the solution just becomes turbid; at this point the container can be sealed and left undisturbed for a period of time until crystallization occurs.

Thus, applicants intend that the claimed invention encompass any and all methods of crystallization. One skilled in the art can choose any of such methods and vary the parameters such that the chosen method results in the desired crystals.

The most preferred method of crystallization involves the method wherein the IGF-1, after isolation from the cell and formulation in, for example, an acetate, citrate, or succinate buffer, as described, for example, in U.S. Pat. No. 5,681,814 and WO 99/51272, is optionally desalted if necessary to a pH of about 4–5, preferably about 4.5, to form an aqueous solution. Then, a droplet of the aqueous solution is mixed with about 24% polyethylene glycol buffered to about pH 6.5 with either about 0.1M sodium citrate or about 0.1M sodium cacodylate and with about 1 µl of about 1.4 mM N,N-bis(3-D-gluconamidopropyl)-deoxycholamine as detergent. This solution is then equilibrated by vapor diffusion crystallization with about 1 mL of about 24% polyethylene glycol buffered to about pH 6.5 with either about 0.1M sodium citrate or about 0.1M sodium cacodylate until crystallization droplets are formed, usually about 4–5 days. Then about 2 µl of about 100% methyl pentanediol is added to the crystallization droplets so as to dissolve the crystals overnight and thereby form new crystals, usually within a week's time.

The crystal structure was determined by combined anomalous scattering from intrinsic sulfur and fortuitous bromide ion as discussed in detail in the Example below.

c. Methods of Using an IGF-1 Crystal and its Coordinates

The crystalline IGF-1 herein can be used for various purposes. For example, the crystallization process itself further purifies the IGF-1 to homogeneity. Thus, one such purpose is to provide a highly purified IGF-1 that can be used as a standard or control in a diagnostic setting, for example, as a molecular weight marker, or as an ELISA, radioassay, or radioreceptor assay control. Moreover, crystalline IGF-1 is stable at room temperature, can be lyophilized readily, and is less apt to degrade than less pure compositions.

In another use for the invention herein, crystals of IGF-1 of a size and quality to allow performance of x-ray diffraction studies enable those of skill in the art to conduct studies relating to the binding properties of IGF-1, as well as the binding properties of IGFBPs, IGF-1 receptors, and ALS that associate with the IGF-1.

Furthermore, structural information derived from a peptide crystal structure can be used for the identification of chemical entities, for example, small organic and bioorganic molecules such as peptidomimetics and synthetic organic molecules that bind IGF-1 and preferably block or prevent an IGF-1-mediated or -associated process or event, or that act as IGF-1 agonists. An exemplary approach to such a structure-based compound design is described in *Structure Based Drug Design*, Pandi Veerapandian, ed. (Marcell Dekker: New York 1997).

By way of example, having determined the three-dimensional structure of the IGF-1, the skilled artisan constructs a model of the IGF-1 such as those depicted in FIGS. 2 and 5. Since every atom of a peptide or polypeptide can be depicted as a sphere of the appropriate van der Waals radius, a detailed surface map of the folded IGF-1 can be constructed. The surface that results is known as the van der Waals surface. The "solvent-accessible surface" is the surface that is accessible to a chemical probe, a water molecule herein, and is constructed by rolling a water molecule of appropriate radius on the outside of the peptide maintaining contact with the van der Waals surface. Those parts of the van der Waals surface that contact the surface of the water molecule define a continuous surface known as the "solvent-accessible surface." (Creighton, Thomas E., *Proteins: structure and molecular properties*, 2nd. ed. (W. H. Freeman and Company, 1984), pp 227–229).

Such chemical entities presenting a solvent-accessible surface that mimics the solvent-accessible surface of the IGF-1 can be constructed by those skilled in the art. By way of example, the skilled artisan can search three-dimensional structural databases of compounds to identify those compounds that position appropriate functional groups in similar 3-dimensional structural arrangement, then build combinatorial chemistry libraries around such chemical entities to identify those with high affinity.

One approach enabled by this invention is the use of the structural coordinates of IGF-1 to design chemical entities that bind to or associate with IGF-1 and alter the physical properties of the chemical entities in different ways. Thus, properties such as, for example, solubility, affinity, specificity, potency, on/off rates, or other binding characteristics may all be altered and/or maximized.

One may design desired chemical entities by probing an IGF-1 crystal with a library of different entities to determine optimal sites for interaction between candidate chemical entities and IGF-1. For example, high-resolution x-ray diffraction data collected from crystals saturated with solvent allows the determination of where each type of solvent molecule adheres. Small molecules that bind tightly to those sites can then be designed and synthesized and tested for the desired activity. Once the desired activity is obtained, the molecules can be further altered to maximize desirable properties.

The invention also contemplates computational screening of small-molecule databases or designing of chemical entities that can bind in whole or in part to IGF-1. They may also be used to solve the crystal structure of mutants, co-complexes, or the crystalline form of any other molecule homologous to, or capable of associating with, at least a portion of IGF-1.

One method that may be employed for this purpose is molecular replacement. An unknown crystal structure, which may be any unknown structure, such as, for example, another crystal form of IGF-1, an IGF-1 mutant or peptide, or a co-complex with IGF-1, or any other unknown crystal of a chemical entity that associates with IGF-1 that is of interest, may be determined using the structural coordinates as set forth in Appendix 1. Co-complexes with IGF-1 may include, but are not limited to, IGF-1-IGFBP-3, IGF-1-IGFBP-3-ALS, IGF-1-receptor, IGF-1-peptide, or IGF-1-small molecule. This method will provide an accurate structural form for the unknown crystal far more quickly and efficiently than attempting to determine such information without the invention herein.

The information obtained can thus be used to obtain maximally effective inhibitors or agonists of IGF-1. The design of chemical entities that inhibit or agonize IGF-1 generally involves consideration of at least two factors. First, the chemical entity must be capable of physically or structurally associating with IGF-1. The association may be any physical, structural, or chemical association, such as, for example, covalent or noncovalent bonding, or van der Waals, hydrophobic, or electrostatic interactions.

Second, the chemical entity must be able to assume a conformation that allows it to associate with IGF-1. Although not all portions of the chemical entity will necessarily participate in the association with IGF-1, those non-participating portions may still influence the overall conformation of the molecule. This in turn may have a significant impact on the desirability of the chemical entity. Such conformational requirements include the overall three-dimensional structure and orientation of the chemical entity in relation to all or a portion of the binding site.

The potential inhibitory or binding effect of a chemical entity on IGF-1 may be analyzed prior to its actual synthesis and testing by the use of computer-modeling techniques. If the theoretical structure of the given chemical entity suggests insufficient interaction and association between it and IGF-1, the need for synthesis and testing of the chemical entity is obviated. However, if computer modeling indicates a strong interaction, the molecule may then be synthesized and tested for its ability to bind to IGF-1. Thus, expensive and time-consuming synthesis of inoperative compounds may be avoided.

An inhibitory or other binding compound of IGF-1 may be computationally evaluated and designed by means of a series of steps in which chemical entities or fragments are screened and selected for their ability to associate with the individual binding sites of IGF-1.

Thus, one skilled in the art may use one of several methods to screen chemical entities or fragments for their ability to associate with IGF-1. This process may begin by visual inspection of, for example, the binding site on a computer screen based on the IGF-1 coordinates in Appendix 1. Selected fragments or chemical entities may then be positioned in a variety of orientations, or "docked," within an individual binding pocket of IGF-1. Docking may be accomplished using software such as Quanta and Sybyl, followed by energy minimization and molecular dynamics with standard molecular mechanics force fields, such as CHARMM and AMBER.

Specialized computer programs may be of use for selecting interesting fragments or chemical entities. These programs include, for example, GRID, available from Oxford University, Oxford, UK; MCSS or CATALYST, available from Molecular Simulations, Burlington, Mass.; AUTODOCK, available from Scripps Research Institute, La Jolla, Calif.; DOCK, available from University of California, San Francisco, Calif., and XSITE, available from University College of London, UK.

Once suitable chemical entities or fragments have been selected, they can be assembled into an inhibitor or agonist. Assembly may be by visual inspection of the relationship of the fragments to each other on the three-dimensional image displayed on a computer screen, in relation to the structural coordinates disclosed herein.

Alternatively, one may design the desired chemical entities de novo, experimentally, using either an empty binding site or optionally including a portion of a molecule with desired activity. Thus, for example, one may use solid-phase screening techniques where either IGF-1 or a fragment thereof, or candidate chemical entities to be evaluated, are attached to a solid phase, thereby identifying potential binders for further study.

Basically, any molecular modeling techniques may be employed in accordance with the invention; these techniques are known, or readily available to those skilled in the art. It will be understood that the methods and compositions disclosed herein can be used to identify, design, or characterize not only entities that will associate or bind to IGF-1, but alternatively to identify, design, or characterize entities that, like IGF-1, will bind to the receptor, thereby disrupting the IGF-1-receptor interaction. The claimed invention is intended to encompass these methods and compositions broadly.

Once a compound has been designed or selected by the above methods, the efficiency with which that compound may bind to IGF-1 may be tested and modified for the maximum desired characteristic(s) using computational or experimental evaluation. Various parameters can be maximized depending on the desired result. These include, but are not limited to, specificity, affinity, on/off rates, hydrophobicity, solubility, and other characteristics readily identifiable by the skilled artisan.

Additionally, the invention is useful for the production of small-molecule drug candidates. Thus, the claimed crystal structures may be also used to obtain information about the crystal structures of complexes of the IGF-1 and small-molecule inhibitors. For example, if the small-molecule inhibitor is co-crystallized with IGF-1, then the crystal structure of the complex can be solved by molecular replacement using the known coordinates of IGF-1 for the calculation of phases. Such information is useful, for example, for determining the nature of the interaction between the IGF-1 and the small-molecule inhibitor, and thus may suggest modifications that would improve binding characteristics such as affinity, specificity, and kinetics.

d. Other Methods

The invention herein is also useful in providing a method of identifying indirect agonists of IGF-1 based on the inhibitory properties of N,N-bis(3-D-gluconamidopropyl)-deoxycholamine with respect to IGFBPs. This method comprises the steps of: comparing the ability of N,N-bis(3-D-gluconamidopropyl)-deoxycholamine to inhibit binding of IGFBP-1 or -3 to IGF-1 with the ability of a candidate IGF-1 indirect agonist to inhibit such binding; and determining whether the candidate IGF-1 indirect agonist can inhibit such binding at least as well as N,N-bis(3-D-gluconamidopropyl)-deoxycholamine can so inhibit the binding.

Preferably the comparison is accomplished by competition assay between N,N-bis(3-D-gluconamidopropyl)-deoxycholamine and the candidate IGF-1 indirect agonist, using $IC_{50}$ to measure ability to inhibit IGFBP binding. In a more preferred embodiment, inhibition of binding is measured by pre-incubating N,N-bis(3-D-gluconamidopropyl)-deoxycholamine or the candidate agonist molecule with IGF-1 expressed on bacteriophage particles and measuring residual binding of IGF-1 to IGFBP-1 or IGFBP-3 in a plate-based assay, such as an ELISA.

The invention further provides a method of identifying indirect agonists of IGF-1 comprising co-crystallizing the candidate agonist with IGF-1 to form a co-crystalline structure and determining if the candidate agonist molecule binds to one or both of two patches on IGF-1. The first patch contains the amino acid residues Glu 3, Thr 4, Leu 5, Asp 12, Ala 13, Phe 16, Val 17, Cys 47, Ser 51, Cys 52, Asp 53, Leu 54, and Leu 57, and the second patch cohtains the amino acid residues Val 11, Gln 15, Phe 23, Phe 25, Asn 26, Val 44, Phe 49, and Arg 55 of IGF-I (SEQ ID NO: 1). For purposes herein, binding means that there is at least one contact between each listed amino acid residue of a given patch and the candidate agonist molecule that is less than or equal to 6 angstroms in the co-crystalline structure. Such a candidate agonist molecule will have the property of inhibiting binding of IGFBP-1 or IGFBP-3 to IGF-1. The preferred such candidate agonist molecule will inhibit binding of IGFBP-1 or -3 to IGF-1 at least as well as N, N-bis(3-D-gluconamidopropyl)-deoxycholamine. More preferred is the method wherein inhibition of binding is measured using a competition assay between N, N-bis(3-D-gluconamidopropyl)-deoxycholamine and the candidate agonist molecule. Most preferred is the method wherein inhibition of binding is measured by pre-incubating N, N-bis(3-D-gluconamidopropyl)-deoxycholamine or the candidate agonist molecule with IGF-1 expressed on bacteriophage particles and measuring residual binding of IGF-1 to IGFBP-1 or IGFBP-3 in a plate-based ELISA assay.

The N,N-bis(3-D-gluconamidopropyl)-deoxycholamine detergent herein can be used as a template to perform design of small-molecule drugs that elicit the same effect as the detergent (compete with IGF-1 for IGFBP binding and subsequent disruption of the interaction of IGFBP with IGF-1 to free IGF-1 in situ so that it is active and will interact with the receptor. As opposed to the other detergents tested in the Examples below, N,N-bis(3-D-gluconamidopropyl)-deoxycholamine lacks an oxygen atom at position C10. This region of the detergent is in close contact with the side-chain atoms of residues Leu 5, Leu 54, and Leu 57 of IGF-1. Molecules with this same type of conformation would work as indirect IGF-1 agonists.

The indirect agonist so identified can be used in a method for treating an agonist disorder wherein an effective amount of the indirect agonist of IGF-1 is administered to a mammal with such a disorder. Hence, such agonist may be used therapeutically in a pharmaceutical preparation, for example, in clinical trials or commercialized for the agonist disorders as defined herein. Thus, the formulation of the indirect agonist herein can be used to treat any condition that would benefit from treatment with IGF-1, including, for example, diabetes, chronic and acute renal disorders, such as chronic renal insufficiency, necrosis, etc., obesity, hyperinsulinemia, GH-insufficiency, Tumer's syndrome, short stature, undesirable symptoms associated with aging such as increasing lean-mass-to-fat ratios, immuno-deficiencies including increasing CD4 counts and increasing immune tolerance, catabolic states associated with wasting, etc., Laron dwarfism, insulin resistance, and so forth.

For therapeutic use, the indirect agonist composition herein may be directly administered to the mammal by any suitable technique, including orally, parenterally, intranasally, or intrapulmonarily, and can be administered locally or systemically. The specific route of administration will depend, e.g., on the medical history of the patient, including any perceived or anticipated side or reduced effects using IGF-1, and the disorder to be treated. Examples of parenteral administration include subcutaneous, intramuscular, intravenous, intraarterial, and intraperitoneal administration. Most preferably, the administration is by continuous infusion (using, e.g., minipumps such as osmotic pumps), or by injection (using, e.g., intravenous or subcutaneous means). The administration may also be as a single bolus or by slow-release depot formulation. Most preferably, the direct agonist is administered orally or by infusion or injection, at a frequency of, preferably, one-half, once, twice, or three times daily, most preferably daily.

The agonist composition to be used in the therapy will be formulated and dosed in a fashion consistent with good medical practice, taking into account the clinical condition of the individual patient (especially the side effects of treatment with the agonist), the site of delivery of the agonist composition, the method of administration, the scheduling of administration, and other factors known to clinical practitioners. The "effective amount" of agonist for purposes herein is thus determined by such considerations and must be an amount that treats the disorder in question.

As a general proposition, the total pharmaceutically effective amount of agonist administered parenterally per dose will be in the range of about 1 µg/kg/day up to about 100 mg/kg/day, preferably 10 µg/kg/day up to about 10 mg/kg/day. If given continuously, the agonist is generally administered in doses of about 1 µg/kg/hour up to about 100 µg/kg/hour, either by about 1–4 injections per day or by continuous subcutaneous infusions, for example, using a minipump or a portable infusion pump. An intravenous bag solution may also be employed. The key factor in selecting an appropriate dose is the result obtained as measured by criteria as are deemed appropriate by the practitioner. If the agonist is administered together with insulin, the latter is used in lower amounts than if used alone, down to amounts which by themselves have little effect on blood glucose, i.e., in amounts of between about 0.1 IU/kg/24 hour to about 0.5 IU/kg/24 hour.

For parenteral administration, in one embodiment, the agonist is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulation is prepared by contacting the agonist uniformly and intimately with a liquid carrier or a finely divided solid carrier or both. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low-molecular-weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; nonionic surfactants such as polysorbates, poloxamers, or PEG; and/or neutral salts, e.g., NaCl, KCl, $MgCl_2$, $CaCl_2$, etc.

The agonist is typically formulated individually in such vehicles at a concentration of about 0.1 mg/ml to 100 mg/ml, preferably 1–10 mg/ml, at a pH of about 4.5 to 8. The final formulation, if a liquid, is preferably stored at a temperature of about 2–8° C. for up to about four weeks. Alternatively, the formulation can be lyophilized and provided as a powder for reconstitution with water for injection that is stored as described for the liquid formulation.

The agonist to be used for therapeutic administration must be sterile. Sterility is readily accomplished by filtration through sterile filtration membranes (e.g., 0.2 micron membranes). Therapeutic agonist compositions generally are placed into a container having a sterile access port, for example, an intravenous solution bag or vial having a stopper pierceable by a hypodermic injection needle.

The agonist ordinarily will be stored in unit or multi-dose containers, for example, sealed ampoules or vials, as an aqueous solution or as a lyophilized formulation for reconstitution.

The invention will be more fully understood by reference to the following examples. They should not, however, be construed as limiting the scope of the invention. The disclosures of all literature and patent citations mentioned herein are expressly incorporated by reference.

EXAMPLE 1

Crystallization and Characterization of IGF-1 Crystals

Crystallization of IGF-1 and Data Collection

Recombinant human IGF-1 (rhIGF-1) was obtained as described in the Examples of U.S. Pat. No. 5,723,310 using a polymer/salt combination for phase-forming species and formulated as described in the Examples of U.S. Pat. No. 5,681,814 (acetate, NaCl, polysorbate 20, and benzyl alcohol). Specifically, the initial isolation of IGF-1 from *E. coli* was achieved using aqueous two-phase separation (Hart et al., *Bio/Technology*, 12: 1113–1117 (1994)), followed by refolding (Hart et al., *Biotechnol. Appl. Biochem.*, 20: 217–232 (1994)), and subsequent chromatographic purification, including large-scale reverse-phase high-performance liquid chromatography (Olson et al., *J. Chromatogr.*, A675: 101–112 (1994)). It was placed in a vial containing 7 ml of 10 mg/ml rhIGF-1. Prior to crystallization, the IGF-1 was desalted into 0.15 M NaCl and 20 mM sodium acetate (pH 4.5), and diluted to a final concentration of 10 mg/ml. Initially, crystallization trials were set up in the presence of 1 mM of an IGF-1-binding peptide. However, no peptide was ever observed in the crystal, and crystals grown in the absence of the peptide were later shown to be isomorphous to the specimen reported here. A 4-µl droplet of the IGF-1 solution was mixed with 5 µl of reservoir solution (24% polyethylene glycol 3350 buffered to pH 6.5 with 0.1M sodium cacodylate) and 1 µl of 14 mM of N,N-bis(3-D-gluconamidopropyl)-deoxycholamine, which is obtained in a CRYSTAL SCREEN™ reagent kit used for crystallization condition screenings and available from Hampton Research, Inc., Laguna Nigel, Calif. This solution was allowed to equilibrate via vapor diffusion (Jancarik et al., supra) with 1 ml of reservoir solution. Thus, a drop of the mixture was suspended under a plastic cover slip over the reservoir solution. Small crystals with a thin, plate-like morphology appeared within 4–5 days. At this point, 2 µl of 100% methyl pentanediol (MPD) (to a final concentration of 20%) was added to the crystallization droplet, and the crystals dissolved overnight. Within 1 week, crystals reappeared and grew to final dimensions of 0.2 mm×0.1 mm×0.05 mm with noticeably sharper edges. These crystals were used for all subsequent analysis.

Those of skill in the art will appreciate that the aforesaid crystallization conditions can be varied. By varying the crystallization conditions, other crystal forms of IGF-1 may be obtained. Such variations may be used alone or in combination, and include, for example, varying final protein concentrations between about 5 and 35 mg/ml; varying the IGF-1-to-precipitant ratio, varying precipitant concentrations between about 20 and 30% for polyethylene glycol, varying pH ranges between about 5.5 and 7.5, varying the concentration or type of detergent, varying the temperature between about −5 and 30° C., and crystallizing IGF-1 by batch, liquid bridge, or dialysis methods using the above conditions or variations thereof. See McPherson et al. (1982), supra.

Characterization of IGF-1 Crystals

A single crystal was transferred from the mother liquor to a cryo-protectant solution consisting of 25% (w/v) polyethylene glycol 3350, 30% MPD, 0.2 M sodium cacodylate pH 6.5, 2.8 mM of N,N-bis(3-D-gluconamidopropyl)-deoxycholamine, and 1 M NaBr. The diffraction was to 1.8 Å. After 30 seconds in this solution, the crystal was flash-cooled by plunging it into liquid nitrogen. The technique of freezing the crystals essentially immortalizes them and produces a much higher quality data set. All subsequent manipulations and x-ray data collection were performed at 100° Kelvin.

A 4-wavelength MAD data set was collected at beamline 9–2 at the Stanford Synchrotron Radiation Laboratory, with the order of the data sets as follows: Br peak ($\lambda 1$), low-energy remote ($\lambda 2$), Br inflection ($\lambda 3$), and high-energy remote ($\lambda 4$). The Br peak and inflection points were estimated from fluorescence scans of the crystal, and the low-energy remote was chosen to be 1.54 angstroms, to maximize the small sulfur anomalous signal at this wavelength while minimizing absorption effects. No inverse beam geometry was used. Data reduction was performed using Denzo and Scalepack (Otwinowski and Minor, *Methods in Enzymology,* 276: 307–326 (1997)). To determine the most accurate scale and B-factors possible, data for all four wavelengths were initially scaled together, assuming no anomalous signal. The scale and B-factors determined from this scaling run were then applied to each of the four data sets.

The crystals belong to space group $C222_1$ with unit cell dimensions or constants of: a=31.83 Å, b=71.06 Å, and c=66.00 Å. $\alpha=\beta=\gamma=90.000°$. The asymmetric unit of the crystals contained a monomer of IGF-1 bound to a single detergent molecule, yielding a Matthew's coefficient of 2.4 $Å^3/Da$, or 48.1% solvent. The solvent content of the crystals was about 55%.

Structure Determination

Initial attempts at determining the structure of IGF-1 by molecular replacement, using either the available NMR models of IGF-1 or the crystal structure of insulin, were unsuccessful. For this reason, the structure was determined de novo by Br multiwavelength anomalous dispersion (MAD) (Dauter et al., *Acta Crystallogr.* D56: 232–237 (2000)).

The coordinates of the single-bound bromide were determined by manual inspection of the anomalous and dispersive difference Patterson maps. The hand ambiguity was resolved by phase refinement using the program SHARP (De La Fortelle and Bricogne, *Methods in Enzymology,* 276: 472–494 (1997)) from Global Phasing Limited, 43 Newton Road, Cambridge CB2 2AL, ENGLAND, followed by examination of anomalous-difference Fourier maps calculated using the $\lambda 2$ Bijvoet differences. A cluster of six peaks for one hand of the Br coordinates was consistent with the disulfide structure of insulin (PDB entry: IZNI). These six peaks correspond to the six Cys S$\gamma$atoms in IGF-1; a seventh sulfur (Met 59 S$\delta$) was never detected in anomalous-difference Fourier maps, presumably due to its higher temperature factor (36.7 $Å^2$). At this point, the six Cys S$\gamma$positions were included in the phase refinement, with the $\lambda 1$ data set used as a reference. Throughout the phase refinement, the Br f" was refined for the $\lambda 1$ data set, f' and f" were refined for $\lambda 3$, and both were kept fixed for data sets $\lambda 2$ and $\lambda 4$; the f" and f' values for sulfur were kept fixed at the theoretical values for each wavelength. The small anomalous signal from the sulfur atoms had a modest effect on the phasing statistics, but the resulting electron-density maps showed improved connectivity, especially in the less well ordered regions of IGF-1.

Density modification (solvent flattening and histogram mapping) was performed using DM (Collaborative Computational Project Number 4, *Acta Crystallogr.,* D50: 760–763 (1994); Cowtan, *Joint CCP4 and ESF-EACBM Newsletter on Protein Crystallography,* 31: 34–38 (1994)), and the resulting electron-density maps were of high quality. Approximately 50% of the structure, corresponding to the three helical regions of IGF-1, was built directly into the experimental electron-density maps using the programs O (Jones et al., *Acta Crystallogr.,* A47: 110–119 (1991)) and QUANTA (version 97.0, MSI, San Diego, Calif.). Several rounds of phase combination using Sigmaa (Collaborative Computational Project Number 4, supra; Read, *Acta Crystallogr.,* A42: 140–149 (1986)) allowed the remainder of the molecule to be modeled. Atomic positional and restrained B-factor refinement utilized the maximum-likelihood target function of CNX (Brünger et al., *Acta Crystallogr.,* D54: 905–921 (1998) and MSI, San Diego, Calif.), coupled with a "mask"-type bulk solvent correction and anisotropic overall B-factor scaling.

The final model contains residues 3–34 and 41–64 of IGF-1, one N,N-bis(3-D-gluconamidopropyl)-deoxycholamine molecule, 1 Br⁻, and 50 water molecules. The model was refined against the $\lambda 3$ data set, since the data statistics demonstrated this data set to be of higher quality than the others. All data from 20- to 1.8-angstrom resolution were included in the refinement, with no application of a sigma cutoff. Secondary structure assignments were made with the program PROMOTIF (Jones et al., supra; Hutchinson and Thornton, *Protein Science,* 5: 212–220 (1996)).

While the well-ordered positions of IGF-1 were essentially identical using the two sets of phases, the more flexible regions of the molecule showed dramatically improved connectivity upon inclusion of the sulfurs in the phasing. Experimental electron density maps showing the turn region of IGF-1 immediately following the first helix (residues 19, 20, and 21) indicate that using the combined Br and S phases resulted in a much more well-connected map than using just the Br phases alone. At this point, using the Br+S phases, about 50% of the molecule could be traced directly into the experimental maps.

Description of the Structure

After several cycles of model building and phase combination, the final model, shown in FIG. 2, contains residues 3–34 and 41–64 of IGF-1 (SEQ ID NO: 1), a single-bound detergent molecule, and 46 water molecules. The R factor to 1.8 Å is 23.7%, and the free R factor is 26.9%, with good stereochemistry. The N-terminal B-region corresponds to residues 3–28, the C-region from 29–34, a stretch of poorly ordered residues from 35–40, and the A-region from 42–62 of IGF-I (SEQ ID NO: 1). The D-region (63–70) is essentially disordered.

The structure of IGF-1 is similar to insulin (see FIG. 3), with a Root-Mean-Squared-Deviation (RMSD) of 3 Å over backbone atoms that are conserved between the two molecules. Most of these deviations occur in the flexible regions, and when only the helical regions are considered, the RMSD between alpha-carbon atoms is about 0.47 Å. The major difference is the extension of the C-region, for which there is no counterpart in mature insulin, away from the body of the molecule. This loop contains many of the residues that are known to be important for receptor binding.

An extensive alanine-scan mutagenesis study on IGF-1 has shown which residues are important for binding to IGFBP-1 and IGFBP-3 (Dubaquie and Lowman, supra). The residues that bind to IGFBP-3 are similar to those that bind IGFBP-1, although IGFBP-3 is believed to depend more on backbone interactions and is less severely affected by alanine mutations. There is no one dramatic spot where residues important for IGFBP-1 and IGFBP-3 binding are clustered, and mutations that impair binding are scattered all over the molecule. There appears to be a slight clustering of sites at the N-terminus, with many of these sites being intrinsically hydrophobic.

As shown in FIGS. 4 and 7, the detergent molecule binds into a small hydrophobic cleft at the base of the B-helix. There are several direct side-chain contacts to the detergent from residues 5, 7, and 10. Despite the overlap of the detergent binding site with a portion of the IGFBP-1/IGFBP-3 binding epitope, the preliminary results suggest, without being limited to any one theory, that the detergent does not inhibit binding of these proteins to IGF-1. The opposite face of the detergent is making a symmetry contact to the opposite face of IGF-1.

As shown in FIG. 5, there is only one large crystal packing contact between symmetry-related IGF-1 molecules, which results in a symmetric homodimer. The buried surface area is 1378 Å$^2$, which is in the range of physiologically relevant protein-protein interfaces.

FIG. 6 shows that the residues known to be important for receptor binding cluster at this dimer interface. Shown are Tyr24, Thr29, Tyr31, and Tyr60. Mutation of these residues results in anywhere from 6–20× loss in affinity for receptor for individual mutations, or 240→1200× loss in affinity for double mutations. Also shown are Phe23 and Phe25, which are interchangeable with Phe24 and Tyr26 of insulin, with no loss of affinity.

Further Description of the Structure

IGF-1 (SEQ ID NO: 1) is composed primarily of three helical segments corresponding to the B-helix (IGF-1 residues 7–18) and two A-helices (IGF-1 residues 43–47 and 54–58) of insulin. The hydrophobic core is essentially identical to that described for the NMR structures of IGF-1, including the three disulfide linkages between Cys 6 and Cys 48, Cys 18 and Cys 61, and Cys 47 and Cys 52, as noted in the references above. Residues 3 through 6 do not form any regular secondary structure, and hence, the structure described herein can be classified as being most similar to the T-form of insulin (Derewenda et al., *Nature,* 338: 594–596 (1989)). Indeed, when IGF-1 and the T-form of insulin are superimposed on the Cα positions of their respective helical segments (IGF-1 SEQ ID NO: 1) residues 8–19, 42–49, and 54–61; insulin (SEQ ID NO: 3) residues B9–B20, A1–A8, and A13–A20) the RMSD is only 0.47 angstroms. As in insulin, residues 18–21 at the end of the B-helix form a type II'β-turn, which redirects the backbone from the B-helix into an extended region. Residues 24–27 form a type VIII β-turn to accommodate the C-region, which extends away from the core of IGF-1, and interacts with a symmetry-related molecule. Residues 30–33 form a well-defined type II beta-turn, prominently displaying Tyr 31 at the i+1 position. Residues 35–40 have not been modeled, as the electron density in this region is weak and disconnected. Only the first two residues of the D-region (residues 63 and 64) are ordered in the structure.

The C-region of IGF-1 (SEQ ID NO: 1) mediates a two-fold symmetric crystal-packing interaction across the α-axis of the unit cell. This interaction buries 689 Å$^2$ of solvent-accessible surface area from each molecule of IGF-1, or 1378 Å$^2$ total, and is the largest interface in the crystal. A total of 28 intermolecular contacts of distance 3.6 Å or less are formed via this interface, with the next most extensive crystal packing interaction forming only nine contacts. The core of the interface is dominated by Tyr24 and Pro28 from each monomer, which bury 39 Å$^2$ and 57 Å$^2$ of solvent-accessible surface area, respectively. The aromatic ring of Tyr 31, which lies at the tip of the loop at the furthest point from the core of IGF-1, packs against the phenolic rings of Phe 23 and Phe 25 of the symmetry-related molecule. In addition to these hydrophobic interactions, two main-chain hydrogen bonds (Tyr 31 N-Phe 23 O and Ser 34 N-Asp 20 O of IGF-I, SEQ ID NO: 1) are present in the dimer interface. Residues from the D-region (62–64) are also partially sequestered by this dimer formation. Because of these interactions, most of the C-region in the crystal is well-ordered, providing the first high-resolution view of the conformation of this biologically important loop.

Although 72 detergent compounds, including the similar 3-((3-cholamidopropyl) dimethylammonio)-1-propane sulphonate (CHAPS) and 3-((3-cholamidopropyl)dimethylammonio)-2-hydroxypropanesulfonic acid (CHAPSO) detergents, were screened in crystallization trials, only N, N-bis (3-D-gluconamidopropyl)-deoxycholamine yielded crystals. A single molecule of N, N-bis(3-D-gluconamidopropyl)-deoxycholamine interacts with residues, forming a small hydrophobic cleft on one surface of IGF-1 (SEQ ID NO: 1 (Leu 5, Phe 16, Val 17, Leu 54, and Leu 57) (FIG. 7A). The preference for N, N-bis(3-D-gluconamidopropyl)-deoxycholamine is explained, without being limited to any one theory, by the absence of an oxygen atom at position C10 in the detergent molecule. This region of the detergent is in close contact with the side chain atoms of residues Leu 5, Leu 54, and Leu 57 in IGF-1. The opposite face of the detergent mediates a symmetry contact with residues Val 11, Leu 14, and Gln 15 of a symmetry-related IGF-1 molecule. Intriguingly, this face of N, N-bis(3-D-gluconamidopropyl)-deoxycholamine also contacts the edge of the dimer interface, with close contacts to Phe 23 and Phe 25 of the same IGF-1 molecule, as well as Tyr 31 and Gly 32 of the dimeric partner (FIG. 7B). A more detailed analysis indicates that the detergent binds to two patches of binding pockets of IGF-1 (SEQ ID NO: 1). One patch has the amino acid residues Glu 3, Thr 4, Leu 5, Asp 12, Ala 13, Phe 16, Val 17, Cys 47, Ser 51, Cys 52, Asp 53, Leu 54, and Leu 57, and the second patch has the amino acid residues Val 11, Gln 15, Phe 23, Phe 25, Asn 26, Val 44, Phe 49, and Arg 55. Binding is defined by having at least one contact between each listed amino acid residue and the candidate agonist molecule that is less than or equal to 6 angstroms.

Discussion

The C-region in the IGF-1 crystal structure extends out from the core of the molecule, with residues 30–33 forming a canonical type II beta-turn, and the remainder of the C-region forming a crystallographic dimer with a symmetry-related molecule. Tyr 31 has been implicated as being a critical determinant for IGF-1R binding (Bayne et al. (Vol. 264), supra; Bayne et al. (Vol. 265), supra; Cascieri et al., supra), and its location at the tip of this extension places it in an ideal location to interact with a receptor molecule. While this region of IGF-1 is not well-defined by NMR data, the conformation of the C-region in the crystal is likely to reflect a prevalent solution conformation. There is evidence of a reverse turn at the tip of the loop and a hinge bending at the loop termini of IGF-2 (SEQ ID NO: 2; Torres et al., supra). Thus, while crystal packing forces undoubtedly help stabilize the orientation of this loop, its conformation appears to be consistent with the solution structure of the closely related IGF-2.

The size of the interface formed by the crystallographic dimer is well within the range of buried surface area in known biological complexes (Janin and Chothia, *J. Biol. Chem.*, 264: 16027–16030 (1990)). In addition, this interaction partially excludes from solvent several of the residues known to be important for binding to the IGF-1R, including Phe 23 (69% buried), Tyr 24 (64% buried), Phe 25 (29% buried), and Tyr 31(38% buried) of IGF-I, SEQ ID NO: 1. Other groups have also reported homodimeric interactions of IGF-1 (SEQ ID NO: 1) and IGF-2 (SEQ ID NO: 2). Laajoki et al., (2000), supra, report that at a concentration of 1 mM, an engineered form of IGF-1 (Long-[Arg$^3$]IGF-1) partitions into about 20% dimer/80% monomer, a ratio that is in good agreement with the estimate of 3.6 mM $K_d$. In their NMR study of IGF-2, Torres et al., supra, reported that the amide protons of residues in the C-region were slowly exchanging with solvent, suggesting that IGF-2 forms a homodimer in solution. However, despite the significant amount of surface area that is buried upon dimer formation in the crystal, the affinity of IGF-1 for itself is very weak. In addition, the known binding stoichiometry of one IGF-1 molecule per receptor dimer (De Meyts, supra) makes it difficult to rationalize the biological significance of IGF-1 dimerization. In conclusion, the IGF-1 dimer in this crystal form results from the high concentration of IGF-1 in the crystallization experiment, and does not represent a physiologically relevant form of the molecule.

The very low quality of NMR spectroscopic data obtained for IGF-1 at near-neutral pH has been attributed to a combination of self-association and internal mobility that leads to a large variation in resonance line width (Cooke et al., supra). As a result, NOESY spectra acquired on IGF-1 contain many broad, overlapped peaks and few sharp well-resolved correlations. NOESY spectra collected for IGF-1 in the presence of an excess of N, N-bis(3-D-gluconamidopropyl)-deoxycholamine have a similar appearance. Thus, detergent binding is not sufficient to eliminate the aggregation or inherent flexibility of IGF-1 and does not facilitate characterization of the solution conformation of the protein. Likewise, detergent binding does not alter the aggregation state of IGF-1, as assessed by analytical ultracentrifugation experiments in the presence of N, N-bis(3-D-gluconaniidopropyl)-deoxycholamine. This is in contrast to observations in the crystalline state where addition of N, N-bis(3-D-gluconamidopropyl)-deoxycholamine leads to a well-packed crystallographic dimer and crystals that diffract to high resolution. Jansson et at, *J. Biol. Chem.*, 273: 24701–24707 (1998) noted that the lack of NMR assignments in the region immediately surrounding Cys 6 of IGF-I, SEQ ID NO: 1, which includes Leu 5 and Gly 7, was indicative of the Cys 6-Cys 48 disulfide undergoing intermediate exchange between a cis and trans configuration. The fact that the detergent binds to one face of the B-helix immediately opposite this disulfide suggests, without being limited to any one theory, that it may serve to stabilize this region of the molecule by more complete packing of the hydrophobic cleft. Indeed, in the crystal structure herein, the Cys 6-Cys 48 is clearly in the trans conformation, and there is no evidence of multiple conformations.

Conclusion

The crystal structure of IGF-1 has been determined using anomalous scattering from the intrinsic sulfur atoms and a Br-ion bound at a fortuitous halide-binding site. The structure is very similar to insulin, with the only major difference being the C-region, which protrudes from the body of the protein and mediates a homodimeric interaction. The amount of buried surface area is consistent with the fact that at neutral pH, IGF-1 undergoes self-association in a concentration-dependent manner. In addition, several residues that are important for receptor binding are found at this dimer interface, suggesting, without being limited to any one theory, that effects on receptor binding by mutation of these residues may be a result of disruption of the dimer, rather than direct contact with the receptor surface.

EXAMPLE 2

Diffusion-based Measurement of Detergent Binding

NMR-derived diffusion measurements were used to estimate the $K_d$ for the interaction between IGF-1 and N,N-bis (3-D-gluconamidopropyl)-deoxycholamine. Samples were prepared in 50 mM phosphate buffer in $D_2O$, pH 6.5 (uncorrected meter reading), and contained: 1.0 mM N,N-bis(3-D-gluconamidopropyl)-deoxycholamine+0.5 mM IGF-1, 0.5 mM N, N-bis(3-D-gluconamidopropyl)-deoxycholamine+0.25 mM IGF-1; 0.25 mM N,N-bis(3-D-gluconamidopropyl)-deoxycholamine+0.125 mM IGF-1; or N,N-bis (3-D-gluconamidopropyl)-deoxycholamine only (1.0, 0.5, or 0.25 mM). All spectra were acquired at 40° C. on a Bruker AVANCE 500™ spectrometer (Bruker Analytik GmbH) equipped with a 5-mm triple-axis gradient, triple-resonance probe. Diffusion measurements were made with a bipolar pulse pair method with δ=5 ms, τ=2 ms, and Δ=25 or 40 ms for N,N-bis(3-D-gluconamidopropyl)-deoxycholamine alone or N,N-bis(3-D-gluconamidopropyl)-deoxycholamine+IGF-1, respectively (Wu et al., *J. Magn. Reson., Ser. A* 115: 260–264 (1995)). Spectra were collected with 128 to 1024 transients as the z-gradient strength was increased from 0.009 to 0.45 T·m$^{-1}$ in 18 equal increments; measurements were made at least twice on each sample. Spectra were processed and peak heights extracted with the program FELIX (v98.0, MSI, San Diego). Diffusion constants, proportion of bound detergent, and resulting $K_d$ were extracted as described by Fejzo et al., *Chemistry & Biology*, 6: 755-769 (1999). Spectra were also collected on samples containing 1.0 mM 3-((3-cholamidopropyl)dimethylammonio)-1-propane sulphonate, a zwitterionic detergent used for membrane solubilization, and 1.0 mM 3-(3-cholamidopropyl)dimethylammonio)-1-propane sulphonate+0.5 mM IGF-1. Two-dimensional NOESY spectra (Jeener et al., *J. Chem. Phys.*, 71: 4546–4553 (1979)) were collected on a 0.5-mM sample of IGF-1 in the presence or absence of 1.0 mM N,N-bis(3-D-gluconamidopropyl)-deoxycholamine with a mixing time of 100 ms.

IGF-1 Phage ELISA

E. coli cells (XL1-Blue, Stratagene) freshly transformed with the phage vector pIGF-g3 displaying human IGF-1 as described in Dubaquie and Lowman, supra, were grown overnight in 5 ml of 2YT medium (Sambrook et al., *Molecular Cloning: A Laboratory Handbook* (Cold Spring Harbor Laboratory Press, Cold Spring Harbor, N.Y., 1989)). The phage particles displaying IGF-1 were titered against IGFBP-1 and IGFBP-3 to obtain a 500–1000-fold dilution for preincubation with serial dilutions of the detergents and binding protein standards for 45 minutes. Microwell clear polystyrene immunoplates with a MAXISORP™ surface (Nunc, Denmark) were coated with IGFBP-1 or IGFBP-3 protein overnight at 4° C. (50 µl at 3 µg/mL in 50 mM carbonate buffer, pH 9.6), blocked with 0.5% TWEEN® 20 polyoxyethylene sorbitan monolaurate (Atlas Chemical Co.), and PBS and washed eight times with PBS and 0.05% TWEEN® 20 polyoxyethylene sorbitan monolaurate. The samples were added to the plates for 30 minutes. Plates were washed eight times with PBS and 0.05% TWEEN® 20 polyoxyethylene sorbitan monolaurate, incubated with 50 µL of 1:10,000 horseradish peroxidase/anti-M13 antibody conjugate (Amersham Pharmacia Biotech, Piscataway, N.J.) in PBS and 0.5% BSA for 30 minutes, and then washed eight times with PBS and 0.05% TWEEN® 20 polyoxyethylene sorbitan monolaurate and two times with PBS. Plates were developed using a tetramethylbenzidine substrate (Kirkegaard and Perry, Gaithersburg, Md.), stopped with 1.0 $H_3PO_4$, and read spectrophotometically at 450 nm.

Sedimentation Equilibrium Analysis

The self-association of IGF-1 was determined by sedimentation equilibrium analysis. The experiments were conducted at 20° C. in an OPTIMA™ XL-A/XL-1 analytical ultracentrifuge (Beckman Coulter, Inc.). The samples were prepared in 0.1 M citrate buffer, pH 6.5, 75 mM NaCl with a loading concentration from 1 mM to 0.01 mM. The concentration gradients were measured at rotor speeds of 25000 and 30000 rpm at 280 nm or 285 nm using a scanning absorption optical system. The attainment of an equilibrium state was verified by comparing successive scans after approximately 16 hours. The partial specific volume of IGF-1 was calculated from its amino acid composition. The data were fit as a single ideal species or the ideal dimer self-association models using a non-linear least-squares fitting program, NONLIN (Johnson et al., *Biophys. J.*, 36: 578–588(1981)). The association constants were determined from the best-fit values of the model, returned by non-linear least-squares regression.

Results:

N,N-bis(3-D-gluconamidopropyl)-deoxycholamine Binds to IGF-1 in Solution.

The affinity of IGF-1 for 3-((3-cholamidopropyl)dimethylammonio-1-propane sulphonate and N,N-bis(3-D-gluconamidopropyl)-deoxycholamine was ascertained using solution-NMR methods. The chemical shift changes observed during a titration of N,N-bis(3-D-gluconamidopropyl)-deoxycholamine into a 0.5 mM IGF-1 solution suggested that the affinity was submillimolar and not easily measurable from such data. Instead, diffusion measurements were made on samples at varying IGF-1 concentrations containing 2 molar equivalents of detergent and also on several samples of detergent alone (the detergent concentration was always less than the critical micelle concentration of 1.4 mM for N,N-bis(3-D-gluconamidopropyl)-deoxycholamine and 14 mM for 3-((3-cholamidopropyl)dimethylammonio)-1-propane sulphonate). The decrease in diffusion constant of the detergent in the presence of the protein can be used to estimate the proportion of detergent bound to the protein (Fejzo et al., supra). Since the total concentration of detergent and protein is known, a value of the dissociation constant can be determined. At the three protein concentrations studied (0.5 mM, 0.25 mM, and 0.125 mM), $K_d$ values of 220, 440, and 430 µM were obtained, respectively. This technique has routinely been applied to small molecules (several hundred Daltons molecular weight or less) binding to large proteins. In this particular case, the ligand is relatively large (862 Da) and the protein is relatively small (7648 Da); hence, the differential decrease in diffusion constant on binding is small. This increases the uncertainty with which the dissociation constant can be measured. Given this, the data described above suggest that the $K_d$ for the interaction between N,N-bis(3-D-gluconamidopropyl)-deoxycholamine and IGF-1 is 300±150 µM. A similar analysis of the (3-(3-cholamidopropyl)dimethylammonio)-1-propane sulphonate diffusion data suggests that that $K_d$ in this case is greater than 3 mM.

N,N-bis(3-D-gluconamidopropyl)-deoxycholamine Blocks IGFBP-1 and IGFBP-3 Binding.

To examine the binding epitope of N,N-bis(3-D-gluconamidopropyl)-deoxycholamine on IGF-1, the detergent was preincubated with IGF-1 expressed on bacteriophage particles, and the level of residual binding to IGFBP-1 and IGFBP-3 was measured in a plate-based assay (ELISA). As a control, soluble IGFBP-1 was also tested. As shown in FIG. 8, N,N-bis(3-D-gluconamidopropyl)-deoxycholamine inhibited IGF-1 on phage from binding to IGFBP-1 and IGFBP-3 with $IC_{50}$ values of 480±170 µM and 275±152 µM, respectively. These numbers must be interpreted conservatively, however, since the critical micelle concentration of N,N-bis(3-D-gluconamidopropyl)-deoxycholamine (1.4 mM) presents an upper limit on the curve in FIG. 8. In contrast to the effect of N,N-bis(3-D-gluconamidopropyl)-deoxycholamine, the closely related detergent 3-((3-cholamidopropyl)dimethylammonio)-1-propane sulphonate did not show any inhibition of binding at any of the concentrations tested up to 1 mM. Despite the limitations of the experiment, the $IC_{50}$ values obtained for N,N-bis(3-D-gluconamidopropyl)-deoxycholamine are in good agreement with the NMR-based estimate of a $K_d$ of ~300 µM for the N,N-bis(3-D-gluconamidopropyl)-deoxycholamine-IGF-1 interaction.

Self-Association of IGF-1.

The sedimentation equilibrium data show that IGF-1 undergoes self-association in solution. The average molecular weight increased with increasing protein concentration from 0.01 mM to 1 mM. The average molecular weight at the highest concentration studied (1 mM) is about 37% higher than the monomer molecular weight (10.4 KDa at 1 mM versus 7.6 KDa monomer molecular weight). At concentrations below 0.05 mM, no self-association was observed, and IGF-1 exists only as a monomer in solution at neutral pH. If it is assumed that the higher-molecular-weight species are IGF-1 dimers, the sedimentation data can be fit as a monomer-dimer model with a $K_d$ of 3.6±1.0 mM (FIG. 9).

Discussion

Several studies have identified residues in IGF-1 (SEQ ID NO: 1) that are important for IGFBP binding (Clemmons et al., *Endocrinology*, 131: 890–895 (1992); Dubaquie and Lowman, supra; Jansson et al., supra; Oh et al., (1993), supra; Lowman et al., (1998), supra; and Dubaquie et al., *Endocrinology*, 142: 165–173 (2001)). Dubaquie and Lowman, supra, identified two distinct patches on IGF-1 that interact with IGFBP-1 and IGFBP-3. Patch I consists of Glu 7, Leu 10, Val 11, Leu 14, Phe 25, Ile 43, and Val 44, while patch 2 consists of Glu 3, Thr 4, Leu 5, Phe 16, Val 17, and Leu 54. In the crystal structure of IGF-1, these two patches are involved in detergent-mediated crystal packing contacts. (Specifically, Patch 1 of the crystal structure of IGF-1 consists of amino acid residues Glu 3, Thr 4, Leu 5, Asp 12, Ala 13, Phe 16, Val 17, Cys 47, Ser 51, Cys 52, Asp 53, Leu 54, and Leu 57, and Patch 2 of the crystal structure of IGF-1 consists of amino acid residues Val 11, Gln 15, Phe 23, Phe 25, Asn 26, Val 44, Phe 49, and Mg 55, wherein binding occurs if there is at least one contact between each listed amino acid residue and the candidate agonist molecule that is less than or equal to 6 angstroms.)

The overlap of the detergent binding site with the IGFBP interaction surfaces is entirely consistent with the observation herein that N,N-bis(3-D-gluconamidopropyl)-deoxycholamine blocks IGFBP-1 and IGFBP-3 binding. In contrast, N,N-bis(3-D-gluconamidopropyl)-deoxycholamine does not inhibit IGF-1R-mediated signaling in a cell-based receptor activation assay. These results are consistent with prior studies that demonstrated different binding epitopes on IGF-1 for receptor and IGFBP interactions (Bayne et al., supra, (Vol. 264); Bayne et al., supra, (Vol. 265); Cascieri et al., supra). The identification of N,N-bis(3-D-gluconamidopropyl)-deoxycholamine as an inhibitor of IGFBP interactions allows the ability to develop small-molecule drugs or peptidomimetics that disrupt the IGF-1/IGFBP complex in vivo, thereby releasing receptor-active IGF-1 from the systemic, inactive pool. Such drugs include orally bioavailable therapy for metabolic disease such as diabetes.

Recently, Zeslawski et al. (*EMBO J.*, 20: 3638–3644 (2001) published the crystal structure of IGF-1 in complex with the N-terminal domain of IGFBP-5. The structure of that complex is entirely consistent with the model of detergent inhibition of IGFBP binding presented herein, and also disclosed by Vajdos et al., *Biochemistry*, 40: 11022–11029 (2001). The NMR determination of a complex of IGF-1 bound to a phage-derived IGF-1 antagonist peptide designated IGF-F1-1 (RNCFESVAALRRCMYG (SEQ ID NO:4)), in comparison with other IGF-1 crystal structures, shows that, without limitation to any one theory, a portion of the A-chain (helix III) is mobile in solution, and adopts slightly different conformations when bound to different ligands (detergent, peptide, binding protein).

The complex between peptide IGF-F1-1 and IGF-1 was determined from NMR spectroscopy data collected at 600 and 800 MHz. IGF-1 uniformly labeled with $^{13}C$ and $^{15}N$ was prepared using the scheme outlined by Reilly and Fairbrother, *J. Biomol. NMR*, 4: 459–462 (1994) and purified according to the protocol in Vajdos et al., supra. A slight molar excess of unlabeled IGF-F1-1 was mixed with a 1.5 mM solution of $^{13}C/^{15}N$ IGF-1 and $^1H$, $^{13}C$, and $^{15}N$ NMR resonances assigned from double- and triple-resonance NMR experiments as described by Cavanagh et al. in *Protein NMR Spectroscopy, Principles and Practice* (Academic Press: New York, 1996). Distance restraints within IGF-1 were identified from $^{13}C$-edited NOESY HSQC spectra and $^{15}N$-edited NOESY HSQC spectra (Cavanagh et al, supra).

Intermolecular restraints between IGF-1 and the peptide were obtained from an ω1-filtered, ω2-edited $^{13}C$ HSQC-NOESY spectrum (Lee et al., *FEBS Lett.*, 350: 87–90 (1994)). Intrapeptide distance restraints were obtained from a 2-D $^{13}C$-filtered NOESY spectrum. In addition, φ dihedral angle restraints were obtained from an HNHA spectrum (Cavanagh et al., supra), and χ1 restraints were derived from HNHB and short-mixing-time TOCSY spectra (Clore et al., *J. Biomolec. NMR*, 1: 13–22(1991)). Additional φ, ψ restraints were obtained from an analysis of the H$^α$, N, C$^α$, C$^β$, and CO chemical shifts using the program TALOS (Cornilescu et al., *J. Biomol. NMR*, 13: 289–302 (1999)).

In total, 899 distance restraints (779 intra-IGF-1; 33 intra-peptide; 87 intermolecular), 16 hydrogen bond restraints in helix I, and 138 dihedral angle restraints (71 Φ; 44 Ψ 23 χ1) were used to generate an ensemble of structures using a torsion-angle dynamics protocol with the computer program CNX (Accelrys Inc., San Diego). The structure of IGF-1 (SEQ ID NO: 1) was well defined for the B-region (residues 2–25) and the A-region (residues 41–63) with a mean RMSD from the mean structure for backbone heavy atoms of 0.32±0.06 Å. The C-region (26–40) and the D-region (62–70) were not well defined by the available data. The 20 structures of lowest restraint violation energy had good backbone stereochemistry (80% of residues in the most favored region of Φ/ψ space with none in disallowed regions) and contained few violations of the experimental restraints (mean maximum distance restraint violation 0.09 ±0.02 Å). IGF-F1-1 adopts a conformation very similar to that determined for the peptide by itself in solution. The conformation of IGF-1 contains three helices (residues 7–18, 43–49, and 54–60) and is similar to that seen at lower resolution in previous NMR studies of uncomplexed IGF-1 (see e.g. Cooke et al., supra; Sato et al., supra; and Laajoki et al., supra).

FIG. 10 shows the comparison for the detergent and phage peptide complexes. Specifically, FIG. 10A shows a ribbon diagram of a complex of IGF-1 and N,N-bis(3-D-gluconamidopropyl)-deoxycholamine), and FIG. 10B shows a complex of IGF-1 bound to the phage-derived peptide IGF-F1-1. The B-region (helix I) adopts a very similar conformation in both complexes. The C-loop is only partially ordered in the detergent complex, and ill defined in the peptide complex. Ligand-induced differences are observed for the A-region of IGF-1 (Helix III), at both the backbone (residues 52–60) and side chain (leucine 54 and 57) level. Without limitation to any one theory, maleability in this A-region area is believed to be what allows IGF-1 to bind to so many proteins (six IGFBPs and three receptors).

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the objectives of the present invention.

APPENDIX 1

| | | |
|---|---|---|
| REMARK 3 | CRYSTAL STRUCTURE OF IGF-I SOLVED USING MAD | |
| REMARK 3 | REFINEMENT. | |
| REMARK 3 | PROGRAM: | X-PLOR(online) 98.1 |

APPENDIX 1-continued

| | | |
|---|---|---|
| REMARK 3 | AUTHORS: | BRUNGER |
| REMARK 3 | | |
| REMARK 3 | DATA USED IN REFINEMENT. | |
| REMARK 3 | RESOLUTION RANGE HIGH (ANGSTROMS): | 1.80 |
| REMARK 3 | RESOLUTION RANGE LOW (ANGSTROMS): | 20.00 |
| REMARK 3 | DATA CUTOFF (SIGMA(F)): | 0.2 |
| REMARK 3 | DATA CUTOFF HIGH (ABS(F)): | 10000000.00 |
| REMARK 3 | DATA CUTOFF LOW (ABS(F)): | 0.001000 |
| REMARK 3 | COMPLETENESS (WORKING + TEST) (%): | 94.8 |
| REMARK 3 | NUMBER OF REFLECTIONS: | 6870 |
| REMARK 3 | | |
| REMARK 3 | FIT TO DATA USED IN REFINEMENT. | |
| REMARK 3 | CROSS-VALIDATION METHOD: | THROUGHOUT |
| REMARK 3 | FREE R VALUE TEST SET SELECTION: | RANDOM |
| REMARK 3 | R VALUE (WORKING SET): | 0.237 |
| REMARK 3 | FREE R VALUE: | 0.269 |
| REMARK 3 | FREE R VALUE TEST SET SIZE (%): | 5.6 |
| REMARK 3 | FREE R VALUE TEST SET COUNT: | 382 |
| REMARK 3 | ESTIMATED ERROR OF FREE R VALUE: | 0.014 |
| REMARK 3 | | |
| REMARK 3 | FIT IN THE HIGHEST RESOLUTION BIN. | |
| REMARK 3 | TOTAL NUMBER OF BINS USED: | 6 |
| REMARK 3 | BIN RESOLUTION RANGE HIGH (A): | 1.80 |
| REMARK 3 | BIN RESOLUTION RANGE LOW (A): | 1.91 |
| REMARK 3 | BIN COMPLETENESS (WORKING + TEST) (%): | 74.4 |
| REMARK 3 | REFLECTIONS IN BIN (WORKING SET): | 826 |
| REMARK 3 | BIN R VALUE (WORKING SET): | 0.343 |
| REMARK 3 | BIN FREE R VALUE: | 0.439 |
| REMARK 3 | BIN FREE R VALUE TEST SET SIZE (%): | 5.5 |
| REMARK 3 | BIN FREE R VALUE TEST SET COUNT: | 48 |
| REMARK 3 | ESTIMATED ERROR OF BIN FREE R VALUE: | 0.063 |
| REMARK 3 | | |
| REMARK 3 | NUMBER OF NON-HYDROGEN ATOMS USED IN REFINEMENT. | |
| REMARK 3 | PROTEIN ATOMS: | 475 |
| REMARK 3 | NUCLEIC ACID ATOMS: | 0 |
| REMARK 3 | HETEROGEN ATOMS: | 62 |
| REMARK 3 | SOLVENT ATOMS: | 102 |
| REMARK 3 | | |
| REMARK 3 | B VALUES. | |
| REMARK 3 | FROM WILSON PLOT (A**2): | 25.1 |
| REMARK 3 | MEAN B VALUE (OVERALL, A**2): | 33.8 |
| REMARK 3 | OVERALL ANISOTROPIC B VALUE. | |
| REMARK 3 | B11 (A**2): | 0.00 |
| REMARK 3 | B22 (A**2): | 0.00 |
| REMARK 3 | B33 (A**2): | 0.00 |
| REMARK 3 | B12 (A**2): | 0.00 |
| REMARK 3 | B13 (A**2): | 0.00 |
| REMARK 3 | B23 (A**2): | 0.00 |
| REMARK 3 | | |
| REMARK 3 | ESTIMATED COORDINATE ERROR. | |
| REMARK 3 | ESD FROM LUZZATI PLOT (A): | 0.23 |
| REMARK 3 | ESD FROM SIGMAA (A): | 0.16 |
| REMARK 3 | LOW RESOLUTION CUTOFF (A): | 20.00 |
| REMARK 3 | | |
| REMARK 3 | CROSS-VALIDATED ESTIMATED COORDINATE ERROR. | |
| REMARK 3 | ESD FROM C-V LUZZATI PLOT (A): | 0.28 |
| REMARK 3 | ESD FROM C-V SIGMAA (A): | 0.18 |
| REMARK 3 | | |
| REMARK 3 | RMS DEVIATIONS FROM IDEAL VALUES. | |
| REMARK 3 | BOND LENGTHS (A): | 0.020 |
| REMARK 3 | BOND ANGLES (DEGREES): | 2.0 |
| REMARK 3 | DIHEDRAL ANGLES (DEGREES): | 23.2 |
| REMARK 3 | IMPROPER ANGLES (DEGREES): | 1.09 |
| REMARK 3 | | |
| REMARK 3 | ISOTROPIC THERMAL MODEL: | RESTRAINED |
| REMARK 3 | | |
| REMARK 3 | ISOTROPIC THERMAL FACTOR RESTRAINTS. | RMS SIGMA |
| REMARK 3 | MAIN-CHAIN BOND (A**2): | 4.33; 4.00 |
| REMARK 3 | MAIN-CHAIN ANGLE (A**2): | 6.46; 4.00 |
| REMARK 3 | SIDE-CHAIN BOND (A**2): | 5.41; 8.50 |
| REMARK 3 | SIDE-CHAIN ANGLE (A**2): | 8.14; 9.00 |
| REMARK 3 | | |
| REMARK 3 | NCS MODEL: | NONE |
| REMARK 3 | | |
| REMARK 3 | NCS RESTRAINTS. | RMS SIGMA/WEIGHT |
| REMARK 3 | GROUP 1 POSITIONAL (A): | NULL; NULL |
| REMARK 3 | GROUP 1 B-FACTOR (A**2): | NULL; NULL |
| REMARK 3 | | |
| REMARK 3 | PARAMETER FILE 1: MSI_XPLOR_TOPPAR/protein_rep.param | |

APPENDIX 1-continued

| REMARK 3 | PARAMETER FILE 2: ../parameter.element |
|---|---|
| REMARK 3 | PARAMETER FILE 3: ../cyc.par |
| REMARK 3 | PARAMETER FILE 4: ../../../g2mz/param19.sol |
| REMARK 3 | TOPOLOGY FILE 1: /usr/prop/msi/980/data/xplor/toppar/tophcsdx.pro |
| REMARK 3 | TOPOLOGY FILE 2: ../topology.element |
| REMARK 3 | TOPOLOGY FILE 3: ../cyc.top |
| REMARK 3 | TOPOLOGY FILE 4: ../../../g2mz/toph19.sol |
| REMARK 3 | |
| REMARK 3 | OTHER REFINEMENT REMARKS:     BULK SOLVENT MODEL USED |
| SEQRES 1 A | 100 GLU THR LEU CYS GLY ALA GLU LEU VAL ASP ALA LEU GLN |
| SEQRES 2 A | 100 PHE VAL CYS GLY ASP ARG GLY PHE TYR PHE ASN LYS PRO |
| SEQRES 3 A | 100 THR GLY TYR GLY SER SER THR GLY ILE VAL ASP GLU CYS |
| SEQRES 4 A | 100 CYS PHE ARG SER CYS ASP LEU ARG ARG LEU GLU MET TYR |
| SEQRES 5 A | 100 CYS ALA PRO LEU HOH HOH HOH HOH HOH HOH HOH HOH HOH |
| SEQRES 6 A | 100 HOH HOH HOH HOH HOH HOH HOH HOH HOH HOH HOH HOH HOH |
| SEQRES 7 A | 100 HOH HOH HOH HOH HOH HOH HOH HOH HOH HOH HOH HOH HOH |
| SEQRES 8 A | 100 HOH HOH HOH HOH HOH HOH HOH HOH HOH |
| SEQRES 1 B | 3 CYC BR HOH |
| SSBOND 1 | CYS A 6 CYS A 48 |
| SSBOND 2 | CYS A 18 CYS A 61 |
| SSBOND 3 | CYS A 47 CYS A 52 |
| CRYST1 | 31.830 71.074 66.014 90.00 90.00 90.00 C 2 2 21 16 |
| ORIGX1 | 1.000000 0.000000 0.000000 0.00000 |
| ORIGX2 | 0.000000 1.000000 0.000000 0.00000 |
| ORIGX3 | 0.000000 0.000000 1.000000 0.00000 |
| SCALE1 | 0.031417 0.000000 0.000000 0.00000 |
| SCALE2 | 0.000000 0.014070 0.000000 0.00000 |
| SCALE3 | 0.000000 0.000000 0.015148 0.00000 |
| REMARK | FILENAME="final.pdb" |
| REMARK | r = 0.237371 free_r = 0.26887 |
| REMARK | DATE: Jan. 30, 2001 14:51:37 created by user: mhu |

| ATOM | 1 | CB | GLU | A | 3 | 20.808 | 24.058 | 21.698 | 1.00 | 46.92 |
|---|---|---|---|---|---|---|---|---|---|---|
| ATOM | 2 | CG | GLU | A | 3 | 19.515 | 23.283 | 21.499 | 1.00 | 61.66 |
| ATOM | 3 | CD | GLU | A | 3 | 18.281 | 24.029 | 22.025 | 1.00 | 70.74 |
| ATOM | 4 | OE1 | GLU | A | 3 | 18.254 | 24.408 | 23.221 | 1.00 | 74.11 |
| ATOM | 5 | OE2 | GLU | A | 3 | 17.332 | 24.237 | 21.238 | 1.00 | 75.50 |
| ATOM | 6 | C | GLU | A | 3 | 22.417 | 22.169 | 21.324 | 1.00 | 36.23 |
| ATOM | 7 | O | GLU | A | 3 | 21.616 | 21.223 | 21.375 | 1.00 | 38.90 |
| ATOM | 8 | N | GLU | A | 3 | 21.623 | 23.389 | 19.405 | 1.00 | 38.88 |
| ATOM | 9 | CA | GLU | A | 3 | 21.994 | 23.550 | 20.854 | 1.00 | 40.66 |
| ATOM | 10 | N | THR | A | 4 | 23.696 | 22.040 | 21.647 | 1.00 | 31.38 |
| ATOM | 11 | CA | THR | A | 4 | 24.213 | 20.754 | 22.059 | 1.00 | 24.88 |
| ATOM | 12 | CB | THR | A | 4 | 25.301 | 20.217 | 21.051 | 1.00 | 23.86 |
| ATOM | 13 | OG1 | THR | A | 4 | 26.426 | 21.106 | 21.070 | 1.00 | 30.08 |
| ATOM | 14 | CG2 | THR | A | 4 | 24.786 | 20.115 | 19.645 | 1.00 | 25.92 |
| ATOM | 15 | C | THR | A | 4 | 24.825 | 20.983 | 23.441 | 1.00 | 20.71 |
| ATOM | 16 | O | THR | A | 4 | 24.715 | 22.065 | 24.036 | 1.00 | 19.97 |
| ATOM | 17 | N | LEU | A | 5 | 25.435 | 19.949 | 23.986 | 1.00 | 19.32 |
| ATOM | 18 | CA | LEU | A | 5 | 25.976 | 20.054 | 25.319 | 1.00 | 15.87 |
| ATOM | 19 | CB | LEU | A | 5 | 25.300 | 19.036 | 26.254 | 1.00 | 22.19 |
| ATOM | 20 | CG | LEU | A | 5 | 23.859 | 19.367 | 26.714 | 1.00 | 28.27 |
| ATOM | 21 | CD1 | LEU | A | 5 | 23.229 | 18.123 | 27.479 | 1.00 | 23.45 |
| ATOM | 22 | CD2 | LEU | A | 5 | 23.916 | 20.612 | 27.594 | 1.00 | 25.44 |
| ATOM | 23 | C | LEU | A | 5 | 27.472 | 19.662 | 25.252 | 1.00 | 19.16 |
| ATOM | 24 | O | LEU | A | 5 | 27.742 | 18.527 | 24.980 | 1.00 | 20.58 |
| ATOM | 25 | N | CYS | A | 6 | 28.352 | 20.591 | 25.572 | 1.00 | 19.74 |
| ATOM | 26 | CA | CYS | A | 6 | 29.809 | 20.320 | 25.520 | 1.00 | 21.84 |
| ATOM | 27 | C | CYS | A | 6 | 30.485 | 20.754 | 26.790 | 1.00 | 16.04 |
| ATOM | 28 | O | CYS | A | 6 | 29.990 | 21.602 | 27.535 | 1.00 | 18.05 |
| ATOM | 29 | CB | CYS | A | 6 | 30.448 | 21.077 | 24.361 | 1.00 | 22.37 |
| ATOM | 30 | SG | CYS | A | 6 | 29.753 | 20.589 | 22.733 | 1.00 | 32.91 |
| ATOM | 31 | N | GLY | A | 7 | 31.685 | 20.185 | 27.039 | 1.00 | 19.09 |
| ATOM | 32 | CA | GLY | A | 7 | 32.397 | 20.613 | 28.217 | 1.00 | 17.15 |
| ATOM | 33 | C | GLY | A | 7 | 31.698 | 20.668 | 29.536 | 1.00 | 18.61 |
| ATOM | 34 | O | GLY | A | 7 | 31.069 | 19.683 | 29.965 | 1.00 | 15.50 |
| ATOM | 35 | N | ALA | A | 8 | 31.835 | 21.779 | 30.240 | 1.00 | 13.90 |
| ATOM | 36 | CA | ALA | A | 8 | 31.276 | 21.897 | 31.553 | 1.00 | 15.72 |
| ATOM | 37 | CB | ALA | A | 8 | 31.630 | 23.239 | 32.150 | 1.00 | 21.73 |
| ATOM | 38 | C | ALA | A | 8 | 29.715 | 21.774 | 31.498 | 1.00 | 14.12 |
| ATOM | 39 | O | ALA | A | 8 | 29.116 | 21.316 | 32.469 | 1.00 | 14.45 |
| ATOM | 40 | N | GLU | A | 9 | 29.145 | 22.263 | 30.412 | 1.00 | 15.00 |
| ATOM | 41 | CA | GLU | A | 9 | 27.653 | 22.198 | 30.355 | 1.00 | 21.86 |
| ATOM | 42 | CB | GLU | A | 9 | 27.118 | 22.975 | 29.140 | 1.00 | 23.00 |
| ATOM | 43 | CG | GLU | A | 9 | 27.116 | 24.481 | 29.346 | 1.00 | 33.94 |
| ATOM | 44 | CD | GLU | A | 9 | 26.424 | 25.279 | 28.204 | 1.00 | 53.09 |
| ATOM | 45 | OE1 | GLU | A | 9 | 25.790 | 24.700 | 27.260 | 1.00 | 50.65 |
| ATOM | 46 | OE2 | GLU | A | 9 | 26.521 | 26.528 | 28.270 | 1.00 | 63.42 |
| ATOM | 47 | C | GLU | A | 9 | 27.200 | 20.732 | 30.278 | 1.00 | 19.13 |

APPENDIX 1-continued

| | | | | | | | | | |
|---|---|---|---|---|---|---|---|---|---|
| ATOM | 48 | O | GLU | A | 9 | 26.180 | 20.376 | 30.831 | 1.00 | 15.61 |
| ATOM | 49 | N | LEU | A | 10 | 27.974 | 19.902 | 29.589 | 1.00 | 16.50 |
| ATOM | 50 | CA | LEU | A | 10 | 27.688 | 18.488 | 29.435 | 1.00 | 19.32 |
| ATOM | 51 | CB | LEU | A | 10 | 28.637 | 17.845 | 28.384 | 1.00 | 16.05 |
| ATOM | 52 | CG | LEU | A | 10 | 28.552 | 16.296 | 28.272 | 1.00 | 18.02 |
| ATOM | 53 | CD1 | LEU | A | 10 | 27.080 | 15.875 | 27.864 | 1.00 | 17.22 |
| ATOM | 54 | CD2 | LEU | A | 10 | 29.459 | 15.858 | 27.153 | 1.00 | 17.33 |
| ATOM | 55 | C | LEU | A | 10 | 27.850 | 17.812 | 30.788 | 1.00 | 20.39 |
| ATOM | 56 | O | LEU | A | 10 | 27.030 | 16.968 | 31.173 | 1.00 | 13.49 |
| ATOM | 57 | N | VAL | A | 11 | 28.924 | 18.126 | 31.531 | 1.00 | 16.73 |
| ATOM | 58 | CA | VAL | A | 11 | 29.089 | 17.550 | 32.838 | 1.00 | 13.49 |
| ATOM | 59 | CB | VAL | A | 11 | 30.518 | 17.917 | 33.453 | 1.00 | 16.29 |
| ATOM | 60 | CG1 | VAL | A | 11 | 30.636 | 17.370 | 34.882 | 1.00 | 19.22 |
| ATOM | 61 | CG2 | VAL | A | 11 | 31.603 | 17.350 | 32.528 | 1.00 | 17.93 |
| ATOM | 62 | C | VAL | A | 11 | 28.006 | 18.025 | 33.824 | 1.00 | 13.78 |
| ATOM | 63 | O | VAL | A | 11 | 27.532 | 17.272 | 34.668 | 1.00 | 11.61 |
| ATOM | 64 | N | ASP | A | 12 | 27.599 | 19.280 | 33.717 | 1.00 | 14.34 |
| ATOM | 65 | CA | ASP | A | 12 | 26.573 | 19.795 | 34.651 | 1.00 | 15.14 |
| ATOM | 66 | CB | ASP | A | 12 | 26.166 | 21.243 | 34.290 | 1.00 | 14.66 |
| ATOM | 67 | CG | ASP | A | 12 | 26.960 | 22.337 | 34.970 | 1.00 | 27.52 |
| ATOM | 68 | OD1 | ASP | A | 12 | 27.448 | 22.152 | 36.103 | 1.00 | 29.53 |
| ATOM | 69 | OD2 | ASP | A | 12 | 27.031 | 23.422 | 34.314 | 1.00 | 31.00 |
| ATOM | 70 | C | ASP | A | 12 | 25.275 | 18.941 | 34.366 | 1.00 | 11.41 |
| ATOM | 71 | O | ASP | A | 12 | 24.564 | 18.555 | 35.313 | 1.00 | 14.02 |
| ATOM | 72 | N | ALA | A | 13 | 25.006 | 18.744 | 33.115 | 1.00 | 16.37 |
| ATOM | 73 | CA | ALA | A | 13 | 23.761 | 18.002 | 32.720 | 1.00 | 18.28 |
| ATOM | 74 | CB | ALA | A | 13 | 23.558 | 18.014 | 31.189 | 1.00 | 15.65 |
| ATOM | 75 | C | ALA | A | 13 | 23.803 | 16.590 | 33.235 | 1.00 | 17.95 |
| ATOM | 76 | O | ALA | A | 13 | 22.833 | 16.073 | 33.788 | 1.00 | 15.70 |
| ATOM | 77 | N | LEU | A | 14 | 24.954 | 15.920 | 33.065 | 1.00 | 11.92 |
| ATOM | 78 | CA | LEU | A | 14 | 25.077 | 14.560 | 33.611 | 1.00 | 15.01 |
| ATOM | 79 | CB | LEU | A | 14 | 26.443 | 13.965 | 33.164 | 1.00 | 13.58 |
| ATOM | 80 | CG | LEU | A | 14 | 26.457 | 13.638 | 31.695 | 1.00 | 15.59 |
| ATOM | 81 | CD1 | LEU | A | 14 | 27.939 | 13.345 | 31.250 | 1.00 | 17.99 |
| ATOM | 82 | CD2 | LEU | A | 14 | 25.601 | 12.370 | 31.414 | 1.00 | 22.05 |
| ATOM | 83 | C | LEU | A | 14 | 24.944 | 14.495 | 35.098 | 1.00 | 15.56 |
| ATOM | 84 | O | LEU | A | 14 | 24.341 | 13.550 | 35.626 | 1.00 | 18.96 |
| ATOM | 85 | N | GLN | A | 15 | 25.591 | 15.431 | 35.831 | 1.00 | 12.18 |
| ATOM | 86 | CA | GLN | A | 15 | 25.494 | 15.426 | 37.273 | 1.00 | 14.03 |
| ATOM | 87 | CB | GLN | A | 15 | 26.379 | 16.526 | 37.916 | 1.00 | 17.47 |
| ATOM | 88 | CG | GLN | A | 15 | 27.917 | 16.185 | 37.673 | 1.00 | 23.70 |
| ATOM | 89 | CD | GLN | A | 15 | 28.863 | 16.851 | 38.656 | 1.00 | 32.76 |
| ATOM | 90 | OE1 | GLN | A | 15 | 29.187 | 18.020 | 38.510 | 1.00 | 28.85 |
| ATOM | 91 | NE2 | GLN | A | 15 | 29.314 | 16.095 | 39.658 | 1.00 | 29.69 |
| ATOM | 92 | C | GLN | A | 15 | 24.061 | 15.631 | 37.745 | 1.00 | 18.29 |
| ATOM | 93 | O | GLN | A | 15 | 23.684 | 15.090 | 38.729 | 1.00 | 18.76 |
| ATOM | 94 | N | PHE | A | 16 | 23.297 | 16.400 | 37.012 | 1.00 | 18.23 |
| ATOM | 95 | CA | PHE | A | 16 | 21.916 | 16.692 | 37.438 | 1.00 | 17.04 |
| ATOM | 96 | CB | PHE | A | 16 | 21.438 | 17.935 | 36.706 | 1.00 | 18.66 |
| ATOM | 97 | CG | PHE | A | 16 | 20.060 | 18.334 | 37.110 | 1.00 | 18.49 |
| ATOM | 98 | CD1 | PHE | A | 16 | 19.874 | 18.960 | 38.310 | 1.00 | 23.45 |
| ATOM | 99 | CD2 | PHE | A | 16 | 18.959 | 17.947 | 36.339 | 1.00 | 21.34 |
| ATOM | 100 | CE1 | PHE | A | 16 | 18.558 | 19.216 | 38.788 | 1.00 | 27.25 |
| ATOM | 101 | CE2 | PHE | A | 16 | 17.646 | 18.190 | 36.789 | 1.00 | 21.50 |
| ATOM | 102 | CZ | PHE | A | 16 | 17.457 | 18.829 | 38.020 | 1.00 | 24.95 |
| ATOM | 103 | C | PHE | A | 16 | 21.018 | 15.479 | 37.110 | 1.00 | 15.52 |
| ATOM | 104 | O | PHE | A | 16 | 20.248 | 15.013 | 37.971 | 1.00 | 20.37 |
| ATOM | 105 | N | VAL | A | 17 | 21.160 | 14.923 | 35.916 | 1.00 | 16.12 |
| ATOM | 106 | CA | VAL | A | 17 | 20.338 | 13.761 | 35.490 | 1.00 | 17.94 |
| ATOM | 107 | CB | VAL | A | 17 | 20.392 | 13.598 | 33.932 | 1.00 | 21.28 |
| ATOM | 108 | CG1 | VAL | A | 17 | 19.831 | 12.219 | 33.456 | 1.00 | 25.51 |
| ATOM | 109 | CG2 | VAL | A | 17 | 19.619 | 14.737 | 33.295 | 1.00 | 22.15 |
| ATOM | 110 | C | VAL | A | 17 | 20.720 | 12.454 | 36.182 | 1.00 | 21.98 |
| ATOM | 111 | O | VAL | A | 17 | 19.843 | 11.655 | 36.556 | 1.00 | 24.05 |
| ATOM | 112 | N | CYS | A | 18 | 22.015 | 12.222 | 36.411 | 1.00 | 17.42 |
| ATOM | 113 | CA | CYS | A | 18 | 22.430 | 10.964 | 37.039 | 1.00 | 20.54 |
| ATOM | 114 | C | CYS | A | 18 | 22.420 | 10.998 | 38.579 | 1.00 | 26.67 |
| ATOM | 115 | O | CYS | A | 18 | 22.386 | 9.967 | 39.239 | 1.00 | 24.96 |
| ATOM | 116 | CB | CYS | A | 18 | 23.841 | 10.565 | 36.505 | 1.00 | 16.00 |
| ATOM | 117 | SG | CYS | A | 18 | 23.947 | 10.463 | 34.717 | 1.00 | 29.49 |
| ATOM | 118 | N | GLY | A | 19 | 22.462 | 12.198 | 39.147 | 1.00 | 32.94 |
| ATOM | 119 | CA | GLY | A | 19 | 22.464 | 12.366 | 40.595 | 1.00 | 31.76 |
| ATOM | 120 | C | GLY | A | 19 | 23.563 | 11.580 | 41.263 | 1.00 | 37.69 |
| ATOM | 121 | O | GLY | A | 19 | 24.730 | 11.631 | 40.869 | 1.00 | 40.61 |
| ATOM | 122 | N | ASP | A | 20 | 23.186 | 10.815 | 42.276 | 1.00 | 39.20 |
| ATOM | 123 | CA | ASP | A | 20 | 24.150 | 10.009 | 42.989 | 1.00 | 47.44 |
| ATOM | 124 | CB | ASP | A | 20 | 23.471 | 9.355 | 44.187 | 1.00 | 60.22 |
| ATOM | 125 | CG | ASP | A | 20 | 23.633 | 10.169 | 45.437 | 1.00 | 73.16 |
| ATOM | 126 | OD1 | ASP | A | 20 | 24.132 | 11.311 | 45.326 | 1.00 | 79.05 |

APPENDIX 1-continued

| ATOM | 127 | OD2 | ASP | A | 20 | 23.275 | 9.675 | 46.524 | 1.00 | 78.87 |
|---|---|---|---|---|---|---|---|---|---|---|
| ATOM | 128 | C | ASP | A | 20 | 24.843 | 8.946 | 42.149 | 1.00 | 37.42 |
| ATOM | 129 | O | ASP | A | 20 | 25.954 | 8.521 | 42.472 | 1.00 | 38.02 |
| ATOM | 130 | N | ARG | A | 21 | 24.213 | 8.484 | 41.084 | 1.00 | 26.27 |
| ATOM | 131 | CA | ARG | A | 21 | 24.883 | 7.495 | 40.267 | 1.00 | 33.90 |
| ATOM | 132 | CB | ARG | A | 21 | 23.930 | 6.931 | 39.223 | 1.00 | 36.79 |
| ATOM | 133 | CG | ARG | A | 21 | 22.513 | 7.382 | 39.490 | 1.00 | 50.60 |
| ATOM | 134 | CD | ARG | A | 21 | 21.547 | 6.260 | 39.495 | 1.00 | 46.09 |
| ATOM | 135 | NE | ARG | A | 21 | 21.068 | 5.971 | 38.157 | 1.00 | 44.95 |
| ATOM | 136 | CZ | ARG | A | 21 | 20.533 | 6.865 | 37.329 | 1.00 | 42.44 |
| ATOM | 137 | NH1 | ARG | A | 21 | 20.397 | 8.132 | 37.692 | 1.00 | 49.97 |
| ATOM | 138 | NH2 | ARG | A | 21 | 20.103 | 6.474 | 36.138 | 1.00 | 34.61 |
| ATOM | 139 | C | ARG | A | 21 | 25.951 | 8.301 | 39.565 | 1.00 | 36.17 |
| ATOM | 140 | O | ARG | A | 21 | 25.786 | 9.474 | 39.374 | 1.00 | 37.51 |
| ATOM | 141 | N | GLY | A | 22 | 27.056 | 7.707 | 39.184 | 1.00 | 35.48 |
| ATOM | 142 | CA | GLY | A | 22 | 27.983 | 8.551 | 38.437 | 1.00 | 28.95 |
| ATOM | 143 | C | GLY | A | 22 | 27.566 | 8.445 | 36.983 | 1.00 | 24.58 |
| ATOM | 144 | O | GLY | A | 22 | 26.409 | 8.046 | 36.674 | 1.00 | 22.09 |
| ATOM | 145 | N | PHE | A | 23 | 28.465 | 8.786 | 36.065 | 1.00 | 15.51 |
| ATOM | 146 | CA | PHE | A | 23 | 28.157 | 8.704 | 34.664 | 1.00 | 15.18 |
| ATOM | 147 | CB | PHE | A | 23 | 27.665 | 10.080 | 34.127 | 1.00 | 20.92 |
| ATOM | 148 | CG | PHE | A | 23 | 28.539 | 11.242 | 34.571 | 1.00 | 20.47 |
| ATOM | 149 | CD1 | PHE | A | 23 | 28.271 | 11.908 | 35.762 | 1.00 | 24.30 |
| ATOM | 150 | CD2 | PHE | A | 23 | 29.644 | 11.596 | 33.815 | 1.00 | 20.21 |
| ATOM | 151 | CE1 | PHE | A | 23 | 29.126 | 12.965 | 36.237 | 1.00 | 25.52 |
| ATOM | 152 | CE2 | PHE | A | 23 | 30.520 | 12.636 | 34.261 | 1.00 | 20.52 |
| ATOM | 153 | CZ | PHE | A | 23 | 30.259 | 13.307 | 35.458 | 1.00 | 22.56 |
| ATOM | 154 | C | PHE | A | 23 | 29.397 | 8.332 | 33.920 | 1.00 | 20.77 |
| ATOM | 155 | O | PHE | A | 23 | 30.484 | 8.463 | 34.494 | 1.00 | 24.08 |
| ATOM | 156 | N | TYR | A | 24 | 29.242 | 7.891 | 32.673 | 1.00 | 20.54 |
| ATOM | 157 | CA | TYR | A | 24 | 30.396 | 7.562 | 31.821 | 1.00 | 25.88 |
| ATOM | 158 | CB | TYR | A | 24 | 30.393 | 6.126 | 31.295 | 1.00 | 33.47 |
| ATOM | 159 | CG | TYR | A | 24 | 29.706 | 5.125 | 32.115 | 1.00 | 31.26 |
| ATOM | 160 | CD1 | TYR | A | 24 | 30.356 | 4.551 | 33.204 | 1.00 | 43.74 |
| ATOM | 161 | CE1 | TYR | A | 24 | 29.763 | 3.573 | 33.939 | 1.00 | 47.84 |
| ATOM | 162 | CD2 | TYR | A | 24 | 28.422 | 4.680 | 31.785 | 1.00 | 41.08 |
| ATOM | 163 | CE2 | TYR | A | 24 | 27.818 | 3.692 | 32.524 | 1.00 | 39.08 |
| ATOM | 164 | CZ | TYR | A | 24 | 28.492 | 3.151 | 33.589 | 1.00 | 44.15 |
| ATOM | 165 | OH | TYR | A | 24 | 27.949 | 2.164 | 34.357 | 1.00 | 56.07 |
| ATOM | 166 | C | TYR | A | 24 | 30.332 | 8.362 | 30.588 | 1.00 | 24.71 |
| ATOM | 167 | O | TYR | A | 24 | 29.264 | 8.859 | 30.221 | 1.00 | 31.49 |
| ATOM | 168 | N | PHE | A | 25 | 31.473 | 8.437 | 29.901 | 1.00 | 21.41 |
| ATOM | 169 | CA | PHE | A | 25 | 31.546 | 9.091 | 28.625 | 1.00 | 18.28 |
| ATOM | 170 | CB | PHE | A | 25 | 32.885 | 9.831 | 28.479 | 1.00 | 22.56 |
| ATOM | 171 | CG | PHE | A | 25 | 32.945 | 11.076 | 29.294 | 1.00 | 22.04 |
| ATOM | 172 | CD1 | PHE | A | 25 | 33.336 | 11.040 | 30.625 | 1.00 | 22.70 |
| ATOM | 173 | CD2 | PHE | A | 25 | 32.496 | 12.281 | 28.757 | 1.00 | 29.30 |
| ATOM | 174 | CE1 | PHE | A | 25 | 33.264 | 12.190 | 31.432 | 1.00 | 25.64 |
| ATOM | 175 | CE2 | PHE | A | 25 | 32.415 | 13.440 | 29.557 | 1.00 | 28.31 |
| ATOM | 176 | CZ | PHE | A | 25 | 32.794 | 13.394 | 30.888 | 1.00 | 27.30 |
| ATOM | 177 | C | PHE | A | 25 | 31.385 | 8.046 | 27.534 | 1.00 | 20.94 |
| ATOM | 178 | O | PHE | A | 25 | 30.992 | 8.341 | 26.411 | 1.00 | 21.90 |
| ATOM | 179 | N | ASN | A | 26 | 31.708 | 6.793 | 27.868 | 1.00 | 25.83 |
| ATOM | 180 | CA | ASN | A | 26 | 31.598 | 5.697 | 26.899 | 1.00 | 27.61 |
| ATOM | 181 | CB | ASN | A | 26 | 33.020 | 5.296 | 26.396 | 1.00 | 28.31 |
| ATOM | 182 | CG | ASN | A | 26 | 33.737 | 6.469 | 25.737 | 1.00 | 29.50 |
| ATOM | 183 | OD1 | ASN | A | 26 | 34.438 | 7.267 | 26.395 | 1.00 | 38.35 |
| ATOM | 184 | ND2 | ASN | A | 26 | 33.508 | 6.626 | 24.462 | 1.00 | 32.35 |
| ATOM | 185 | C | ASN | A | 26 | 30.924 | 4.534 | 27.633 | 1.00 | 23.53 |
| ATOM | 186 | O | ASN | A | 26 | 31.274 | 4.214 | 28.753 | 1.00 | 23.60 |
| ATOM | 187 | N | LYS | A | 27 | 29.958 | 3.879 | 27.025 | 1.00 | 26.93 |
| ATOM | 188 | CA | LYS | A | 27 | 29.325 | 2.795 | 27.791 | 1.00 | 33.05 |
| ATOM | 189 | CB | LYS | A | 27 | 28.018 | 2.384 | 27.113 | 1.00 | 34.53 |
| ATOM | 190 | CG | LYS | A | 27 | 27.014 | 3.521 | 27.084 | 1.00 | 37.05 |
| ATOM | 191 | CD | LYS | A | 27 | 26.126 | 3.416 | 25.878 | 1.00 | 39.60 |
| ATOM | 192 | CE | LYS | A | 27 | 24.768 | 4.078 | 26.139 | 1.00 | 42.35 |
| ATOM | 193 | NZ | LYS | A | 27 | 24.244 | 4.674 | 24.865 | 1.00 | 39.82 |
| ATOM | 194 | C | LYS | A | 27 | 30.242 | 1.603 | 27.870 | 1.00 | 31.68 |
| ATOM | 195 | O | LYS | A | 27 | 30.732 | 1.173 | 26.848 | 1.00 | 31.77 |
| ATOM | 196 | N | PRO | A | 28 | 30.494 | 1.065 | 29.073 | 1.00 | 35.47 |
| ATOM | 197 | CD | PRO | A | 28 | 30.001 | 1.491 | 30.392 | 1.00 | 34.96 |
| ATOM | 198 | CA | PRO | A | 28 | 31.388 | −0.110 | 29.148 | 1.00 | 36.66 |
| ATOM | 199 | CB | PRO | A | 28 | 31.468 | −0.435 | 30.637 | 1.00 | 40.26 |
| ATOM | 200 | CG | PRO | A | 28 | 30.367 | 0.359 | 31.287 | 1.00 | 40.80 |
| ATOM | 201 | C | PRO | A | 28 | 30.784 | −1.252 | 28.322 | 1.00 | 36.18 |
| ATOM | 202 | O | PRO | A | 28 | 29.558 | −1.344 | 28.152 | 1.00 | 36.79 |
| ATOM | 203 | N | THR | A | 29 | 31.614 | −2.107 | 27.763 | 1.00 | 34.63 |
| ATOM | 204 | CA | THR | A | 29 | 31.026 | −3.155 | 26.945 | 1.00 | 41.92 |
| ATOM | 205 | CB | THR | A | 29 | 31.824 | −3.391 | 25.661 | 1.00 | 51.94 |

APPENDIX 1-continued

| ATOM | 206 | OG1 | THR | A | 29 | 32.938 | −4.249 | 25.947 | 1.00 | 52.79 |
|---|---|---|---|---|---|---|---|---|---|---|
| ATOM | 207 | CG2 | THR | A | 29 | 32.313 | −2.071 | 25.086 | 1.00 | 55.75 |
| ATOM | 208 | C | THR | A | 29 | 30.897 | −4.498 | 27.635 | 1.00 | 35.36 |
| ATOM | 209 | O | THR | A | 29 | 30.068 | −5.322 | 27.238 | 1.00 | 34.58 |
| ATOM | 210 | N | GLY | A | 30 | 31.721 | −4.720 | 28.643 | 1.00 | 33.36 |
| ATOM | 211 | CA | GLY | A | 30 | 31.659 | −5.997 | 29.323 | 1.00 | 33.97 |
| ATOM | 212 | C | GLY | A | 30 | 32.109 | −7.243 | 28.536 | 1.00 | 31.86 |
| ATOM | 213 | O | GLY | A | 30 | 32.227 | −7.275 | 27.305 | 1.00 | 34.94 |
| ATOM | 214 | N | TYR | A | 31 | 32.265 | −8.325 | 29.275 | 1.00 | 23.05 |
| ATOM | 215 | CA | TYR | A | 31 | 32.723 | −9.576 | 28.690 | 1.00 | 25.72 |
| ATOM | 216 | CB | TYR | A | 31 | 33.144 | −10.505 | 29.813 | 1.00 | 21.15 |
| ATOM | 217 | CG | TYR | A | 31 | 34.274 | −9.992 | 30.633 | 1.00 | 24.03 |
| ATOM | 218 | CD1 | TYR | A | 31 | 34.066 | −9.497 | 31.892 | 1.00 | 17.01 |
| ATOM | 219 | CE1 | TYR | A | 31 | 35.106 | −8.997 | 32.644 | 1.00 | 26.09 |
| ATOM | 220 | CD2 | TYR | A | 31 | 35.579 | −9.983 | 30.121 | 1.00 | 29.13 |
| ATOM | 221 | CE2 | TYR | A | 31 | 36.616 | −9.502 | 30.870 | 1.00 | 25.81 |
| ATOM | 222 | CZ | TYR | A | 31 | 36.383 | −9.009 | 32.115 | 1.00 | 25.77 |
| ATOM | 223 | OH | TYR | A | 31 | 37.419 | −8.560 | 32.875 | 1.00 | 34.26 |
| ATOM | 224 | C | TYR | A | 31 | 31.678 | −10.274 | 27.840 | 1.00 | 29.45 |
| ATOM | 225 | O | TYR | A | 31 | 30.468 | −10.172 | 28.112 | 1.00 | 30.08 |
| ATOM | 226 | N | GLY | A | 32 | 32.141 | −10.990 | 26.808 | 1.00 | 29.62 |
| ATOM | 227 | CA | GLY | A | 32 | 31.228 | −11.746 | 25.972 | 1.00 | 33.28 |
| ATOM | 228 | C | GLY | A | 32 | 30.235 | −10.912 | 25.198 | 1.00 | 36.13 |
| ATOM | 229 | O | GLY | A | 32 | 29.161 | −11.380 | 24.832 | 1.00 | 32.23 |
| ATOM | 230 | N | SER | A | 33 | 30.606 | −9.668 | 24.937 | 1.00 | 41.08 |
| ATOM | 231 | CA | SER | A | 33 | 29.722 | −8.787 | 24.217 | 1.00 | 47.10 |
| ATOM | 232 | CB | SER | A | 33 | 30.130 | −7.331 | 24.386 | 1.00 | 46.73 |
| ATOM | 233 | OG | SER | A | 33 | 29.397 | −6.557 | 23.463 | 1.00 | 52.64 |
| ATOM | 234 | C | SER | A | 33 | 29.816 | −9.142 | 22.764 | 1.00 | 57.93 |
| ATOM | 235 | O | SER | A | 33 | 30.807 | −9.735 | 22.317 | 1.00 | 57.01 |
| ATOM | 236 | N | SER | A | 34 | 28.772 | −8.755 | 22.039 | 1.00 | 65.04 |
| ATOM | 237 | CA | SER | A | 34 | 28.657 | −8.989 | 20.613 | 1.00 | 70.41 |
| ATOM | 238 | CB | SER | A | 34 | 28.414 | −7.659 | 19.899 | 1.00 | 72.65 |
| ATOM | 239 | OG | SER | A | 34 | 27.049 | −7.299 | 19.995 | 1.00 | 72.85 |
| ATOM | 240 | C | SER | A | 34 | 29.885 | −9.671 | 20.028 | 1.00 | 71.58 |
| ATOM | 241 | O | SER | A | 34 | 30.642 | −9.053 | 19.289 | 1.00 | 69.77 |
| ATOM | 242 | CB | THR | A | 41 | 30.810 | 6.812 | 19.043 | 1.00 | 59.11 |
| ATOM | 243 | OG1 | THR | A | 41 | 29.666 | 5.952 | 18.975 | 1.00 | 64.04 |
| ATOM | 244 | CG2 | THR | A | 41 | 31.511 | 6.892 | 17.700 | 1.00 | 59.18 |
| ATOM | 245 | C | THR | A | 41 | 31.044 | 6.416 | 21.449 | 1.00 | 51.54 |
| ATOM | 246 | O | THR | A | 41 | 30.689 | 5.415 | 22.079 | 1.00 | 55.44 |
| ATOM | 247 | N | THR | A | 41 | 32.206 | 4.887 | 19.817 | 1.00 | 58.60 |
| ATOM | 248 | CA | THR | A | 41 | 31.763 | 6.289 | 20.105 | 1.00 | 57.60 |
| ATOM | 249 | N | GLY | A | 42 | 30.804 | 7.654 | 21.870 | 1.00 | 35.08 |
| ATOM | 250 | CA | GLY | A | 42 | 30.159 | 7.853 | 23.151 | 1.00 | 21.75 |
| ATOM | 251 | C | GLY | A | 42 | 29.409 | 9.184 | 23.225 | 1.00 | 18.36 |
| ATOM | 252 | O | GLY | A | 42 | 29.011 | 9.724 | 22.200 | 1.00 | 21.32 |
| ATOM | 253 | N | ILE | A | 43 | 29.298 | 9.708 | 24.431 | 1.00 | 21.07 |
| ATOM | 254 | CA | ILE | A | 43 | 28.475 | 10.899 | 24.619 | 1.00 | 22.17 |
| ATOM | 255 | CB | ILE | A | 43 | 28.247 | 11.113 | 26.148 | 1.00 | 18.01 |
| ATOM | 256 | CG2 | ILE | A | 43 | 29.474 | 11.764 | 26.819 | 1.00 | 20.05 |
| ATOM | 257 | CG1 | ILE | A | 43 | 27.124 | 12.102 | 26.413 | 1.00 | 20.02 |
| ATOM | 258 | CD1 | ILE | A | 43 | 26.793 | 12.170 | 27.882 | 1.00 | 22.13 |
| ATOM | 259 | C | ILE | A | 43 | 28.947 | 12.145 | 23.921 | 1.00 | 25.61 |
| ATOM | 260 | O | ILE | A | 43 | 28.118 | 12.955 | 23.466 | 1.00 | 18.04 |
| ATOM | 261 | N | VAL | A | 44 | 30.260 | 12.336 | 23.748 | 1.00 | 19.35 |
| ATOM | 262 | CA | VAL | A | 44 | 30.629 | 13.560 | 23.090 | 1.00 | 19.83 |
| ATOM | 263 | CB | VAL | A | 44 | 32.187 | 13.809 | 23.157 | 1.00 | 22.51 |
| ATOM | 264 | CG1 | VAL | A | 44 | 32.587 | 14.916 | 22.238 | 1.00 | 29.90 |
| ATOM | 265 | CG2 | VAL | A | 44 | 32.568 | 14.056 | 24.605 | 1.00 | 22.31 |
| ATOM | 266 | C | VAL | A | 44 | 30.137 | 13.492 | 21.655 | 1.00 | 18.37 |
| ATOM | 267 | O | VAL | A | 44 | 29.664 | 14.477 | 21.127 | 1.00 | 20.08 |
| ATOM | 268 | N | ASP | A | 45 | 30.257 | 12.308 | 21.027 | 1.00 | 19.78 |
| ATOM | 269 | CA | ASP | A | 45 | 29.821 | 12.142 | 19.657 | 1.00 | 22.36 |
| ATOM | 270 | CB | ASP | A | 45 | 30.132 | 10.738 | 19.207 | 1.00 | 29.90 |
| ATOM | 271 | CG | ASP | A | 45 | 31.588 | 10.395 | 19.435 | 1.00 | 38.30 |
| ATOM | 272 | OD1 | ASP | A | 45 | 32.374 | 10.700 | 18.516 | 1.00 | 34.84 |
| ATOM | 273 | OD2 | ASP | A | 45 | 31.929 | 9.881 | 20.546 | 1.00 | 39.04 |
| ATOM | 274 | C | ASP | A | 45 | 28.304 | 12.345 | 19.531 | 1.00 | 23.03 |
| ATOM | 275 | O | ASP | A | 45 | 27.830 | 13.023 | 18.613 | 1.00 | 22.16 |
| ATOM | 276 | N | GLU | A | 46 | 27.610 | 11.772 | 20.489 | 1.00 | 21.13 |
| ATOM | 277 | CA | GLU | A | 46 | 26.139 | 11.784 | 20.505 | 1.00 | 24.96 |
| ATOM | 278 | CB | GLU | A | 46 | 25.676 | 10.660 | 21.418 | 1.00 | 32.84 |
| ATOM | 279 | CG | GLU | A | 46 | 24.220 | 10.314 | 21.307 | 1.00 | 38.09 |
| ATOM | 280 | CD | GLU | A | 46 | 23.877 | 8.973 | 21.913 | 1.00 | 41.51 |
| ATOM | 281 | OE1 | GLU | A | 46 | 24.713 | 8.378 | 22.621 | 1.00 | 41.76 |
| ATOM | 282 | OE2 | GLU | A | 46 | 22.739 | 8.505 | 21.689 | 1.00 | 45.60 |
| ATON | 283 | C | GLU | A | 46 | 25.472 | 13.084 | 20.952 | 1.00 | 24.92 |
| ATON | 284 | O | GLU | A | 46 | 24.450 | 13.450 | 20.376 | 1.00 | 23.35 |

APPENDIX 1-continued

| | | | | | | | | | | |
|---|---|---|---|---|---|---|---|---|---|---|
| ATOM | 285 | N | CYS | A | 47 | 26.045 | 13.747 | 21.970 | 1.00 | 20.20 |
| ATOM | 286 | CA | CYS | A | 47 | 25.477 | 14.961 | 22.590 | 1.00 | 19.56 |
| ATOM | 287 | C | CYS | A | 47 | 26.174 | 16.282 | 22.474 | 1.00 | 28.23 |
| ATOM | 288 | O | CYS | A | 47 | 25.563 | 17.328 | 22.769 | 1.00 | 21.99 |
| ATOM | 289 | CB | CYS | A | 47 | 25.240 | 14.687 | 24.091 | 1.00 | 21.60 |
| ATOM | 290 | SG | CYS | A | 47 | 24.245 | 13.186 | 24.373 | 1.00 | 26.79 |
| ATOM | 291 | N | CYS | A | 48 | 27.452 | 16.263 | 22.074 | 1.00 | 18.45 |
| ATOM | 292 | CA | CYS | A | 48 | 28.181 | 17.537 | 21.940 | 1.00 | 17.21 |
| ATOM | 293 | C | CYS | A | 48 | 28.382 | 17.818 | 20.473 | 1.00 | 19.88 |
| ATOM | 294 | O | CYS | A | 48 | 28.082 | 18.890 | 20.040 | 1.00 | 23.54 |
| ATOM | 295 | CB | CYS | A | 48 | 29.521 | 17.456 | 22.686 | 1.00 | 22.56 |
| ATOM | 296 | SG | CYS | A | 48 | 30.678 | 18.814 | 22.279 | 1.00 | 25.89 |
| ATOM | 297 | N | PHE | A | 49 | 28.854 | 16.830 | 19.706 | 1.00 | 19.44 |
| ATOM | 298 | CA | PHE | A | 49 | 29.044 | 17.010 | 18.279 | 1.00 | 26.47 |
| ATOM | 299 | CB | PHE | A | 49 | 29.939 | 15.912 | 17.710 | 1.00 | 27.72 |
| ATOM | 300 | CG | PHE | A | 49 | 31.343 | 15.940 | 18.268 | 1.00 | 32.07 |
| ATOM | 301 | CD1 | PHE | A | 49 | 32.098 | 14.764 | 18.363 | 1.00 | 31.76 |
| ATOM | 302 | CD2 | PHE | A | 49 | 31.902 | 17.133 | 18.703 | 1.00 | 29.85 |
| ATOM | 303 | CE1 | PHE | A | 49 | 33.396 | 14.798 | 18.889 | 1.00 | 32.64 |
| ATOM | 304 | CE2 | PHE | A | 49 | 33.203 | 17.153 | 19.230 | 1.00 | 29.98 |
| ATOM | 305 | CZ | PHE | A | 49 | 33.938 | 15.987 | 19.320 | 1.00 | 24.87 |
| ATOM | 306 | C | PHE | A | 49 | 27.706 | 17.000 | 17.573 | 1.00 | 27.42 |
| ATOM | 307 | O | PHE | A | 49 | 27.561 | 17.598 | 16.517 | 1.00 | 31.83 |
| ATOM | 308 | N | ARG | A | 50 | 26.744 | 16.298 | 18.167 | 1.00 | 29.59 |
| ATOM | 309 | CA | ARG | A | 50 | 25.381 | 16.219 | 17.640 | 1.00 | 26.05 |
| ATOM | 310 | CB | ARG | A | 50 | 25.106 | 14.832 | 17.157 | 1.00 | 23.82 |
| ATOM | 311 | CG | ARG | A | 50 | 25.916 | 14.488 | 15.899 | 1.00 | 26.06 |
| ATOM | 312 | CD | ARG | A | 50 | 25.953 | 13.031 | 15.742 | 1.00 | 29.51 |
| ATOM | 313 | NE | ARG | A | 50 | 26.583 | 12.750 | 14.479 | 1.00 | 39.53 |
| ATOM | 314 | CZ | ARG | A | 50 | 27.849 | 12.386 | 14.370 | 1.00 | 41.06 |
| ATOM | 315 | NH1 | ARG | A | 50 | 28.603 | 12.260 | 15.466 | 1.00 | 40.37 |
| ATOM | 316 | NH2 | ARG | A | 50 | 28.354 | 12.198 | 13.163 | 1.00 | 40.98 |
| ATOM | 317 | C | ARG | A | 50 | 24.434 | 16.539 | 18.794 | 1.00 | 25.89 |
| ATOM | 318 | O | ARG | A | 50 | 24.864 | 16.563 | 19.966 | 1.00 | 19.42 |
| ATOM | 319 | N | SER | A | 51 | 23.161 | 16.811 | 18.501 | 1.00 | 25.83 |
| ATOM | 320 | CA | SER | A | 51 | 22.229 | 17.080 | 19.633 | 1.00 | 28.49 |
| ATOM | 321 | CB | SER | A | 51 | 21.122 | 18.082 | 19.248 | 1.00 | 29.44 |
| ATOM | 322 | OG | SER | A | 51 | 20.679 | 17.787 | 17.954 | 1.00 | 42.62 |
| ATOM | 323 | C | SER | A | 51 | 21.569 | 15.761 | 20.025 | 1.00 | 22.34 |
| ATOM | 324 | O | SER | A | 51 | 21.229 | 14.963 | 19.164 | 1.00 | 28.05 |
| ATOM | 325 | N | CYS | A | 52 | 21.385 | 15.517 | 21.325 | 1.00 | 21.96 |
| ATOM | 326 | CA | CYS | A | 52 | 20.771 | 14.278 | 21.762 | 1.00 | 24.73 |
| ATOM | 327 | C | CYS | A | 52 | 19.637 | 14.683 | 22.708 | 1.00 | 25.51 |
| ATOM | 328 | O | CYS | A | 52 | 19.616 | 15.780 | 23.240 | 1.00 | 23.80 |
| ATOM | 329 | CB | CYS | A | 52 | 21.791 | 13.373 | 22.494 | 1.00 | 24.55 |
| ATOM | 330 | SG | CYS | A | 52 | 22.331 | 13.922 | 24.151 | 1.00 | 28.05 |
| ATOM | 331 | N | ASP | A | 53 | 18.671 | 13.815 | 22.896 | 1.00 | 27.35 |
| ATOM | 332 | CA | ASP | A | 53 | 17.622 | 14.228 | 23.789 | 1.00 | 28.62 |
| ATOM | 333 | CB | ASP | A | 53 | 16.248 | 13.872 | 23.201 | 1.00 | 34.84 |
| ATOM | 334 | CG | ASP | A | 53 | 16.078 | 12.408 | 22.968 | 1.00 | 39.80 |
| ATOM | 335 | OD1 | ASP | A | 53 | 16.598 | 11.616 | 23.782 | 1.00 | 44.65 |
| ATOM | 336 | OD2 | ASP | A | 53 | 15.413 | 12.052 | 21.965 | 1.00 | 46.35 |
| ATOM | 337 | C | ASP | A | 53 | 17.848 | 13.616 | 25.147 | 1.00 | 23.60 |
| ATOM | 338 | O | ASP | A | 53 | 18.735 | 12.762 | 25.324 | 1.00 | 21.40 |
| ATOM | 339 | N | LEU | A | 54 | 17.012 | 14.005 | 26.099 | 1.00 | 20.38 |
| ATOM | 340 | CA | LEU | A | 54 | 17.163 | 13.558 | 27.477 | 1.00 | 14.25 |
| ATOM | 341 | CB | LEU | A | 54 | 16.015 | 14.169 | 28.329 | 1.00 | 21.53 |
| ATOM | 342 | CG | LEU | A | 54 | 16.024 | 13.807 | 29.805 | 1.00 | 22.22 |
| ATOM | 343 | CD1 | LEU | A | 54 | 17.283 | 14.383 | 30.476 | 1.00 | 21.85 |
| ATOM | 344 | CD2 | LEU | A | 54 | 14.733 | 14.336 | 30.497 | 1.00 | 20.36 |
| ATOM | 345 | C | LEU | A | 54 | 17.276 | 12.046 | 27.683 | 1.00 | 23.79 |
| ATOM | 346 | O | LEU | A | 54 | 18.075 | 11.598 | 28.496 | 1.00 | 23.74 |
| ATOM | 347 | N | ARG | A | 55 | 16.449 | 11.253 | 26.978 | 1.00 | 23.24 |
| ATOM | 348 | CA | ARG | A | 55 | 16.489 | 9.795 | 27.104 | 1.00 | 26.67 |
| ATOM | 349 | CB | ARG | A | 55 | 15.469 | 9.140 | 26.140 | 1.00 | 33.74 |
| ATOM | 350 | CG | ARG | A | 55 | 14.013 | 9.234 | 26.618 | 1.00 | 47.08 |
| ATOM | 351 | CD | ARG | A | 55 | 13.838 | 8.500 | 27.974 | 1.00 | 59.43 |
| ATOM | 352 | NE | ARG | A | 55 | 13.580 | 9.398 | 29.104 | 1.00 | 68.64 |
| ATOM | 353 | CZ | ARG | A | 55 | 14.359 | 9.527 | 30.182 | 1.00 | 73.73 |
| ATOM | 354 | NH1 | ARG | A | 55 | 15.485 | 8.813 | 30.302 | 1.00 | 74.93 |
| ATOM | 355 | NH2 | ARG | A | 55 | 14.028 | 10.401 | 31.134 | 1.00 | 72.23 |
| ATOM | 356 | C | ARG | A | 55 | 17.876 | 9.229 | 26.774 | 1.00 | 25.72 |
| ATOM | 357 | O | ARG | A | 55 | 18.365 | 8.348 | 27.470 | 1.00 | 28.77 |
| ATOM | 358 | N | ARG | A | 56 | 18.482 | 9.765 | 25.726 | 1.00 | 21.19 |
| ATOM | 359 | CA | ARG | A | 56 | 19.785 | 9.285 | 25.276 | 1.00 | 27.70 |
| ATOM | 360 | CB | ARG | A | 56 | 20.049 | 9.798 | 23.892 | 1.00 | 35.27 |
| ATOM | 361 | CG | ARG | A | 56 | 19.140 | 9.134 | 22.892 | 1.00 | 42.72 |
| ATOM | 362 | CD | ARG | A | 56 | 19.352 | 7.624 | 22.897 | 1.00 | 52.32 |
| ATOM | 363 | NE | ARG | A | 56 | 20.565 | 7.280 | 22.150 | 1.00 | 59.61 |

APPENDIX 1-continued

| | | | | | | | | | |
|---|---|---|---|---|---|---|---|---|---|
| ATOM | 364 | CZ | ARG | A | 56 | 21.142 | 6.075 | 22.108 | 1.00 | 61.66 |
| ATOM | 365 | NH1 | ARG | A | 56 | 20.646 | 5.046 | 22.789 | 1.00 | 64.42 |
| ATOM | 366 | NH2 | ARG | A | 56 | 22.244 | 5.906 | 21.389 | 1.00 | 62.77 |
| ATOM | 367 | C | ARG | A | 56 | 20.850 | 9.724 | 26.246 | 1.00 | 25.14 |
| ATOM | 368 | O | ARG | A | 56 | 21.755 | 8.952 | 26.618 | 1.00 | 25.99 |
| ATOM | 369 | N | LEU | A | 57 | 20.743 | 10.967 | 26.689 | 1.00 | 21.87 |
| ATOM | 370 | CA | LEU | A | 57 | 21.684 | 11.448 | 27.701 | 1.00 | 22.79 |
| ATOM | 371 | CB | LEU | A | 57 | 21.367 | 12.923 | 28.059 | 1.00 | 22.01 |
| ATOM | 372 | CG | LEU | A | 57 | 22.188 | 13.715 | 29.089 | 1.00 | 22.86 |
| ATOM | 373 | CD1 | LEU | A | 57 | 21.537 | 15.099 | 29.190 | 1.00 | 27.83 |
| ATOM | 374 | CD2 | LEU | A | 57 | 22.115 | 13.120 | 30.453 | 1.00 | 32.64 |
| ATOM | 375 | C | LEU | A | 57 | 21.665 | 10.578 | 28.970 | 1.00 | 20.53 |
| ATOM | 376 | O | LEU | A | 57 | 22.720 | 10.208 | 29.525 | 1.00 | 19.79 |
| ATOM | 377 | N | GLU | A | 58 | 20.486 | 10.199 | 29.479 | 1.00 | 18.07 |
| ATOM | 378 | CA | GLU | A | 58 | 20.425 | 9.390 | 30.682 | 1.00 | 17.97 |
| ATOM | 379 | CB | GLU | A | 58 | 18.951 | 9.351 | 31.198 | 1.00 | 24.34 |
| ATOM | 380 | CG | GLU | A | 58 | 18.883 | 8.941 | 32.660 | 1.00 | 36.31 |
| ATOM | 381 | CD | GLU | A | 58 | 17.473 | 9.016 | 33.227 | 1.00 | 41.86 |
| ATOM | 382 | OE1 | GLU | A | 58 | 17.316 | 8.902 | 34.474 | 1.00 | 39.29 |
| ATOM | 383 | OE2 | GLU | A | 58 | 16.549 | 9.198 | 32.406 | 1.00 | 36.76 |
| ATOM | 384 | C | GLU | A | 58 | 21.005 | 7.942 | 30.537 | 1.00 | 14.19 |
| ATOM | 385 | O | GLU | A | 58 | 21.331 | 7.279 | 31.508 | 1.00 | 26.60 |
| ATOM | 386 | N | MET | A | 59 | 21.172 | 7.487 | 29.307 | 1.00 | 15.83 |
| ATOM | 387 | CA | MET | A | 59 | 21.767 | 6.166 | 29.115 | 1.00 | 21.59 |
| ATOM | 388 | CB | MET | A | 59 | 21.626 | 5.746 | 27.672 | 1.00 | 23.71 |
| ATOM | 389 | CG | MET | A | 59 | 20.195 | 5.145 | 27.372 | 1.00 | 27.46 |
| ATOM | 390 | SD | MET | A | 59 | 19.916 | 5.067 | 25.648 | 1.00 | 38.20 |
| ATOM | 391 | CE | MET | A | 59 | 18.000 | 5.126 | 25.597 | 1.00 | 38.66 |
| ATOM | 392 | C | MET | A | 59 | 23.261 | 6.169 | 29.521 | 1.00 | 23.34 |
| ATOM | 393 | O | MET | A | 59 | 23.859 | 5.124 | 29.663 | 1.00 | 25.38 |
| ATOM | 394 | N | TYR | A | 60 | 23.847 | 7.353 | 29.726 | 1.00 | 19.16 |
| ATOM | 395 | CA | TYR | A | 60 | 25.266 | 7.386 | 30.144 | 1.00 | 18.17 |
| ATOM | 396 | CB | TYR | A | 60 | 25.982 | 8.549 | 29.452 | 1.00 | 18.20 |
| ATOM | 397 | CG | TYR | A | 60 | 26.144 | 8.364 | 27.992 | 1.00 | 20.05 |
| ATOM | 398 | CD1 | TYR | A | 60 | 25.193 | 8.855 | 27.086 | 1.00 | 20.40 |
| ATOM | 399 | CE1 | TYR | A | 60 | 25.339 | 8.675 | 25.713 | 1.00 | 22.99 |
| ATOM | 400 | CD2 | TYR | A | 60 | 27.245 | 7.686 | 27.482 | 1.00 | 23.58 |
| ATOM | 401 | CE2 | TYR | A | 60 | 27.398 | 7.501 | 26.131 | 1.00 | 24.88 |
| ATOM | 402 | CZ | TYR | A | 60 | 26.475 | 7.980 | 25.258 | 1.00 | 25.27 |
| ATOM | 403 | OH | TYR | A | 60 | 26.676 | 7.780 | 23.940 | 1.00 | 24.52 |
| ATOM | 404 | C | TYR | A | 60 | 25.406 | 7.424 | 31.634 | 1.00 | 22.93 |
| ATOM | 405 | O | TYR | A | 60 | 26.519 | 7.507 | 32.199 | 1.00 | 22.51 |
| ATOM | 406 | N | CYS | A | 61 | 24.290 | 7.385 | 32.352 | 1.00 | 18.42 |
| ATOM | 407 | CA | CYS | A | 61 | 24.402 | 7.303 | 33.809 | 1.00 | 15.63 |
| ATOM | 408 | C | CYS | A | 61 | 24.808 | 5.872 | 34.207 | 1.00 | 19.70 |
| ATOM | 409 | O | CYS | A | 61 | 24.394 | 4.908 | 33.563 | 1.00 | 25.04 |
| ATOM | 410 | CB | CYS | A | 61 | 23.065 | 7.562 | 34.511 | 1.00 | 22.45 |
| ATOM | 411 | SG | CYS | A | 61 | 22.415 | 9.181 | 34.212 | 1.00 | 24.27 |
| ATOM | 412 | N | ALA | A | 62 | 25.543 | 5.738 | 35.298 | 1.00 | 24.74 |
| ATOM | 413 | CA | ALA | A | 62 | 26.004 | 4.424 | 35.756 | 1.00 | 31.14 |
| ATOM | 414 | CB | ALA | A | 62 | 27.273 | 4.588 | 36.641 | 1.00 | 24.85 |
| ATOM | 415 | C | ALA | A | 62 | 24.902 | 3.747 | 36.563 | 1.00 | 36.05 |
| ATOM | 416 | O | ALA | A | 62 | 23.920 | 4.394 | 36.962 | 1.00 | 33.02 |
| ATOM | 417 | N | PRO | A | 63 | 25.014 | 2.427 | 36.780 | 1.00 | 44.06 |
| ATOM | 418 | CD | PRO | A | 63 | 26.021 | 1.447 | 36.310 | 1.00 | 47.05 |
| ATOM | 419 | CA | PRO | A | 63 | 23.942 | 1.803 | 37.576 | 1.00 | 46.88 |
| ATOM | 420 | CB | PRO | A | 63 | 24.182 | 0.296 | 37.393 | 1.00 | 47.68 |
| ATOM | 421 | CG | PRO | A | 63 | 25.651 | 0.166 | 37.068 | 1.00 | 49.88 |
| ATOM | 422 | C | PRO | A | 63 | 24.111 | 2.253 | 39.027 | 1.00 | 48.13 |
| ATOM | 423 | O | PRO | A | 63 | 23.135 | 2.412 | 39.773 | 1.00 | 54.36 |
| ATOM | 424 | N | LEU | A | 64 | 25.379 | 2.467 | 39.379 | 1.00 | 51.56 |
| ATOM | 425 | CA | LEU | A | 64 | 25.835 | 2.896 | 40.693 | 1.00 | 61.37 |
| ATOM | 426 | CB | LEU | A | 64 | 26.997 | 1.994 | 41.170 | 1.00 | 63.79 |
| ATOM | 427 | CG | LEU | A | 64 | 26.761 | 0.984 | 42.312 | 1.00 | 60.23 |
| ATOM | 428 | CD1 | LEU | A | 64 | 26.872 | −0.435 | 41.767 | 1.00 | 61.06 |
| ATOM | 429 | CD2 | LEU | A | 64 | 27.781 | 1.210 | 43.447 | 1.00 | 58.43 |
| ATOM | 430 | C | LEU | A | 64 | 26.327 | 4.343 | 40.607 | 1.00 | 67.33 |
| ATOM | 431 | O | LEU | A | 64 | 27.441 | 4.612 | 40.132 | 1.00 | 71.54 |
| ATOM | 432 | C1 | CYC | A | 1 | 19.808 | 21.082 | 25.297 | 1.00 | 29.47 |
| ATOM | 433 | C6 | CYC | A | 1 | 19.974 | 19.730 | 24.564 | 1.00 | 31.45 |
| ATOM | 434 | O21 | CYC | A | 1 | 21.316 | 19.561 | 24.000 | 1.00 | 30.05 |
| ATOM | 435 | C5 | CYC | A | 1 | 19.707 | 18.570 | 25.545 | 1.00 | 24.70 |
| ATOM | 436 | C4 | CYC | A | 1 | 18.349 | 18.647 | 26.185 | 1.00 | 28.97 |
| ATOM | 437 | C11 | CYC | A | 1 | 18.069 | 17.503 | 27.203 | 1.00 | 25.55 |
| ATOM | 438 | C10 | CYC | A | 1 | 18.915 | 17.625 | 28.449 | 1.00 | 26.59 |
| ATOM | 439 | C9 | CYC | A | 1 | 18.774 | 19.062 | 29.167 | 1.00 | 22.28 |
| ATOM | 440 | C15 | CYC | A | 1 | 19.668 | 19.202 | 30.407 | 1.00 | 18.50 |
| ATOM | 441 | C18 | CYC | A | 1 | 19.488 | 18.173 | 31.529 | 1.00 | 17.96 |
| ATOM | 442 | C17 | CYC | A | 1 | 20.033 | 18.861 | 32.738 | 1.00 | 20.63 |

APPENDIX 1-continued

| ATOM | 443 | C16 | CYC | A | 1 | 20.478 | 20.370 | 32.210 | 1.00 | 19.19 |
|---|---|---|---|---|---|---|---|---|---|---|
| ATOM | 444 | C43 | CYC | A | 1 | 20.408 | 21.271 | 33.357 | 1.00 | 17.91 |
| ATOM | 445 | C55 | CYC | A | 1 | 21.476 | 20.723 | 34.438 | 1.00 | 26.47 |
| ATOM | 446 | C56 | CYC | B | 1 | 21.498 | 21.442 | 35.738 | 1.00 | 31.90 |
| ATOM | 447 | C57 | CYC | B | 1 | 22.417 | 22.653 | 36.015 | 1.00 | 39.26 |
| ATOM | 448 | N59 | CYC | B | 1 | 22.473 | 23.332 | 37.133 | 1.00 | 46.97 |
| ATOM | 449 | C74 | CYC | B | 1 | 23.443 | 24.507 | 37.216 | 1.00 | 56.76 |
| ATOM | 450 | C75 | CYC | B | 1 | 22.897 | 25.835 | 36.400 | 1.00 | 62.01 |
| ATOM | 451 | C76 | CYC | B | 1 | 23.920 | 27.038 | 36.528 | 1.00 | 66.74 |
| ATOM | 452 | N77 | CYC | B | 1 | 23.715 | 27.349 | 37.968 | 1.00 | 68.00 |
| ATOM | 453 | C78 | CYC | B | 1 | 24.623 | 27.135 | 39.017 | 1.00 | 72.42 |
| ATOM | 454 | C80 | CYC | B | 1 | 24.134 | 27.596 | 40.383 | 1.00 | 76.46 |
| ATOM | 455 | O86 | CYC | B | 1 | 22.731 | 28.037 | 40.272 | 1.00 | 73.13 |
| ATOM | 456 | C81 | CYC | B | 1 | 25.194 | 28.755 | 40.862 | 1.00 | 85.35 |
| ATOM | 457 | O87 | CYC | B | 1 | 25.451 | 29.858 | 39.876 | 1.00 | 86.13 |
| ATOM | 458 | C82 | CYC | B | 1 | 24.767 | 29.384 | 42.284 | 1.00 | 92.20 |
| ATOM | 459 | O88 | CYC | B | 1 | 23.400 | 29.939 | 42.115 | 1.00 | 92.22 |
| ATOM | 460 | C83 | CYC | B | 1 | 25.777 | 30.529 | 42.728 | 1.00 | 96.59 |
| ATOM | 461 | O89 | CYC | B | 1 | 27.124 | 29.924 | 42.873 | 1.00 | 99.38 |
| ATOM | 462 | C84 | CYC | B | 1 | 25.395 | 31.205 | 44.130 | 1.00 | 97.23 |
| ATOM | 463 | O85 | CYC | B | 1 | 26.318 | 32.274 | 44.541 | 1.00 | 95.57 |
| ATOM | 464 | O79 | CYC | B | 1 | 25.765 | 26.665 | 38.880 | 1.00 | 74.76 |
| ATOM | 465 | C68 | CYC | B | 1 | 21.737 | 23.120 | 38.324 | 1.00 | 39.41 |
| ATOM | 466 | C69 | CYC | B | 1 | 20.223 | 23.496 | 38.137 | 1.00 | 38.59 |
| ATOM | 467 | C70 | CYC | B | 1 | 19.523 | 23.355 | 39.421 | 1.00 | 38.22 |
| ATOM | 468 | N71 | CYC | B | 1 | 20.564 | 22.987 | 40.353 | 1.00 | 50.02 |
| ATOM | 469 | C72 | CYC | B | 1 | 20.399 | 22.763 | 41.607 | 1.00 | 55.62 |
| ATOM | 470 | C90 | CYC | B | 1 | 21.157 | 21.536 | 42.121 | 1.00 | 57.53 |
| ATOM | 471 | O96 | CYC | B | 1 | 20.407 | 20.319 | 41.993 | 1.00 | 56.55 |
| ATOM | 472 | C91 | CYC | B | 1 | 21.664 | 21.940 | 43.578 | 1.00 | 63.18 |
| ATOM | 473 | O97 | CYC | B | 1 | 21.600 | 20.757 | 44.471 | 1.00 | 63.88 |
| ATOM | 474 | C92 | CYC | B | 1 | 23.186 | 22.499 | 43.622 | 1.00 | 66.58 |
| ATOM | 475 | O98 | CYC | B | 1 | 23.971 | 21.462 | 44.307 | 1.00 | 68.12 |
| ATOM | 476 | C93 | CYC | B | 1 | 23.135 | 23.867 | 44.446 | 1.00 | 67.49 |
| ATOM | 477 | O99 | CYC | B | 1 | 22.357 | 24.774 | 43.597 | 1.00 | 66.74 |
| ATOM | 478 | C94 | CYC | B | 1 | 24.493 | 24.656 | 44.683 | 1.00 | 74.63 |
| ATOM | 479 | O95 | CYC | B | 1 | 24.178 | 25.865 | 45.490 | 1.00 | 80.12 |
| ATOM | 480 | O73 | CYC | B | 1 | 19.735 | 23.526 | 42.349 | 1.00 | 63.35 |
| ATOM | 481 | O58 | CYC | B | 1 | 23.106 | 22.977 | 35.125 | 1.00 | 40.42 |
| ATOM | 482 | C54 | CYC | B | 1 | 20.742 | 22.893 | 32.977 | 1.00 | 18.54 |
| ATOM | 483 | C14 | CYC | B | 1 | 19.521 | 20.648 | 31.087 | 1.00 | 23.61 |
| ATOM | 484 | C19 | CYC | B | 1 | 17.911 | 20.963 | 31.644 | 1.00 | 16.19 |
| ATOM | 485 | C13 | CYC | B | 1 | 19.810 | 21.781 | 30.035 | 1.00 | 19.97 |
| ATOM | 486 | O20 | CYC | B | 1 | 21.223 | 21.655 | 29.535 | 1.00 | 19.41 |
| ATOM | 487 | C12 | CYC | B | 1 | 18.975 | 21.668 | 28.869 | 1.00 | 17.80 |
| ATOM | 488 | C8 | CYC | B | 1 | 19.095 | 20.197 | 28.184 | 1.00 | 20.86 |
| ATOM | 489 | C3 | CYC | B | 1 | 18.129 | 20.072 | 26.867 | 1.00 | 26.70 |
| ATOM | 490 | C7 | CYC | B | 1 | 16.492 | 20.310 | 27.375 | 1.00 | 27.90 |
| ATOM | 491 | C2 | CYC | B | 1 | 18.448 | 21.212 | 25.824 | 1.00 | 28.19 |
| ATOM | 492 | BR | BR | C | 1 | 34.062 | 6.612 | 30.395 | 0.50 | 33.08 |
| ATOM | 493 | O | HOH | W | 1 | 19.167 | 24.790 | 26.224 | 1.00 | 26.47 |
| ATOM | 494 | O | HOH | W | 2 | 23.897 | 21.958 | 31.132 | 1.00 | 22.60 |
| ATOM | 495 | O | HOH | W | 3 | 21.553 | 23.642 | 27.485 | 1.00 | 29.42 |
| ATOM | 496 | O | HOH | W | 4 | 24.680 | 19.970 | 37.794 | 1.00 | 27.43 |
| ATOM | 497 | O | HOH | W | 5 | 30.918 | 19.401 | 40.676 | 1.00 | 23.25 |
| ATOM | 498 | O | HOH | W | 6 | 16.708 | 17.200 | 40.896 | 1.00 | 28.59 |
| ATOM | 499 | O | HOH | W | 7 | 16.516 | 25.080 | 41.353 | 1.00 | 25.88 |
| ATOM | 500 | O | HOH | W | 8 | 18.741 | 11.412 | 20.841 | 1.00 | 29.70 |
| ATOM | 501 | O | HOH | W | 9 | 27.307 | 23.459 | 25.693 | 1.00 | 22.59 |
| ATOM | 502 | O | HOH | W | 10 | 29.313 | −4.298 | 41.568 | 1.00 | 37.18 |
| ATOM | 503 | O | HOH | W | 11 | 24.485 | 23.989 | 32.854 | 1.00 | 35.58 |
| ATOM | 504 | O | HOH | W | 12 | 17.430 | 11.457 | 36.970 | 1.00 | 26.36 |
| ATOM | 505 | O | HOH | W | 13 | 22.518 | 16.744 | 15.421 | 1.00 | 37.65 |
| ATOM | 506 | O | HOH | W | 14 | 22.764 | 17.648 | 22.807 | 1.00 | 29.54 |
| ATOM | 507 | O | HOH | W | 15 | 22.916 | 12.486 | 18.554 | 1.00 | 30.85 |
| ATOM | 508 | O | HOH | W | 16 | 21.127 | 13.160 | 16.233 | 1.00 | 67.05 |
| ATOM | 509 | O | HOH | W | 18 | 33.941 | 3.332 | 34.867 | 1.00 | 47.13 |
| ATOM | 510 | O | HOH | W | 19 | 28.659 | 24.132 | 37.361 | 1.00 | 34.15 |
| ATOM | 511 | O | HOH | W | 20 | 26.049 | 12.100 | 38.687 | 1.00 | 43.38 |
| ATOM | 512 | O | HOH | W | 22 | 22.998 | 5.484 | 43.119 | 1.00 | 56.07 |
| ATOM | 513 | O | HOH | W | 23 | 21.091 | 10.590 | 19.804 | 1.00 | 37.65 |
| ATOM | 514 | O | HOH | W | 24 | 27.553 | 20.681 | 37.920 | 1.00 | 40.51 |
| ATOM | 515 | O | HOH | W | 25 | 21.539 | 4.646 | 32.538 | 1.00 | 35.17 |
| ATOM | 516 | O | HOH | W | 35 | 36.200 | 4.986 | 34.099 | 1.00 | 55.94 |
| ATOM | 517 | O | HOH | W | 36 | 25.301 | 25.430 | 41.805 | 1.00 | 45.43 |
| ATOM | 518 | O | HOH | W | 37 | 28.063 | 14.145 | 40.069 | 1.00 | 39.11 |
| ATOM | 519 | O | HOH | W | 38 | 20.561 | 25.768 | 50.428 | 1.00 | 38.92 |
| ATOM | 520 | O | HOH | W | 39 | 22.841 | 23.744 | 25.080 | 1.00 | 40.88 |
| ATOM | 521 | O | HOH | W | 40 | 16.781 | 11.726 | 39.998 | 1.00 | 65.62 |

APPENDIX 1-continued

| ATOM | 522 | O | HOH | W | 41 | 29.705 | 23.094 | 40.234 | 1.00 | 40.48 |
| ATOM | 523 | O | HOH | W | 42 | 18.375 | 14.116 | 41.324 | 1.00 | 58.97 |
| ATOM | 524 | O | HOH | W | 43 | 15.538 | 9.778 | 20.639 | 1.00 | 61.25 |
| ATOM | 525 | O | HOH | W | 44 | 34.144 | 2.745 | 20.168 | 1.00 | 48.45 |
| ATOM | 526 | O | HOH | W | 45 | 20.621 | 8.952 | 42.429 | 1.00 | 33.04 |
| ATOM | 527 | O | HOH | W | 46 | 17.087 | 6.329 | 28.850 | 1.00 | 32.70 |
| ATOM | 528 | O | HOH | W | 47 | 25.800 | 23.668 | 39.622 | 1.00 | 46.80 |
| ATOM | 529 | O | HOH | W | 48 | 16.978 | 27.199 | 25.066 | 1.00 | 44.77 |
| ATOM | 530 | O | HOH | W | 49 | 22.764 | 7.118 | 24.736 | 1.00 | 38.06 |
| ATOM | 531 | O | HOH | W | 50 | 24.770 | 22.332 | 46.924 | 1.00 | 48.70 |
| ATOM | 532 | O | HOH | W | 51 | 21.688 | 25.678 | 41.327 | 1.00 | 52.53 |
| ATOM | 533 | O | HOH | W | 52 | 19.396 | 17.922 | 42.396 | 1.00 | 53.49 |
| ATOM | 534 | O | HOH | W | 53 | 21.375 | 18.431 | 46.997 | 1.00 | 57.91 |
| ATOM | 535 | O | HOH | W | 54 | 19.736 | 20.961 | 17.193 | 1.00 | 46.33 |
| ATOM | 536 | O | HOH | W | 55 | 30.374 | 4.915 | 45.161 | 1.00 | 52.15 |
| ATOM | 537 | O | HOH | W | 56 | 18.588 | 26.408 | 48.436 | 1.00 | 44.58 |
| ATOM | 538 | O | HOH | W | 57 | 23.722 | 24.504 | 28.990 | 1.00 | 38.53 |

What is claimed is:

1. A method of treating a mammal suffering from an agonist disorder, said method comprising administering to said mammal an effective amount of a composition comprising a crystal formed by insulin-like growth factor-1 (IGF-1) of SEQ ID NO: 1 that diffracts x-ray radiation to produce a diffraction pattern representing the three-dimensional structure of the IGF-1, and has approximately the following cell constants a=31.831 Å, b=71.055 Å, c=65.995 Å, and a space group of $C222_1$, and $\alpha=\beta=\gamma$, wherein the IGF-1 is biologically active when resolubilized, wherein said agonist disorder is selected from the group consisting of hyperglycemic disorders, obesity, increased mass-to-lean ratio, heart dysfunctions, wasting, kidney disorders, lung diseases, neurological disorders, neuromuscular disorders, GH- insufficiency, whole body growth disorders, Turner's syndrome, and immunological disorders.

2. The method of claim 1 wherein the mammal is human.

3. The method of claim 1 wherein the disorder is diabetes, obesity, a heart dysfunction, AIDS-related wasting, a kidney disorder, a neurological disorder, a whole body growth disorder, or an immunological disorder.

4. The method of claim 1 wherein the hyperglycemic disorder is selected from the group consisting of Type I diabetes, Type II diabetes, severe insulin-resistance, hyperinsulinemia, hyperlipidemia, insulin-resistant diabetes, Mendenhall's Syndrome, Werner Syndrome, leprechaunism, lipoatrophic diabetes, and other lipoatrophies.

5. The method of claim 1 wherein the kidney disorder is selected from the group consisting of acute and chronic renal insufficiency, end-stage chronic renal failure, glomerulonephritis, interstitial nephritis, pyelonephritis, glornerulosel-erosis, Kirumeistiel-Wilson Syndrome in a diabetic patient, and kidney failure after kidney transplantation.

6. The method of claim 1 wherein the immunological disorder is selected from the group consisting of immunodeficiencies, decreased CD4 counts, decreased immune tolerance, and chemotherapy-induced tissue damage.

7. The method of claim 1 wherein the neurological or neuromuscular disorder is selected from the group consisting of peripheral neuropathy, multiple sclerosis, muscular dystrophy, myotonie dystrophy, and catabolic states associated with wasting.

8. The method of claim 1 wherein the whole body growth disorder is selected from the group consisting of short stature and Laron's syndrome.

* * * * *

UNITED STATES PATENT AND TRADEMARK OFFICE
CERTIFICATE OF CORRECTION

| | | |
|---|---|---|
| PATENT NO. | : 7,238,658 B2 | Page 1 of 1 |
| APPLICATION NO. | : 11/107672 | |
| DATED | : July 3, 2007 | |
| INVENTOR(S) | : Schaffer et al. | |

It is certified that error appears in the above-identified patent and that said Letters Patent is hereby corrected as shown below:

Amend claim 4 at Column 56, line 55 should read;
  Mendenhall's ~~Syndrone~~ Syndrome, Werner Syndrome, leprechaunism,

Amend claim 5 at Column 56, line 61-62 should read;
  pyelonephritis, ~~glorneruloselerosis~~ glomerulosclerosis, Kirumeistiel-Wilson Syndrome in a diabetic patient,

Amend claim 7 at Column 57, line 4 should read;
  dystrophy, ~~myotonic~~ myotonic dystrophy, and catabolic states associ- Signed and Sealed this Eighteenth Day of May, 2010

David J. Kappos
*Director of the United States Patent and Trademark Office*

SEQUENCE LISTING

<160> NUMBER OF SEQ ID NOS: 5

<210> SEQ ID NO 1
<211> LENGTH: 70
<212> TYPE: PRT
<213> ORGANISM: Homo sapiens

<400> SEQUENCE: 1

Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr Gly
                20                  25                  30

Tyr Gly Ser Ser Arg Arg Ala Pro Gln Thr Gly Ile Val Asp
                35                  40                  45

Glu Cys Cys Phe Arg Ser Cys Asp Leu Arg Arg Leu Glu Met Tyr
                50                  55                  60

Cys Ala Pro Leu Lys Pro Ala Lys Ser Ala
                65                  70

<210> SEQ ID NO 2
<211> LENGTH: 67
<212> TYPE: PRT
<213> ORGANISM: Homo sapiens

<400> SEQUENCE: 2

Ala Tyr Arg Pro Ser Glu Thr Leu Cys Gly Gly Glu Leu Val Asp
1               5                   10                  15

Thr Leu Gln Phe Val Cys Gly Asp Arg Gly Phe Tyr Phe Ser Arg
                20                  25                  30

Pro Ala Ser Arg Val Ser Arg Arg Ser Arg Gly Ile Val Glu Glu
                35                  40                  45

Cys Cys Phe Arg Ser Cys Asp Leu Ala Leu Leu Glu Thr Tyr Cys
                50                  55                  60

Ala Thr Pro Ala Lys Ser Glu
                65

<210> SEQ ID NO 3
<211> LENGTH: 50
<212> TYPE: PRT
<213> ORGANISM: Homo sapiens

```
<400> SEQUENCE: 3

Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Gly
             20                  25                  30

Ile Val Glu Gln Cys Cys Thr Ser Ile Cys Ser Leu Tyr Gln Leu
                 35                  40                  45

Glu Asn Tyr Cys Asn
                 50

<210> SEQ ID NO 4
<211> LENGTH: 16
<212> TYPE: PRT
<213> ORGANISM: Artificial Sequence
<220> FEATURE:
<223> OTHER INFORMATION: Sequence is synthesized.

<400> SEQUENCE: 4

Arg Asn Cys Phe Glu Ser Val Ala Ala Leu Arg Arg Cys Met Tyr
 1               5                  10                  15

Gly

<210> SEQ ID NO 5
<211> LENGTH: 56
<212> TYPE: PRT
<213> ORGANISM: Artificial Sequence
<220> FEATURE:
<223> OTHER INFORMATION: Residues observed in IGF-1 structure.

<400> SEQUENCE: 5

Glu Thr Leu Cys Gly Ala Glu Leu Val Asp Ala Leu Gln Phe Val
 1               5                  10                  15

Cys Gly Asp Arg Gly Phe Tyr Phe Asn Lys Pro Thr Gly Tyr Gly
             20                  25                  30

Ser Ser Thr Gly Ile Val Asp Glu Cys Cys Phe Arg Ser Cys Asp
                 35                  40                  45

Leu Arg Arg Leu Glu Met Tyr Cys Ala Pro Leu
                 50                  55
```